(12) United States Patent
Parham et al.

(10) Patent No.: US 11,545,634 B2
(45) Date of Patent: *Jan. 3, 2023

(54) HETEROCYCLIC SPIRO COMPOUNDS

(71) Applicant: Merck Patent GmbH, Darmstadt (DE)

(72) Inventors: Amir Hossain Parham, Frankfurt Am Main (DE); Elvira Montenegro, Weinheim (DE); Anja Jatsch, Frankfurt Am Main (DE); Christof Pflumm, Darmstadt (DE); Jonas Valentin Kroeber, Frankfurt Am Main (DE); Tobias Grossman, Darmstadt (DE); Thomas Eberle, Landau (DE); Lars Dobelmann-Mara, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 110 days.

This patent is subject to a terminal disclaimer.

(21) Appl. No.: 16/869,274

(22) Filed: May 7, 2020

(65) Prior Publication Data

US 2020/0266364 A1 Aug. 20, 2020

Related U.S. Application Data

(63) Continuation of application No. 15/105,759, filed as application No. PCT/EP2014/003120 on Nov. 21, 2014, now Pat. No. 10,777,750.

(30) Foreign Application Priority Data

Dec. 19, 2013 (EP) .................................. 13005938

(51) Int. Cl.
*H01L 51/00* (2006.01)
*C07D 307/94* (2006.01)
*C07F 9/655* (2006.01)
*C07D 405/04* (2006.01)
*C07D 405/10* (2006.01)
*C07D 409/04* (2006.01)
*C09K 11/06* (2006.01)
*C07F 15/00* (2006.01)
*C07F 5/02* (2006.01)
*C09K 11/02* (2006.01)
*H01L 51/50* (2006.01)

(52) U.S. Cl.
CPC ........ *H01L 51/0073* (2013.01); *C07D 307/94* (2013.01); *C07D 405/04* (2013.01); *C07D 405/10* (2013.01); *C07D 409/04* (2013.01); *C07F 5/025* (2013.01); *C07F 9/65517* (2013.01); *C07F 15/0033* (2013.01); *C07F 15/0086* (2013.01); *C09K 11/025* (2013.01); *C09K 11/06* (2013.01); *H01L 51/0052* (2013.01); *H01L 51/0056* (2013.01); *H01L 51/0067* (2013.01); *H01L 51/0072* (2013.01); *H01L 51/0074* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/5012* (2013.01); *H01L 51/5072* (2013.01); *H01L 51/5076* (2013.01); *Y02E 10/549* (2013.01)

(58) Field of Classification Search
CPC .. C07F 15/0033; C07F 15/0086; C07F 5/025; C07F 9/65517; H01L 51/0056; H01L 51/0074; H01L 51/0073; H01L 51/0072; H01L 51/0067; H01L 51/0052; H01L 51/5012; H01L 51/5076; H01L 51/5072; C07D 307/94; C07D 405/04; C07D 405/10; C07D 409/04; C09K 11/06; C09K 11/025; C09K 2211/1007; C09K 2211/1011; C09K 2211/1029; C09K 2211/1044; C09K 2211/1059; C09K 2211/1088; C09K 2211/1092; Y02E 10/549

USPC .......................................................... 252/500
See application file for complete search history.

(56) References Cited

U.S. PATENT DOCUMENTS

| | | | |
|---|---|---|---|
| 10,777,750 B2 * | 9/2020 | Parham | C07D 409/04 |
| 2008/0093980 A1 | 4/2008 | Stoessel et al. | |
| 2012/0126179 A1 | 5/2012 | Parham et al. | |
| 2013/0256645 A1 | 10/2013 | Min et al. | |
| 2014/0225040 A1 | 8/2014 | Parham et al. | |
| 2014/0332787 A1 | 11/2014 | Hong et al. | |
| 2017/0117485 A1 | 4/2017 | Cho et al. | |

FOREIGN PATENT DOCUMENTS

| | | |
|---|---|---|
| CN | 105164120 A | 12/2015 |
| CN | 105358554 A | 2/2016 |
| DE | 102009032922 A1 | 1/2011 |
| JP | 2008506657 A | 3/2008 |
| JP | 2009266927 A | 11/2009 |
| KR | 10-2013-0077470 A | 7/2013 |
| KR | 20140029035 B1 | 3/2014 |
| TW | 201439277 A | 10/2014 |
| TW | 201512172 A | 4/2016 |
| WO | 2012074210 A2 | 6/2012 |
| WO | 2013017189 A1 | 2/2013 |
| WO | 2013100464 A1 | 7/2013 |
| WO | 2013100467 A1 | 7/2013 |

(Continued)

OTHER PUBLICATIONS

Translation of WO 2013100464, Jul. 4, 2013. (Year: 2013).*

(Continued)

*Primary Examiner* — Douglas J McGinty
(74) *Attorney, Agent, or Firm* — Faegre Drinker Biddle & Reath LLP

(57) ABSTRACT

The present invention relates to spiro compounds containing electron-conducting groups and to electronic devices, in particular organic electroluminescent devices, comprising these compounds.

27 Claims, No Drawings

(56) References Cited

FOREIGN PATENT DOCUMENTS

| WO | WO-2014094963 A1 * | 6/2014 | ........... C07D 209/82 |
|----|-------------------|--------|-----------------|
| WO | 2014129846 A1 | 8/2014 | |
| WO | 2014185751 A1 | 11/2014 | |

OTHER PUBLICATIONS

Japanese Office Action dated Aug. 24, 2018 in corresponding Japanese Patent Application No. 2016-541141.
Taiwanese Office Action dated Aug. 9, 2018 in corresponding Taiwanese Patent Application No. 103143914.
STN Reg. No. 1799406-51-1, Jul. 14, 2015.
English Translation for WO 2013/100464, Jul. 4, 2013.
Jeon et al., "Fluorenobenzofuran as the core structure of high triplet energy host materials for green phosphorescent organic light-emitting diodes," J. Matter. Chem., vol. 22, pp. 10537-10541 (2012).
First Office Action in Patent Chinese Application Serial No. 201480068667.3, dated Jan. 2, 2018.
International Preliminary Reporton Patentability received for PCT Patent Application No. PCT/EP2014/003120, dated Jun. 30, 2016, 19 pages (11 pages of English Translation and 8 pages of Original Document).
International Search Report and Written Opinion received for PCT Patent Application No. PCT/EP2014/003120, dated Jun. 16, 2015, 25 pages (12 pages of English Translation and 13 pages of Original Document).

* cited by examiner

HETEROCYCLIC SPIRO COMPOUNDS

RELATED APPLICATIONS

This application is a continuation of U.S. patent application Ser. No. 15/105,759, filed Jun. 17, 2016, which is a national stage application filed pursuant to 35 U.S.C. § 371 of International Application No. PCT/EP2014/003120, filed Nov. 21, 2014, which claims the benefit of European Patent Application No. 13005938.9, filed Dec. 19, 2013, which is incorporated herein by reference in its entirety.

The present invention relates to spiro compounds containing at least one electron-transporting group which are suitable for use in electronic devices. Furthermore, the present invention relates to processes for the preparation thereof and to electronic devices.

Electronic devices which comprise organic, organometallic and/or polymeric semiconductors are increasing in importance; they are employed in many commercial products for cost reasons and owing to their performance. Examples which may be mentioned here are organic-based charge-transport materials (for example triarylamine-based hole transporters) in photocopiers, organic or polymeric light-emitting diodes (OLEDs or PLEDs) and in display devices, or organic photoreceptors in photocopiers. Organic solar cells (O-SC), organic field-effect transistors (O-FET), organic thin-film transistors (O-TFT), organic integrated circuits (O-IC), organic optical amplifiers and organic laser diodes (O-lasers) are at an advanced stage of development and may achieve major importance in the future.

Irrespective of the particular application, many of these electronic devices have the following general layer structure, which can be adapted for the particular application:
(1) substrate,
(2) electrode, frequently metallic or inorganic, but also made from organic or polymeric, conductive materials,
(3) charge-injection layer(s) or interlayer(s), for example for compensation of electrode unevenness ("planarisation layer"), frequently made from a conductive, doped polymer,
(4) organic semiconductors,
(5) optionally further charge-transport, charge-injection or charge-blocking layers,
(6) counterelectrode, materials as mentioned under (2),
(7) encapsulation.

The above arrangement represents the general structure of an organic, electronic device, where various layers can be combined, resulting in the simplest case in an arrangement comprising two electrodes, between which an organic layer is located. In this case, the organic layer fulfils all functions, including the emission of light in the case of OLEDs. A system of this type is described, for example, in WO 90/13148 A1 based on poly-(p-phenylenes).

Electronic devices which comprise spiro compounds containing at least one electron-transporting group are described, inter alia, in the publication WO 2013/100464 A1. The spiro compounds described explicitly therein are only substituted at the 2',7'-positions of the rings by electron-conducting groups, where, in this numbering, the spiro compound is substituted at positions 3 and 4 in such a way that a dibenzofuran group is formed together with an aryl ring of the spiro skeleton.

Known electronic devices have a usable property profile. However, it is constantly necessary to improve the properties of these devices.

These properties include, in particular, the processability of the compounds employed for the production of the electronic devices. Thus, known compounds are relatively oxidation-sensitive in solution. Furthermore, known compounds exhibit very limited solubility. Furthermore, known compounds have a strong tendency towards decomposition at high temperatures, which hinders sublimation. A further problem is the energy efficiency with which an electronic device achieves the specified object. In the case of organic light-emitting diodes, which may be based both on low-molecular-weight compounds and also on polymeric materials, the light yield, in particular, should be high, so that as little electrical power as possible has to be input in order to achieve a certain light flux. Furthermore, the lowest possible voltage should also be necessary in order to achieve a specified luminous density. A further problem is, in particular, the lifetime of the electronic devices.

The object of the present invention is therefore the provision of novel compounds which lead to electronic devices having improved properties. In particular, the object is to provide hole-blocking materials, electron-injection materials and/or electron-transport materials which exhibit improved properties with respect to processability, handling, efficiency, operating voltage and/or lifetime. Furthermore, the compounds should be as simple to process as possible, in particular should exhibit good solubility and film formation.

A further object can be regarded as being the provision of electronic devices having excellent performance as inexpensively as possible and in constant quality.

It should furthermore be possible to employ or adapt the electronic devices for many purposes. In particular, the performance of the electronic devices should be retained over a broad temperature range.

Surprisingly, it has been found that these and further objects which are not mentioned explicitly, but can readily be derived or deduced from the correlations discussed in the introduction hereto, are achieved by compounds having all features of Patent Claim 1. Advantageous modifications of the compounds according to the invention are protected in the claims which are dependent on Claim 1.

The invention thus relates to a compound containing at least one structure of the formula (I)

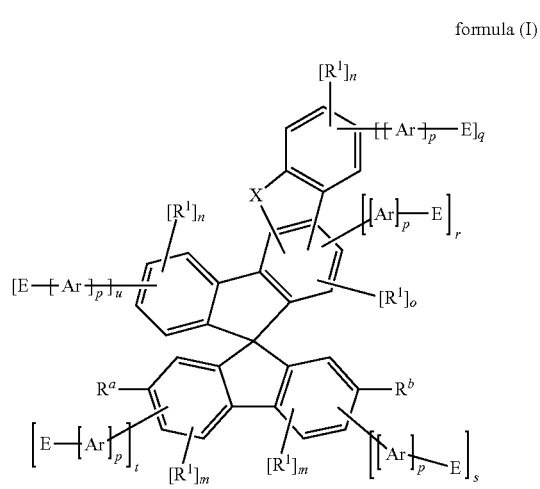

formula (I)

where the following applies to the symbols used:
X is O, S or $C(R^1)_2$, preferably O or S and particularly preferably O;

Ar is on each occurrence, identically or differently, an aryl group having 6 to 40 C atoms or a heteroaryl group having 3 to 40 C atoms, each of which may be substituted by one or more radicals $R^1$;

$R^1$ is on each occurrence, identically or differently, H, D, F, Cl, Br, I, CHO, C(=O)Ar$^1$, P(=O)(Ar$^1$)$_2$, S(=O)Ar$^1$, S(=O)$_2$Ar$^1$, CN, NO$_2$, Si(R$^2$)$_3$, B(OR$^2$)$_2$, OSO$_2$R$^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent CH$_2$ groups may be replaced by R$^2$C=CR$^2$, C≡C, Si(R$^2$)$_2$, Ge(R$^2$)$_2$, Sn(R$^2$)$_2$, C=O, C=S, C=Se, P(=O)(R$^2$), SO, SO$_2$, O, S or CONR$^2$ and where one or more H atoms may be replaced by D, F, Cl, Br, I, CN or NO$_2$, or an aromatic or heteroaromatic ring system having 5 to 40 aromatic ring atoms, which may in each case be substituted by one or more radicals $R^2$, or an aryloxy or heteroaryloxy group having 5 to 40 aromatic ring atoms, which may be substituted by one or more radicals $R^2$, or a combination of these systems; two or more adjacent substituents $R^1$ here may also form a mono- or polycyclic, aliphatic or aromatic ring system with one another;

$R^2$ is on each occurrence, identically or differently, H, D, F, Cl, Br, I, CHO, C(=O)Ar$^1$, P(=O)(Ar$^1$)$_2$, S(=O)Ar$^1$, S(=O)$_2$Ar$^1$, CN, NO$_2$, Si(R$^3$)$_3$, B(OR$^3$)$_2$, OSO$_2$R$^3$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^3$, where one or more non-adjacent CH$_2$ groups may be replaced by C≡C, Si(R$^3$)$_2$, Ge(R$^3$)$_2$, Sn(R$^3$)$_2$, C=O, C=S, C=Se, P(=O)(R$^3$), SO, SO$_2$, O, S or CONR$^3$ and where one or more H atoms may be replaced by D, F, Cl, Br, I, CN or NO$_2$, or a combination of these systems; two or more adjacent substituents $R^2$ here may also form a mono- or polycyclic, aliphatic or aromatic ring system with one another;

Ar$^1$ is on each occurrence, identically or differently, an aromatic or heteroaromatic ring system having 5 to 30 aromatic ring atoms, which may be substituted by one or more radicals $R^2$; two radicals Ar$^1$ here which are bonded to the same phosphorus atom may also be linked to one another by a single bond or a bridge selected from B(R$^3$), C(R$^3$)$_2$, Si(R$^3$)$_2$, C=O, C=NR$^3$, C=C(R$^3$)$_2$, O, S, S=O, SO$_2$, N(R$^3$), P(R$^3$) and P(=O)R$^3$;

$R^3$ is on each occurrence, identically or differently, H, D, F or an aliphatic, aromatic and/or heteroaromatic hydrocarbon radical having 1 to 20 C atoms, in which, in addition, H atoms may be replaced by F; two or more adjacent substituents $R^3$ here may also form a mono- or polycyclic, aliphatic or aromatic ring system with one another;

n is on each occurrence, identically or differently, 0, 1, 2, 3 or 4;

m is on each occurrence, identically or differently, 0, 1, 2 or 3;

is on each occurrence, identically or differently, 0, 1 or 2;

p, q, r, s, t, u are on each occurrence, identically or differently, 0 or 1;

E is an electron-transporting group, which may in each case be substituted by one or more radicals $R^1$;

$R^a$ is $R^1$ or a group —[Ar]$_p$-E, where Ar, p and E have the meaning given above;

$R^b$ is $R^1$ or a group —[Ar]$_p$-E, where Ar, p and E have the meaning given above;

with the proviso that the structure of the formula (I) contains at least one electron-transporting group E;

the sum of all indices m, s and t is less than 7;
the sum of all indices n, q and u is less than 9;
the sum of the indices r and o is less than 3;

$R^b$ represents H, D or F if $R^a$ is a group —[Ar]$_p$-E and the structure of the formula (I) contains at most two electron-transporting groups E; and, if $R^b$ is a group —[Ar]$_p$-E and the structure of the formula (I) contains at most two electron-transporting groups E, $R^a$ represents H, D or F.

The group X is connected to the spiro skeleton and an aryl radical, where the aryl radical additionally has a bond to the spiro skeleton. The bonding to the aryl radical and to the group X here takes place via adjacent carbon atoms of the spiro skeleton, so that, depending on the group X, a fluorene group (X=C(R$^1$)$_2$), a dibenzothiofuran group (X=S) or a dibenzofuran group (X=O) is formed.

According to a preferred embodiment, X in formula (I) represents oxygen or sulfur, particularly preferably oxygen. Accordingly, compounds containing at least one structure of the formula (Ia)

formula (Ia)

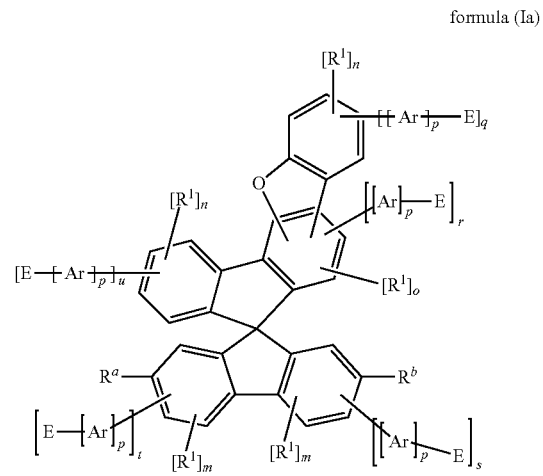

are particularly preferred, where the symbols used have the meaning given above for formula (I). The embodiments described as preferred below apply to a particular extent, in particular, to compounds of the formula (Ia).

"Adjacent carbon atoms" here means that the carbon atoms are bonded directly to one another. Furthermore, "adjacent radicals" in the definition of the radicals means that these radicals are bonded to the same carbon atom or to adjacent carbon atoms. These definitions apply correspondingly, inter alia, to the terms "adjacent groups" and "adjacent substituents".

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

An aromatic ring system in the sense of this invention contains 6 to 60 C atoms in the ring system. A heteroaromatic ring system in the sense of this invention contains 1 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, a C, N or O atom or a carbonyl group. Thus, for example, systems such as 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are interrupted, for example, by a linear or cyclic alkyl group or by a silyl group. Furthermore, systems in which two or more aryl or heteroaryl groups are bonded directly to one another, such as, for example, biphenyl or terphenyl, are likewise intended to be taken to be an aromatic or heteroaromatic ring system.

A cyclic alkyl, alkoxy or thioalkoxy group in the sense of this invention is taken to mean a monocyclic, bicyclic or polycyclic group.

For the purposes of the present invention, a $C_1$- to $C_{40}$-alkyl group, in which, in addition, individual H atoms or $CH_2$ groups may be substituted by the above-mentioned groups, is taken to mean, for example, the radicals methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system having 5-60 aromatic ring atoms, which may also in each case be substituted by the radicals mentioned above and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or transindenofluorene, trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

For further explanation of the preferred embodiments described below, the numbering on the spiro skeleton used herein is explained below, where rings A and B and rings C and D are in each case planar. Ring E is connected directly to ring A via a bond and via the group X, where the bonding of X to ring A takes place on a C atom which is adjacent to the C atom of ring A via which ring A is connected to ring E.

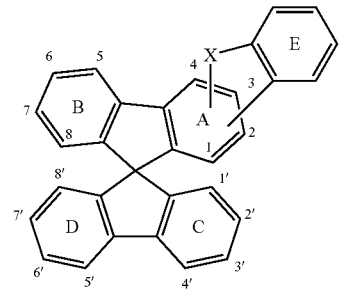

Numbering on the Spiro Skeleton

Rings A and E here form a fluorene, dibenzothiofuran or dibenzofuran group, in preferred embodiments a dibenzothiofuran or dibenzofuran group and particularly preferably a dibenzofuran group.

Preference is given to compounds containing structures of the formula (I) which are characterised in that the sum of the indices q, r, s, t and u is less than or equal to 3. The sum of the indices q, r, s, t and u is particularly preferably less than or equal to 3 and the groups $R^a$ and $R^b$ contain no electron-transporting groups E. Accordingly, preference is given to compounds pounds which contain at most 3, particularly preferably at most 2 and especially preferably precisely one electron-transporting group E.

Preference is furthermore given to compounds in which q is equal to 1, where in this case r=s=0 is particularly preferred. Especially preferably, q is equal to 1 and the sum of s, t and the electron-transporting groups E present in the groups $R^a$ and $R^b$ is less than or equal to 1, particularly preferably equal to 0. Preference is therefore given to compounds in which ring E contains one electron-transporting group E and rings C and D contain no electron-transporting group E.

It may furthermore be provided that u is preferably equal to 1. If u=1, r=s=0 is possible in a preferred embodiment. Particular preference is given to an embodiment in which u=1 and the sum of s, t and the electron-transporting groups E present in the groups $R^a$ and $R^b$ is less than or equal to 1, particularly preferably equal to 0. Accordingly, preference is given to compounds in which ring B contains one electron-transporting group E and rings C and D contain no electron-transporting group E.

In addition, o can preferably be equal to 1. If o=1, r=s=0 is possible in a preferred embodiment. Particular preference is given to an embodiment in which o=1 and the sum of s, t and the electron-transporting groups E present in the groups $R^a$ and $R^b$ is less than or equal to 1, particularly preferably equal to 0. Accordingly, preference is given to compounds in which ring A contains one electron-transporting group E and rings C and D contain no electron-transporting group E.

According to a further embodiment of the present invention, preference is given to compounds in which one of the radicals $R^a$ and $R^b$ denotes a group —$[Ar]_p$-E, preferably E, where Ar, p and E have the meaning given above. If one of the radicals $R^a$ and $R^b$ represents a group —$[Ar]_p$-E, the sum of s and t is preferably equal to 0, where in this case the sum of q, u and o is particularly preferably less than or equal to 1, preferably equal to 0.

According to a particular embodiment, s and t are not simultaneously 1. If t is equal to 1, s can preferably be equal to 0. If s is equal to 1, t can preferably be equal to 0. Accordingly, it may preferably be provided that the sum of s and t is be equal to 1, where in this case the sum of q, u and o is particularly preferably less than or equal to 1, preferably equal to 0. It may furthermore be provided, if the sum of s and t is equal to 1, that the groups $R^a$ and $R^b$ contain no electron-transporting groups E. In a particularly preferred embodiment, it may be provided that the sum of s and t is equal to 1, that the groups $R^a$ and $R^b$ contain no electron-transporting groups E and that the sum of q, u and o is less than or equal to 1, preferably equal to 0.

Accordingly, preference is given to compounds in which rings C and D contain precisely one electron-transporting group E, where rings A, B and E contain at most one and preferably no electron-transporting group E.

Preference is furthermore given to compounds in which at least one radical containing an electron-transporting group E is bonded in position 1, 1', 3, 3', 4, 4', 5, 5', 6, 6', 8, 8' of the spirobifluorene skeleton.

It may furthermore be provided that the structure of the formula (I) preferably contains at most 4, preferably at most 3, particularly preferably one or two, especially preferably precisely one electron-transporting group E.

Preference is furthermore given to compounds of the formula (I) in which the sum of all n, m and o is less than or equal to 4, preferably less than or equal to 2. Preference is therefore given to compounds which contain at most 4, particularly preferably at most 2 radicals $R^1$.

In addition, preference is given to compounds which are distinguished by the fact that p is 0, so that E is bonded directly to the benzofuran or spiro group.

Preference is furthermore given to compounds which contain structures of the formulae (II), (III), (IV), (V), (VI) and/or (VII)

formula (II)

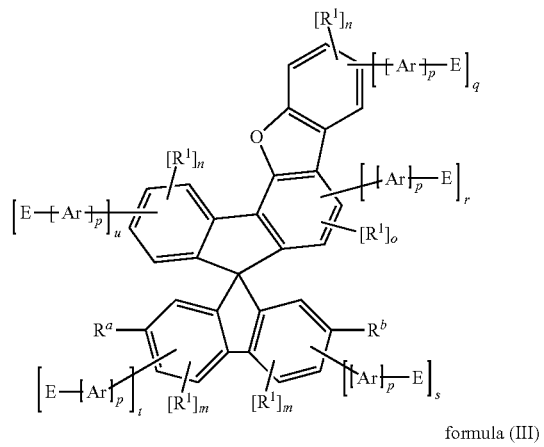

formula (III)

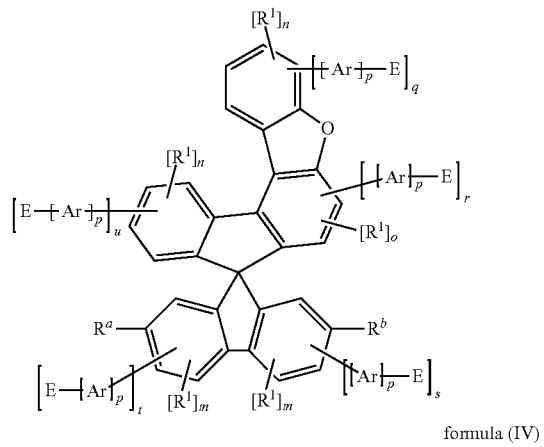

formula (IV)

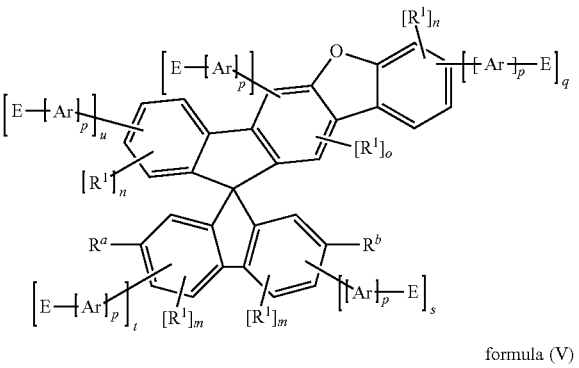

formula (V)

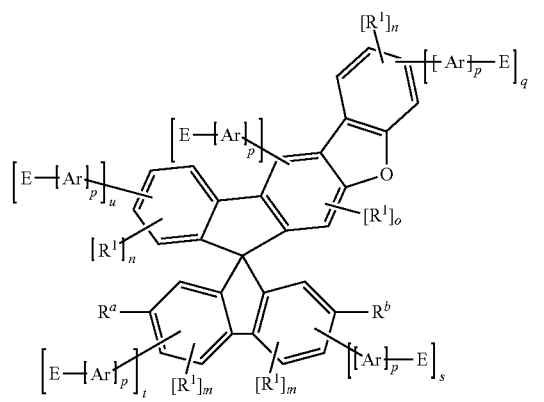

-continued formula (VI)

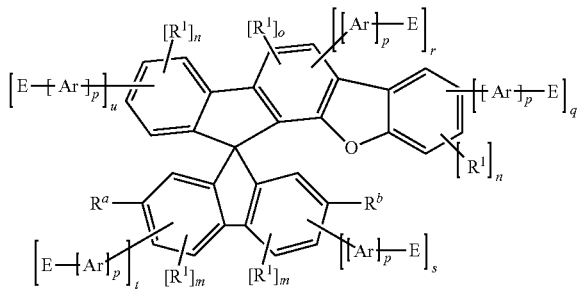

formula (VII)

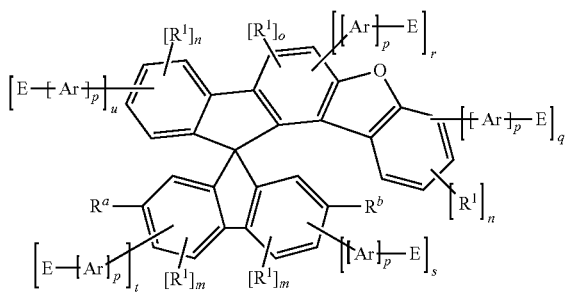

where the symbols shown have the meaning described above.

Of the said compounds of the formulae (II) to (VII), preference is given to compounds of the formulae (II) and (III), where compounds of the formula (II) are particularly preferred.

According to a preferred embodiment, the indices n, m and o in the formulae (I), (Ia) and (II) to (VII) are on each occurrence, identically or differently, 0 or 1.

The compound containing structures of the formula (I) can preferably contain radicals $R^1$, where these radicals $R^1$ are preferably selected on each occurrence, identically or differently, from the group consisting of H, D, F, Br, I, CN, $Si(R^2)_3$, $B(OR^2)_2$, $C(=O)Ar^1$, a straight-chain alkyl group having 1 to 10 C atoms or a straight-chain alkoxy group having 1 to 10 C atoms or an alkenyl group having 2 to 10 C atoms or a branched or cyclic alkoxy group having 3 to 10 C atoms or a branched or cyclic alkyl group having 3 to 10 C atoms, each of which may be substituted by one or more radicals $R^2$, where one or more H atoms may be replaced by D or F, or an aromatic or heteroaromatic ring system having 5 to 30 aromatic ring atoms, which may in each case be substituted by one or more radicals $R^2$; two adjacent radicals $R^1$ or $R^1$ with $R^2$ here may also form a mono- or polycyclic, aliphatic or aromatic ring system with one another. These radicals $R^1$ are particularly preferably selected on each occurrence, identically or differently, from the group consisting of H, D, F, a straight-chain alkoxy group having 1 to 6 C atoms or a branched or cyclic alkoxy group having 3 to 10 C atoms, a straight-chain alkyl group having 1 to 6 C atoms or a branched or cyclic alkyl group having 3 to 10 C atoms, where one or more H atoms may be replaced by D or F, or an aromatic or heteroaromatic ring system having 5 to 24 aromatic ring atoms, which may in each case be substituted by one or more radicals $R^2$; two adjacent radicals $R^1$ or $R^1$ with $R^2$ here may also form a mono- or polycyclic, aliphatic or aromatic ring system with one another. At least one, preferably both, of the radicals $R^1$ in formula (I) may particularly preferably represent an alkyl radical having 1 to 10 carbon atoms or an aryl group having 6 to 10 carbon atoms, which may be substituted by up to three radicals $R^2$.

The structure of the formula (I) contains at least one electron-transporting group E, which may optionally be substituted by one or more of the radicals $R^1$ defined in greater detail above. An electron-transporting group E is distinguished by the fact that, alone or in interaction with other groups, it improves the electron conductivity in one or more layers of an organic electronic device. In general, these groups have a relatively low LUMO (lowest unoccupied molecular orbital) energy.

The electron-transporting group E can preferably have an LUMO (lowest unoccupied molecular orbital) energy which is lower than −1.3 eV, very preferably lower than −2.5 eV and very particularly preferably lower than −2.7 eV.

Molecular orbitals, in particular also the highest occupied molecular orbital (HOMO) and the lowest unoccupied molecular orbital (LUMO), their energy levels and the energy of the lowest triplet state $T_1$ or of the lowest excited singlet state Si of the materials are determined via quantum-chemical calculations. In order to calculate organic substances without metals, firstly a geometry optimisation is carried out using the "Ground State/Semi-empirical/Default Spin/AM1/Charge 0/Spin Singlet" method. An energy calculation is subsequently carried out on the basis of the optimised geometry. The "TD-SCF/DFT/Default Spin/B3PW91" method with the "6-31G(d)" base set (charge 0, spin singlet) is used here. For metal-containing compounds, the geometry is optimised via the "Ground State/Hartree-Fock/Default Spin/LanL2 MB/Charge 0/Spin Singlet" method. The energy calculation is carried out analogously to the above-described method for the organic substances, with the difference that the "LanL2DZ" base set is used for the metal atom and the "6-31G(d)" base set is used for the ligands. The energy calculation gives the HOMO energy level HEh or LUMO energy level LEh in hartree units. The HOMO and LUMO energy levels in electron volts calibrated with reference to cyclic voltammetry measurements are determined therefrom as follows:

HOMO(eV)=((HEh*27.212)−0.9899)/1.1206

LUMO(eV)=((LEh*27.212)−2.0041)/1.385

For the purposes of this application, these values are to be regarded as HOMO and LUMO energy levels respectively of the materials.

The lowest triplet state $T_1$ is defined as the energy of the triplet state having the lowest energy which arises from the quantum-chemical calculation described.

The lowest excited singlet state Si is defined as the energy of the excited singlet state having the lowest energy which arises from the quantum-chemical calculation described.

The method described herein is independent of the software package used and always gives the same results. Examples of frequently used programs for this purpose are "Gaussian09 W" (Gaussian Inc.) and Q-Chem 4.1 (Q-Chem, Inc.).

Further preferably, the electron-transporting group E is characterised in that the electron mobility μ is $10^{-6}$ cm$^2$/(Vs) or more, very preferably $10^{-5}$ cm$^2$/(Vs) or more and very particularly preferably $10^{-4}$ cm$^2$/(Vs) or more.

The preferred electron-transporting groups include, inter alia, electron-deficient heteroaromatic groups and aryl or heteroaryl groups containing at least one strongly electron-attracting group.

According to a preferred embodiment, the electron-transporting group E is preferably an electron-deficient heteroaromatic group, which may be substituted by one or more radicals R$^1$. Still greater preference is given to heteroaromatic groups having 6 aromatic ring atoms, at least one, preferably 2 and very preferably at least three of which are an N atom, or heteroaromatic groups having 5 aromatic ring atoms, at least 2 of which are heteroatoms, preferably at least one of which is an N atom, which may be substituted by R$^1$, where further aryl or heteroaryl groups may in each case also be condensed onto these groups.

According to a particular aspect of the present invention, it may be provided that the electron-transporting group E is a heteroaryl group having 5 to 60 aromatic ring atoms, where N represent very preferred heteroatoms, where the electron-transporting group E may be substituted by one or more radicals R$^1$, which are independent of one another.

Preferred electron-transporting groups E contain at least one structure selected from the group of the pyridines, pyrazines, pyrimidines, pyridazines 1,2,4-tiazines, 1,3,5-triazines, quinolines, isoquinolines, quinoxalines, pyrazoles, imidazoles, benzimidazoles, thiazoles, benzothiazoles, oxazoles and benzoxazoles, particularly preferably from the group of the pyridazines, 1,2,4-triazines, 1,3,5-triazines, pyimidines, pyrazines, imidazoles, benzimidazoles and pyridines. These structures may be substituted here by one or more radicals R$^1$, which are independent of one another. The electron-transporting group is still more preferably a pyridine, pyrazine, pyrimidine, pyridazine or 1,3,5-triazine which is substituted by one or more radicals R$^1$.

It may furthermore be provided that the electron-transporting group E contains at least one structure of the formulae (E-1) to (E-10)

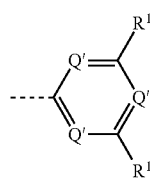
formula (E-1)

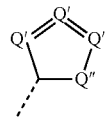
formula (E-2)

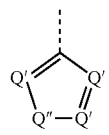
formula (E-3)

formula (E-4)

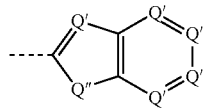
formula (E-5)

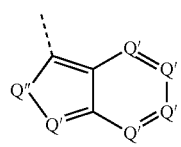
formula (E-6)

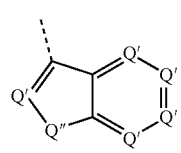
formula (E-7)

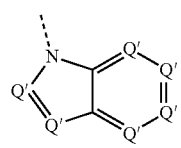
formula (E-8)

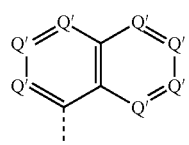
formula (E-9)

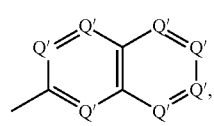
formula (E-10)

where the dashed bond marks the bonding position,
Q' represents on each occurrence, identically or differently, CR$^1$ or N, and
Q" represents NR$^1$, O or S,
where at least one Q' is equal to N and/or at least one Q" is equal to NR$^1$ and
R$^1$ is as defined above.

It may particularly preferably be provided that the electron-transporting group E has at least one structure of the formulae (E-11) to (E-19)

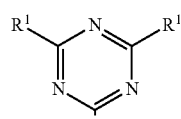
(formula E-11)

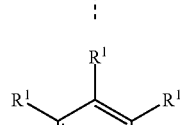
formula (E-12)

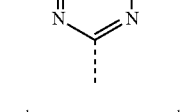
formula (E-13)

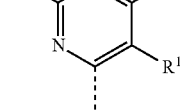
formula (E-14)

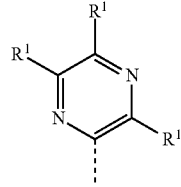

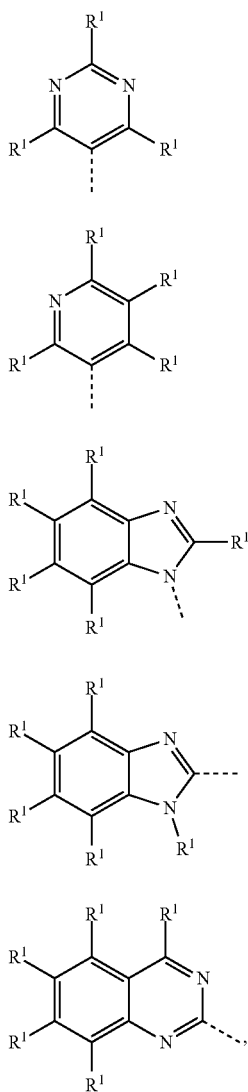

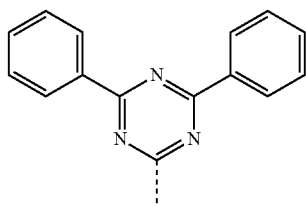
formula (E-20)

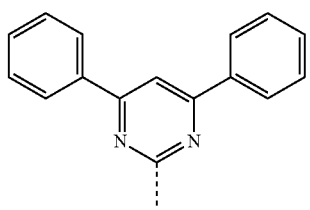
formula (E-21)

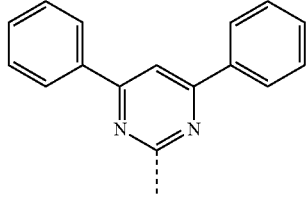
formula (E-22)

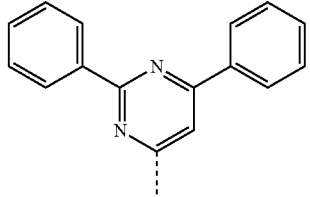
formula (E-23)

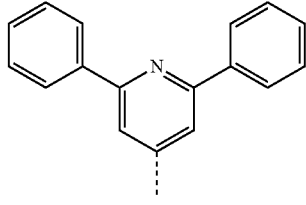
formula (E-24)

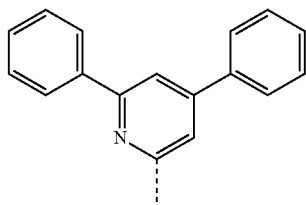
formula (E-25)

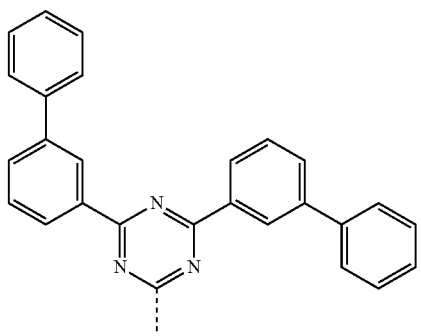

where the dashed bond marks the bonding position and $R^1$ has the meaning given above.

In the case of the formula (E-18), $R^1$ preferably does not stand for H or D.

For compounds containing structures of the formula (E-1) to formula (E-19), at least one, preferably at least two, of the radicals $R^1$ can preferably stand for Ar, where Ar has the meaning given above.

The substituents $R^1$ in the electron-transporting group E are preferably selected from the group consisting of H or an aromatic or heteroaromatic ring system having 5 to 60 aromatic ring atoms, which may in each case be substituted by one or more radicals $R^2$, where the groups of the formulae (E-11), (E-17) and (E-18) are even more preferred and the group of the formula (E-11) is most preferred.

Examples of very particularly preferred electron-transporting groups E, which may be substituted by one or more radicals $R^2$, which are independent of one another, where the dashed bonds denote the bonding position, are the following groups.

formula (E-26)
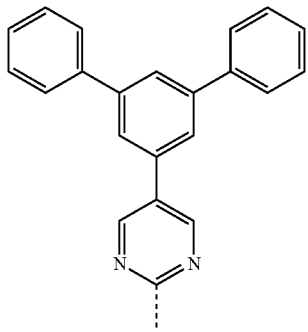

formula (E-27)
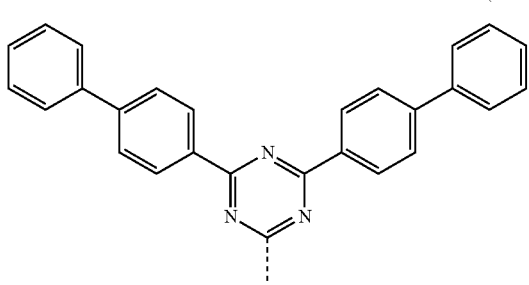

formula (E-28)
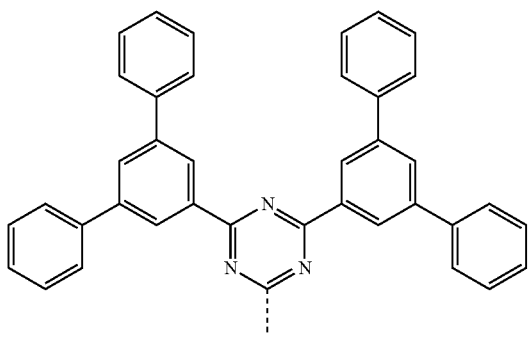

formula (E-29)
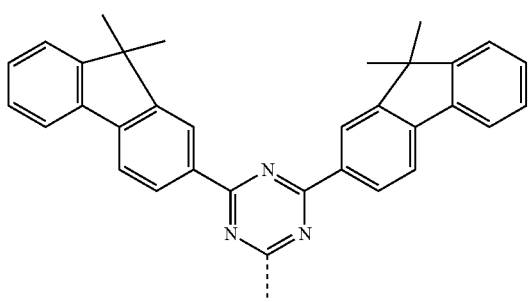

formula (E-30)
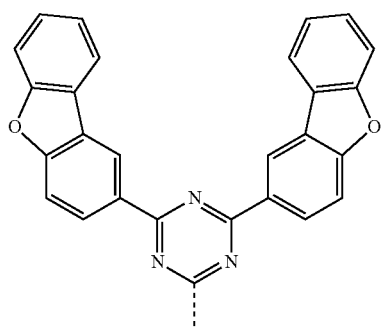

formula (E-31)
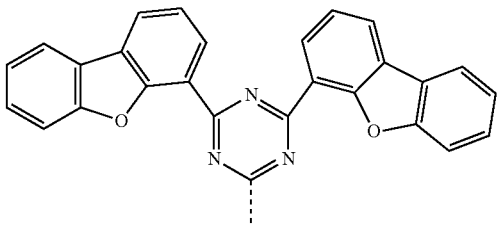

formula (E-32)
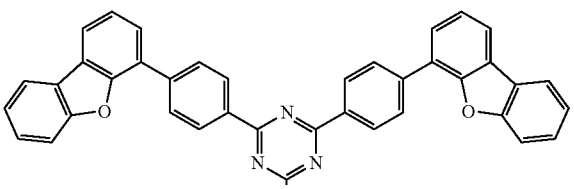

formula (E-33)
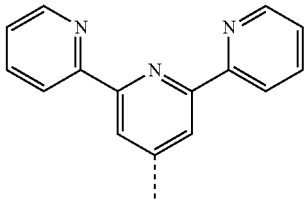

formula (E-34)
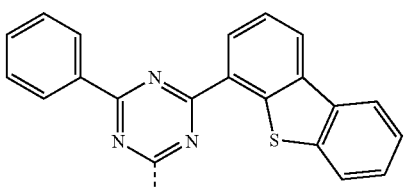

formula (E-35)
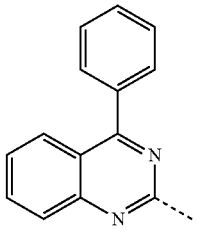

According to a further embodiment, the electron-transporting group E may contain at least one strongly electron-attracting group, which is preferably bonded to an aryl or heteroaryl group.

The strongly electron-attracting group here can preferably be selected from the structures (E-36), (E-37) and (E-38)

(E-36)

(E-37)
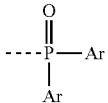

-continued

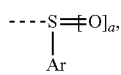

(E-38)

in which

Ar is in each case identical or different and has the meaning given above;

a is 1 or 2, preferably 2; and the dashed line represents the bond to the spirobifluorene skeleton or, if p=1, optionally to the group Ar, where this group Ar is bonded to the spirobifluorene skeleton.

In this case, a compound according to the invention may contain merely electron-deficient heteroaromatic groups or aryl or heteroaryl groups with at least one strongly electron-attracting group as electron-transporting group. If the compound according to the invention contains two or more electron-transporting groups, the compound can contain both at least one electron-deficient heteroaromatic group and also at least one aryl or heteroaryl group with at least one strongly electron-attracting group.

In particular, the compounds according to the invention have a triplet T1 level which is significantly higher compared with compounds of the prior art, where this is advantageous for the construction of green and in particular blue phosphorescent OLEDs. This advantage is particularly essential for the use of the materials as triplet matrix material (TMM), hole-blocking material (HBM) and electron-transport material (ETM). The T1 level of TMM, EBH, ETM in the emitting layer and the adjacent layers (EBM/ETM) should be greater than or equal to that of the emitting material in order to prevent quenching of the emission.

The spiro compounds according to the invention, containing structures of the formula (I), may also be chiral, depending on the structure. This is the case, in particular, if they contain substituents, for example alkyl, alkoxy or aralkyl groups, which have one or more stereo centres. Since the basic structure of the boron-containing compound may also be a chiral structure, the formation of diastereomers and a plurality of enantiomer pairs is possible. The compounds according to the invention then include both the mixtures of the various diastereomers or the corresponding racemates and also the individual isolated diastereomers or enantiomers.

The compound can preferably be in the form of an enantiomer mixture, particularly preferably a diastereomer mixture. This enables the properties of electronic devices which are obtainable using the compounds according to the invention to be enhanced unexpectedly. These properties include, in particular, the lifetime of the devices.

Particularly preferred compounds include structures of the following formulae 1 to 141:

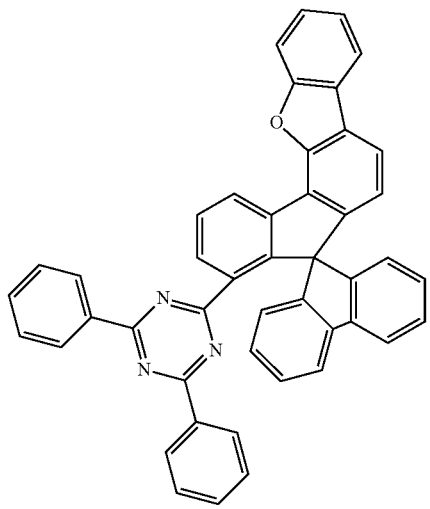

1

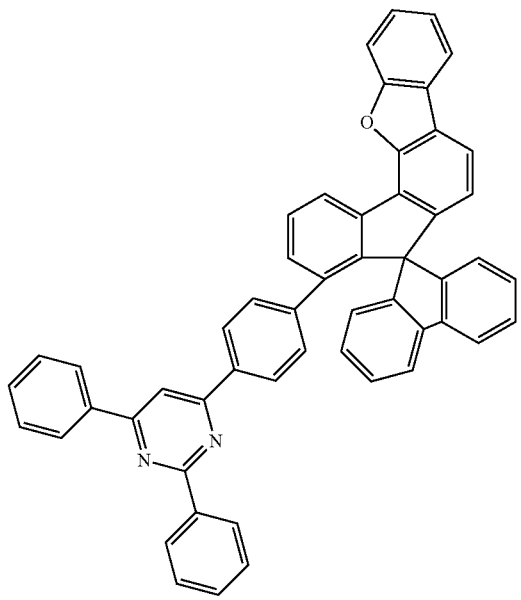

2

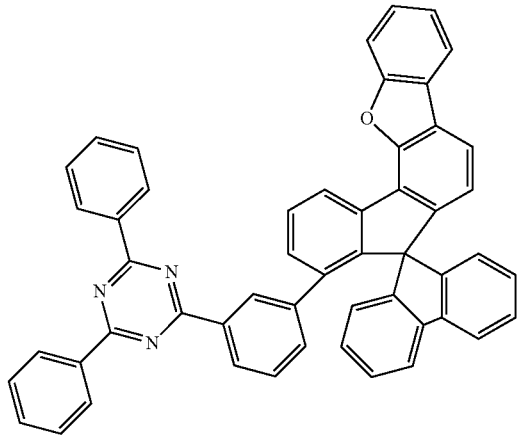

3

4
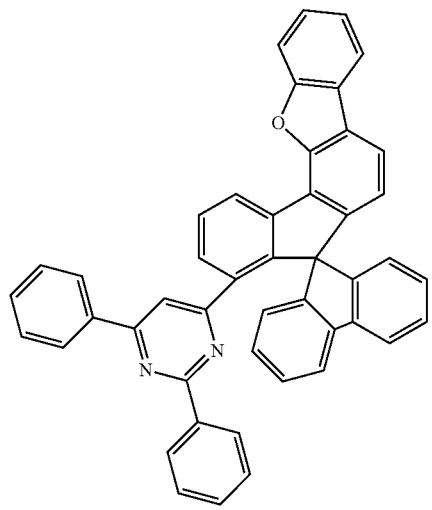
5
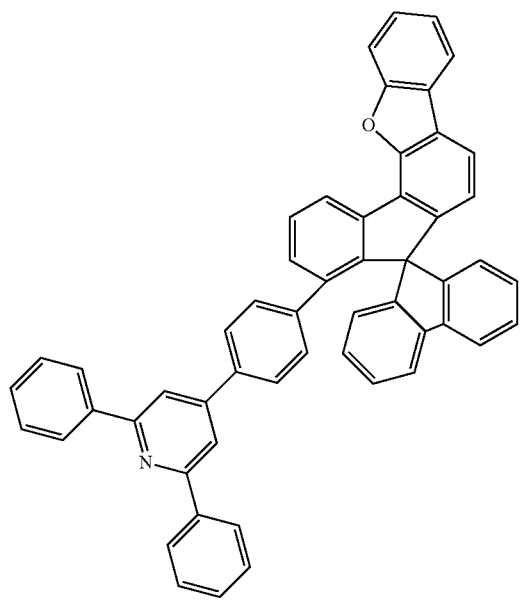
6
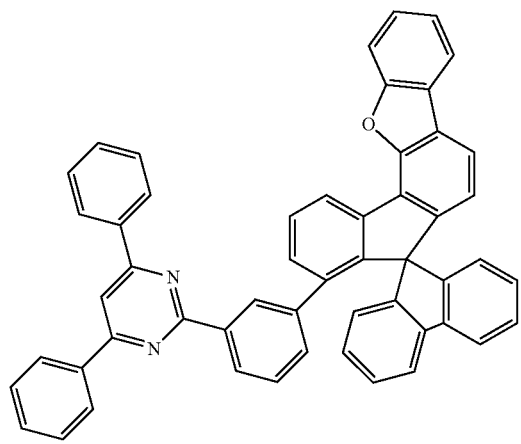
7
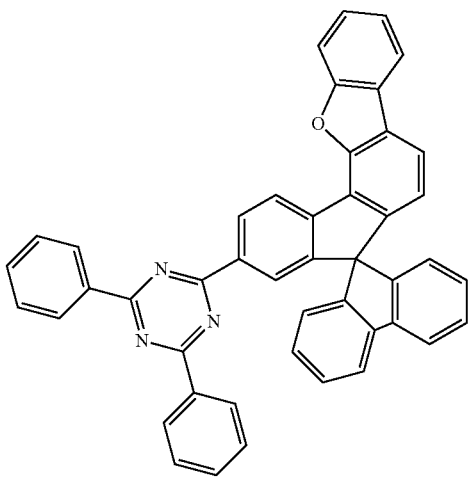
8
9

-continued
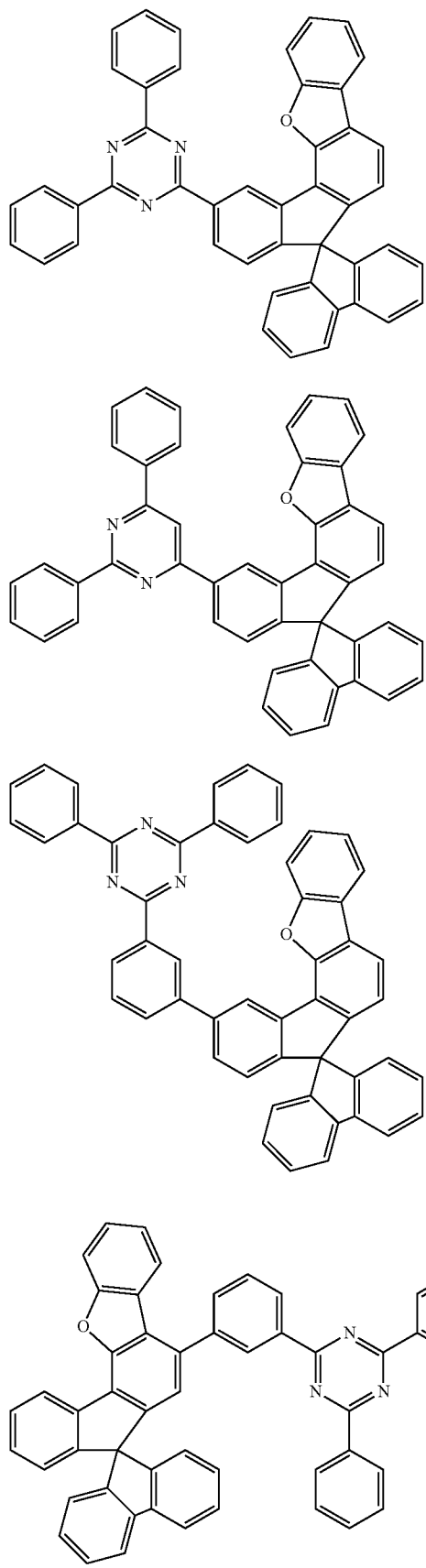
-continued
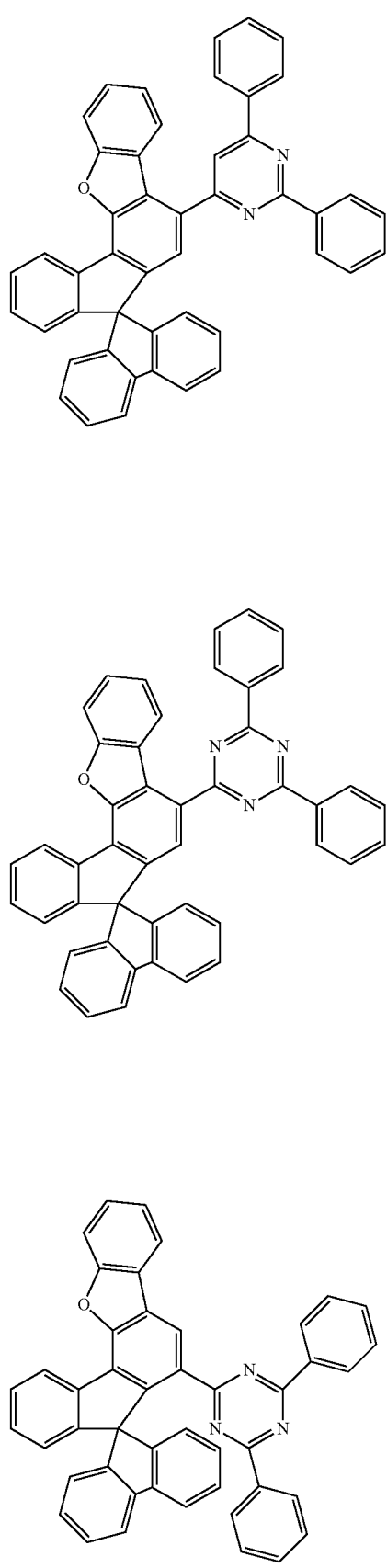

-continued
17
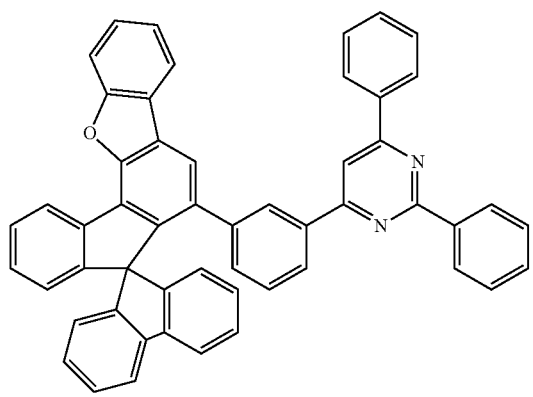
18
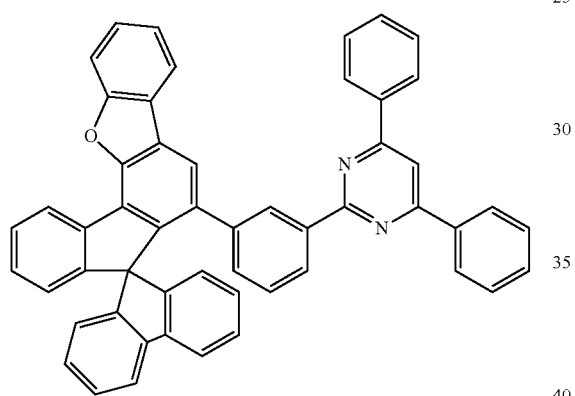
19
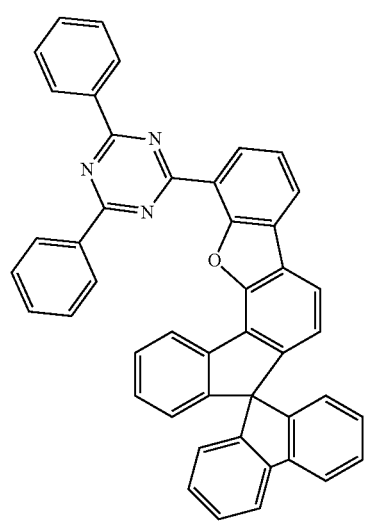
-continued
20
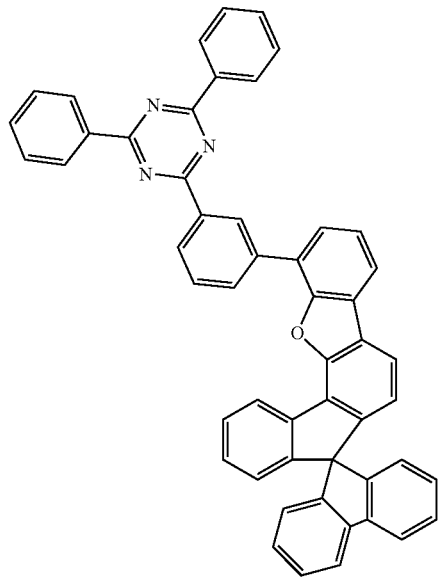
21
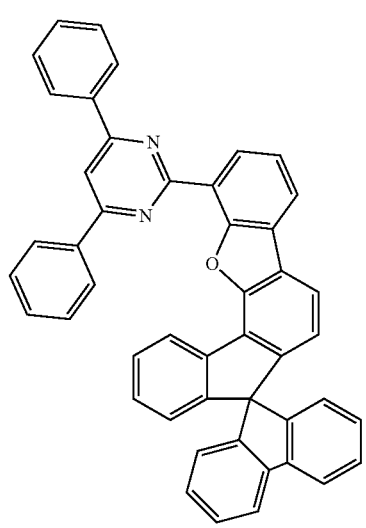
22
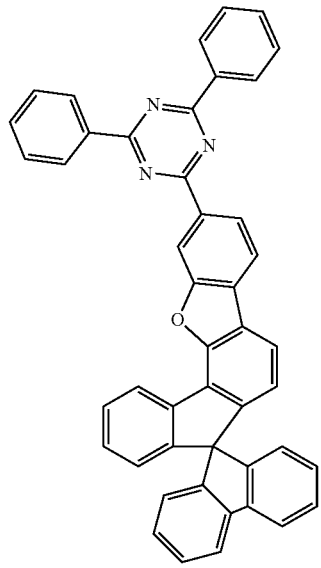

23
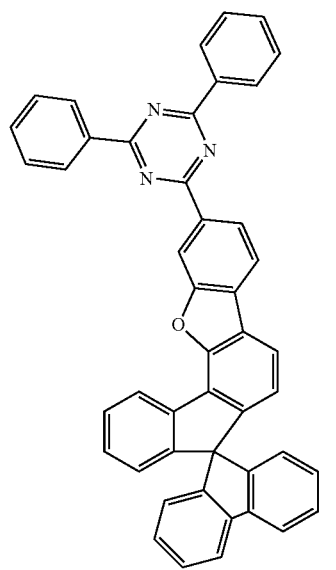
25
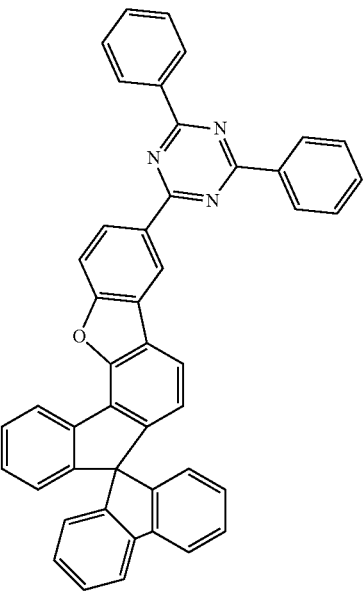
24
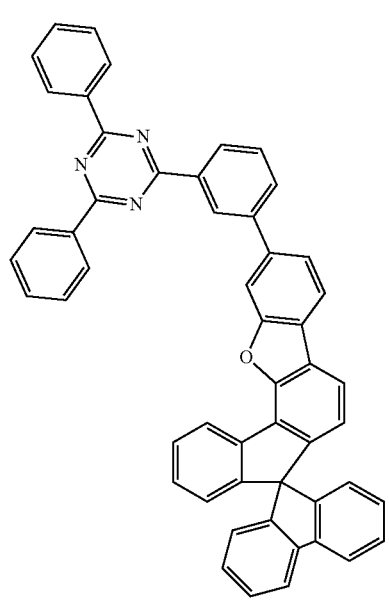
26
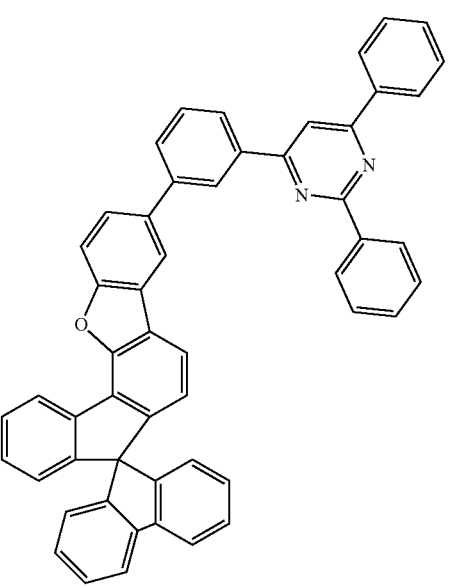

27
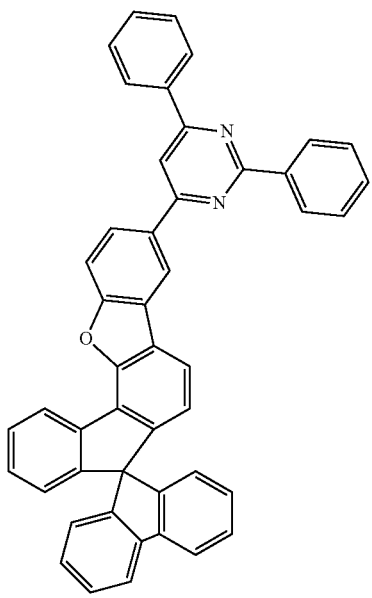
28
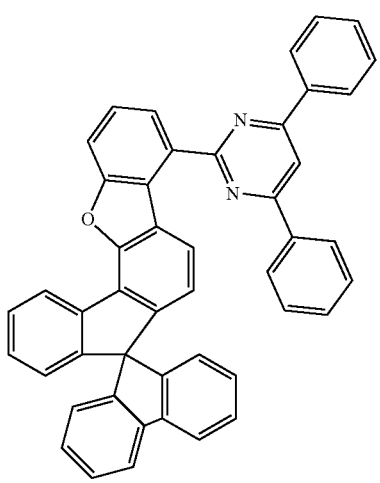
29
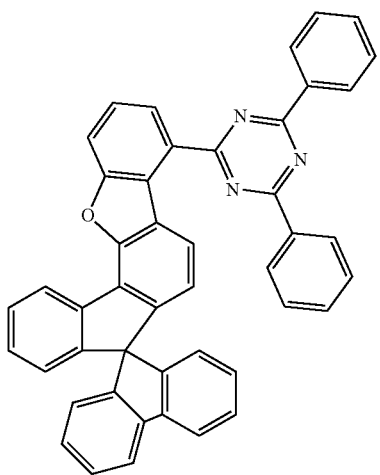
30
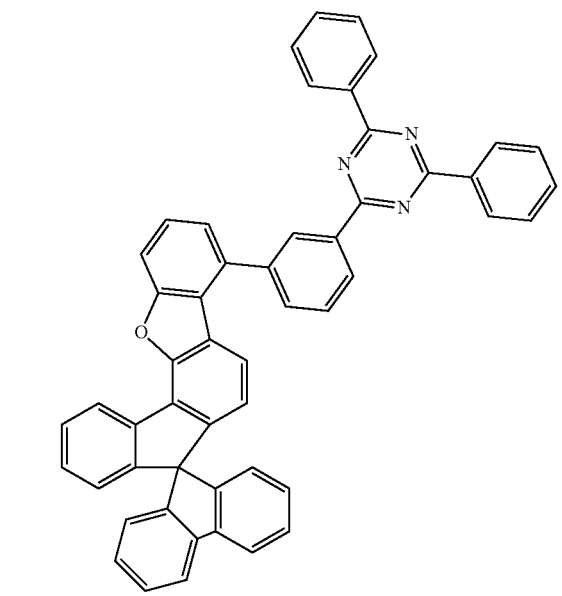
31
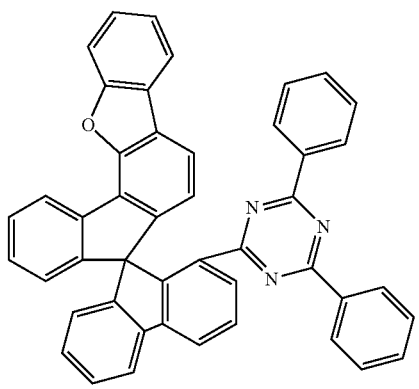
32
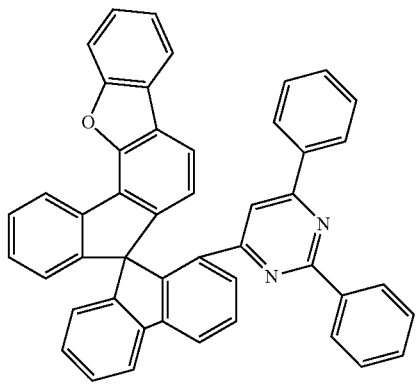

33
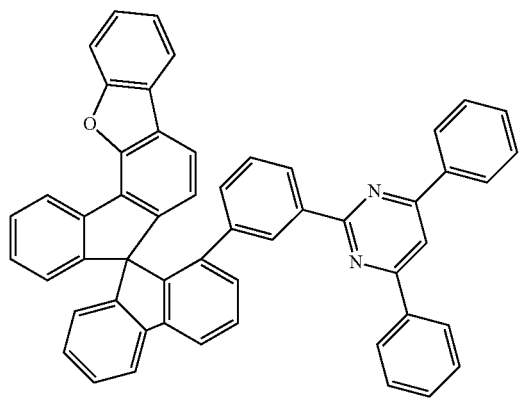
34
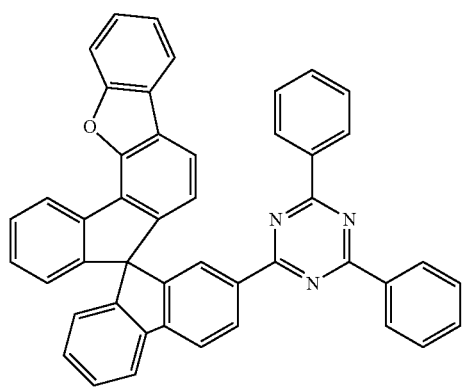
35
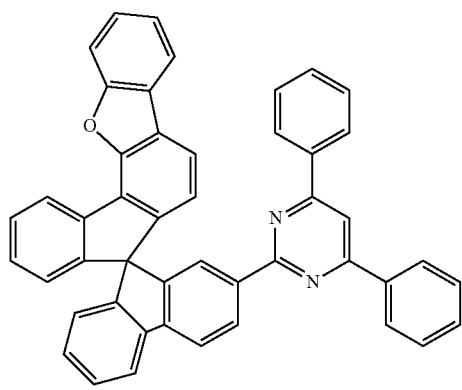
36
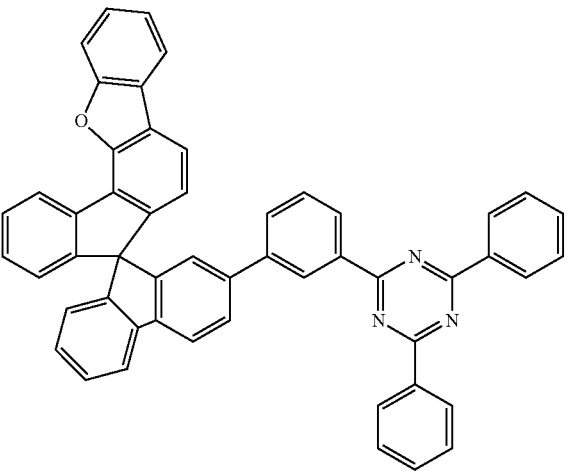
37
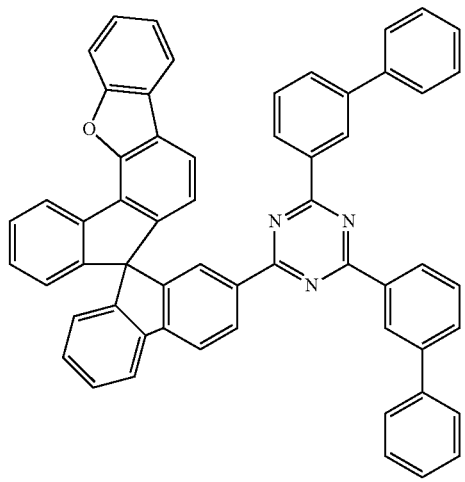
38
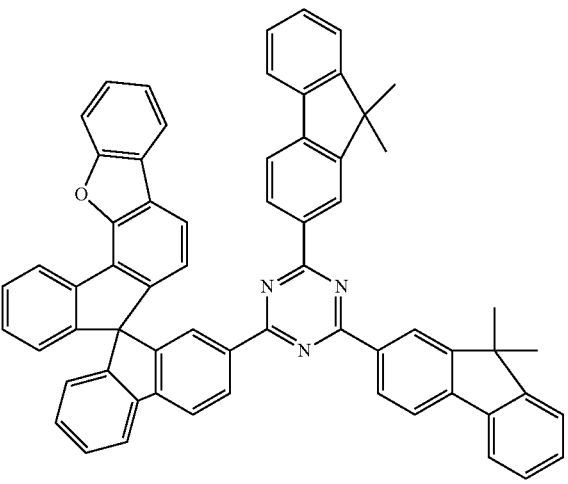

39
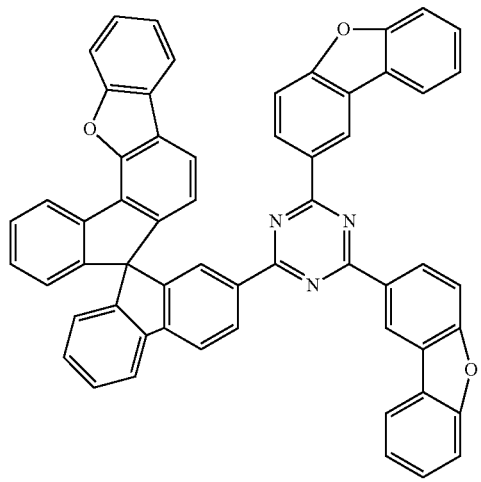
40
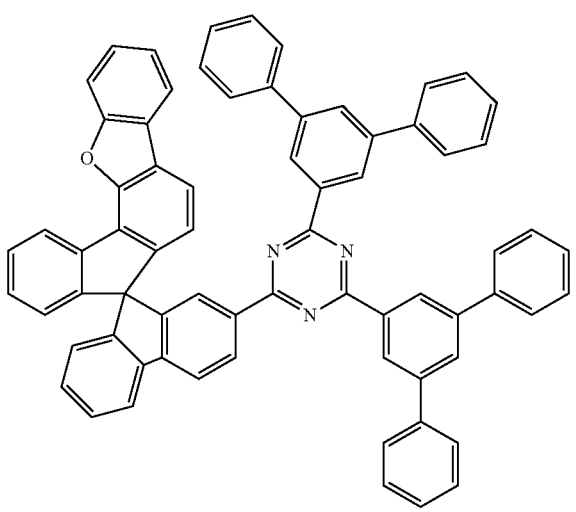
41
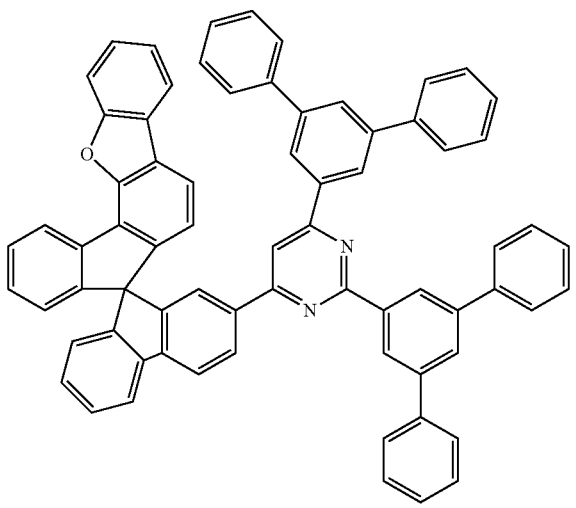
42
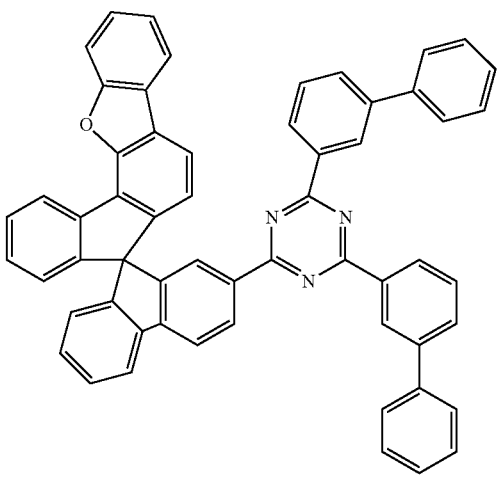
43
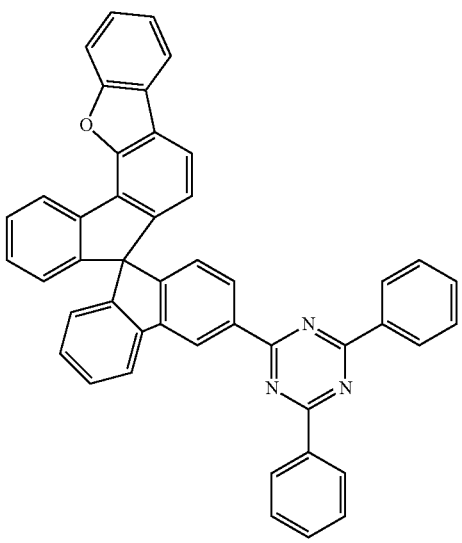
44
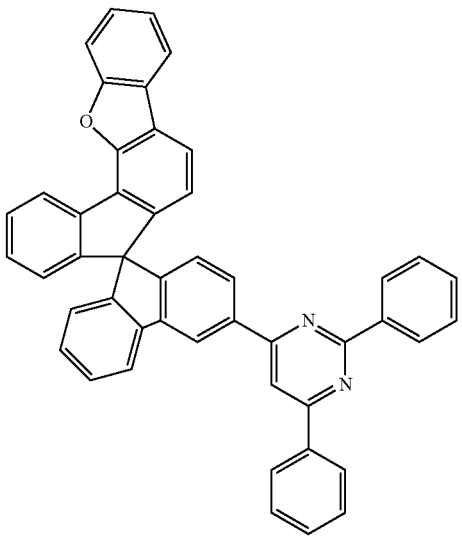

45
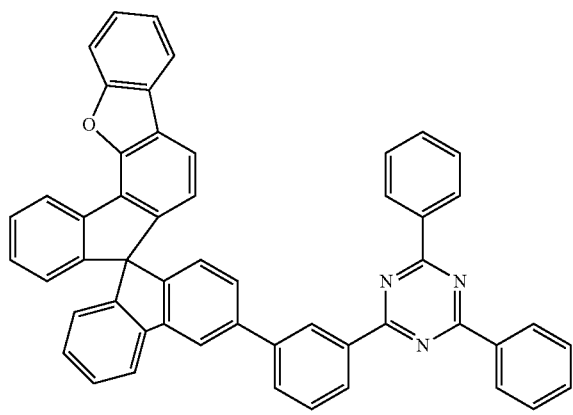
46
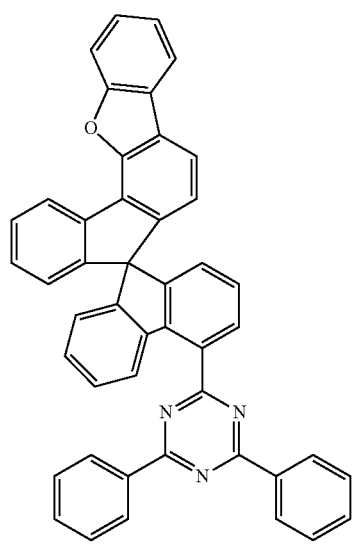
47
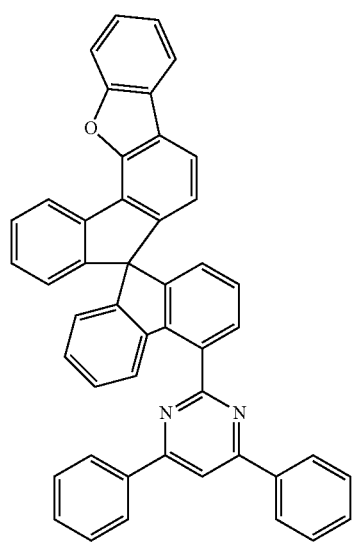
48
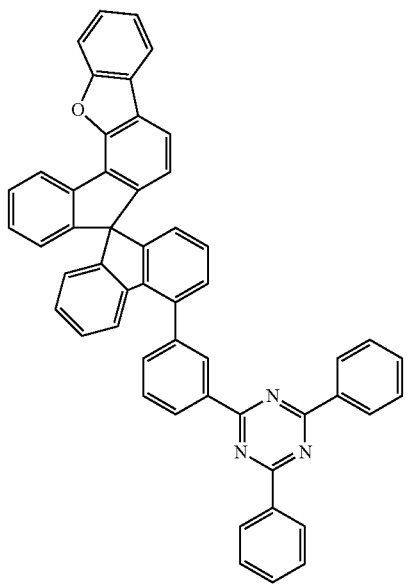
49
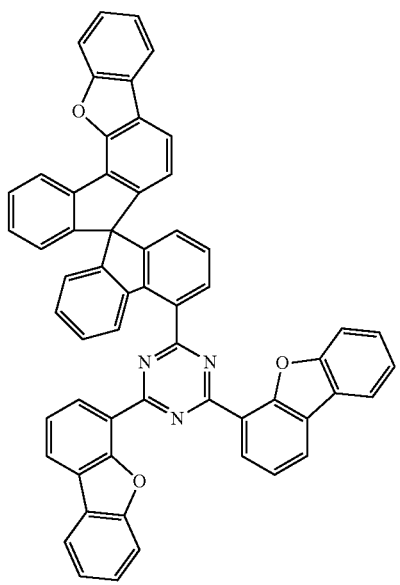

50
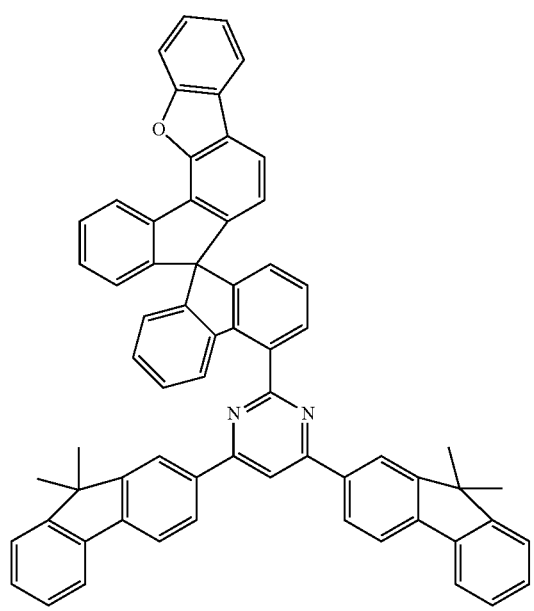
52
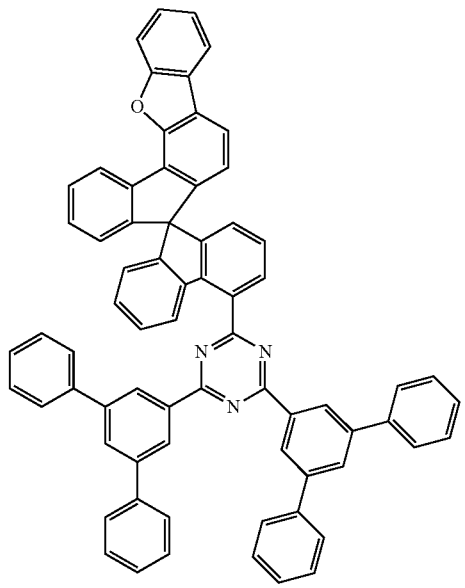
51
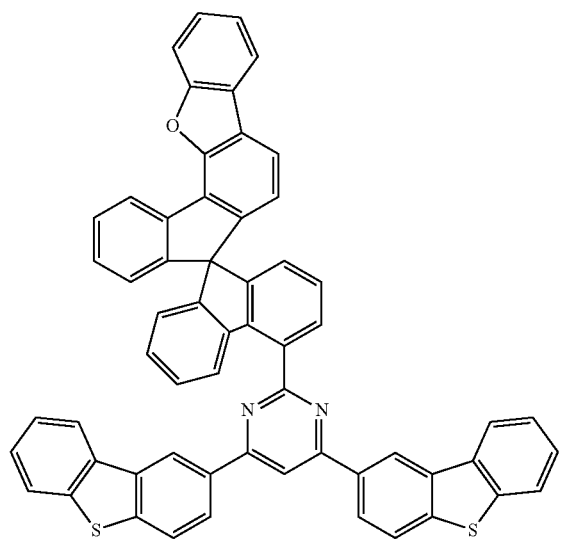
53
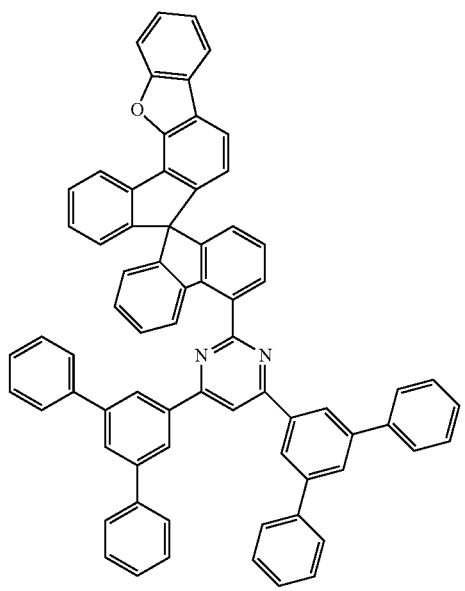

54
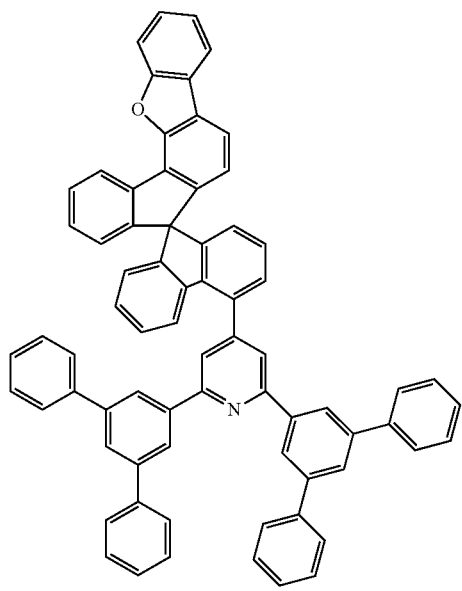
55
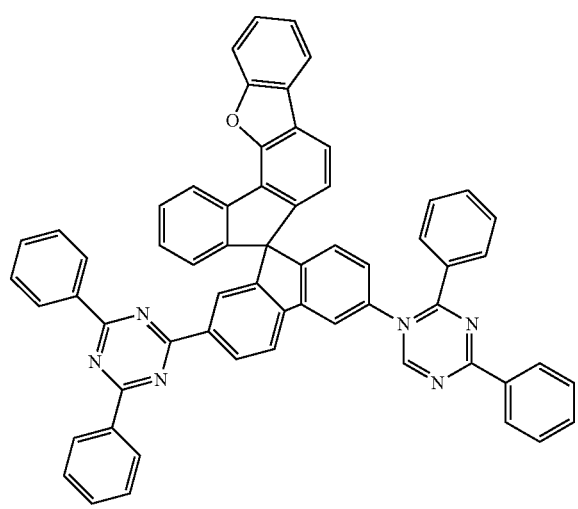
56
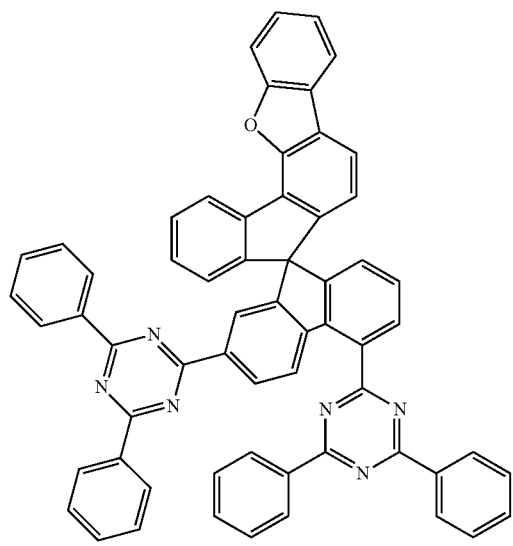
57
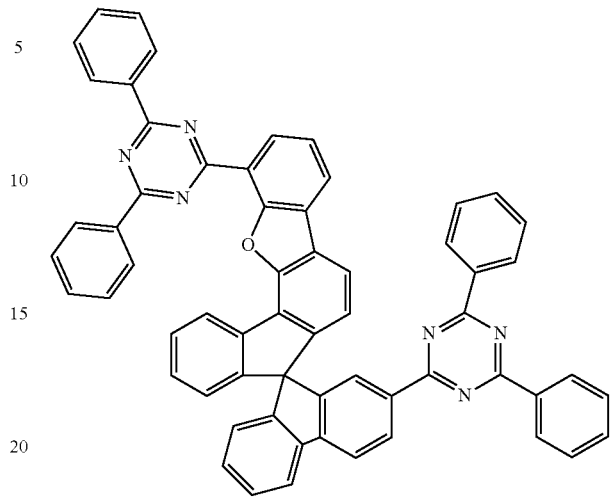
58
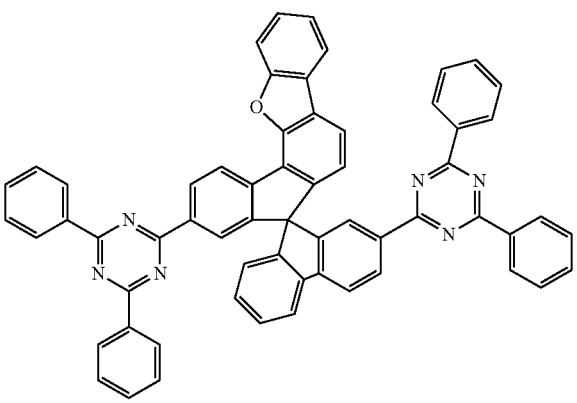
59
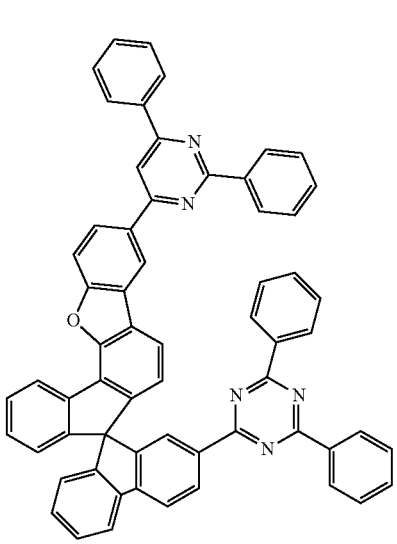

60
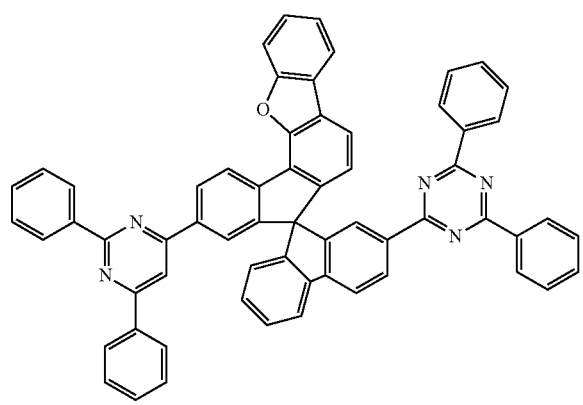
61
63
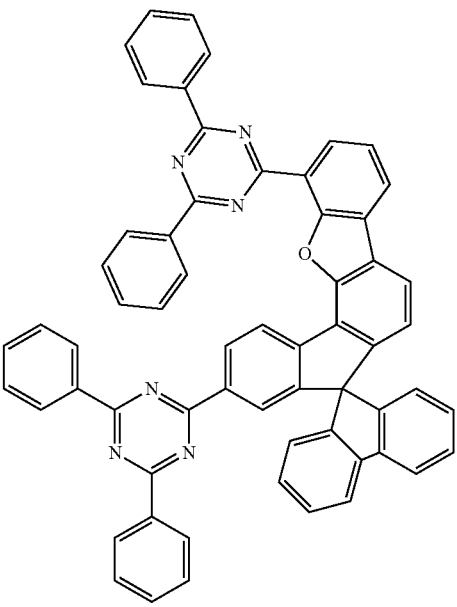
62
64
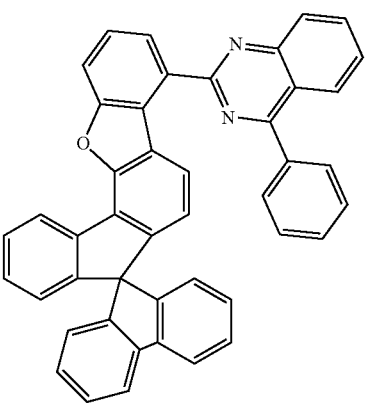
65
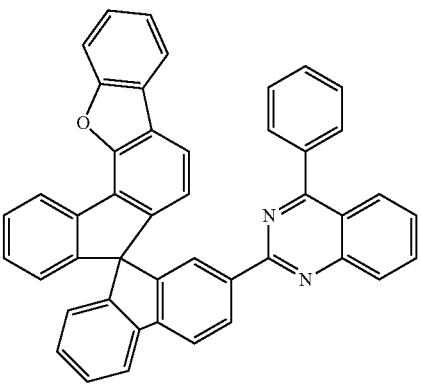

41
-continued
66
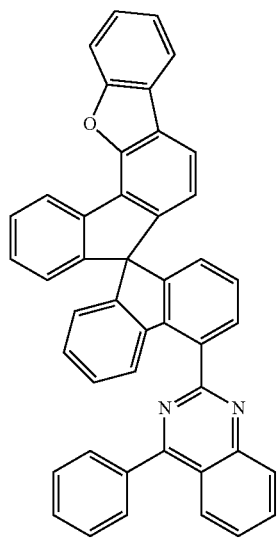
67
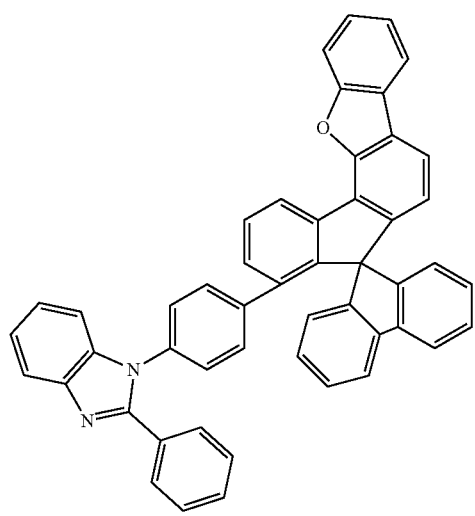
68
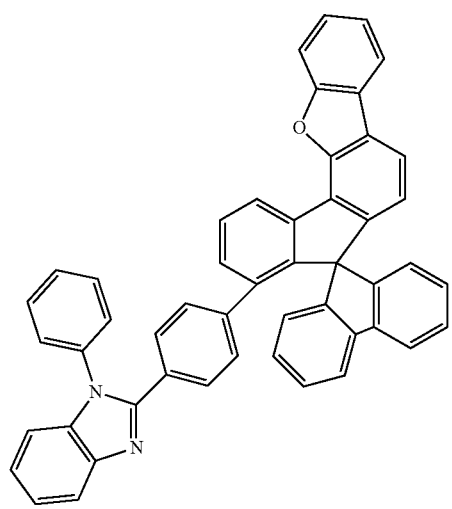
42
-continued
69
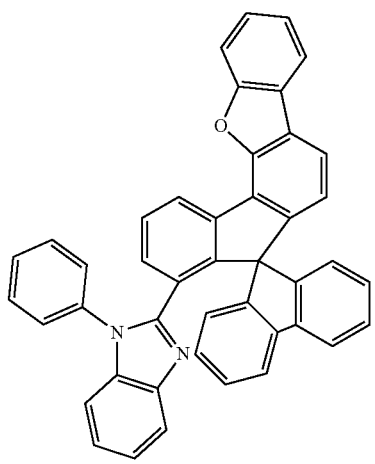
70
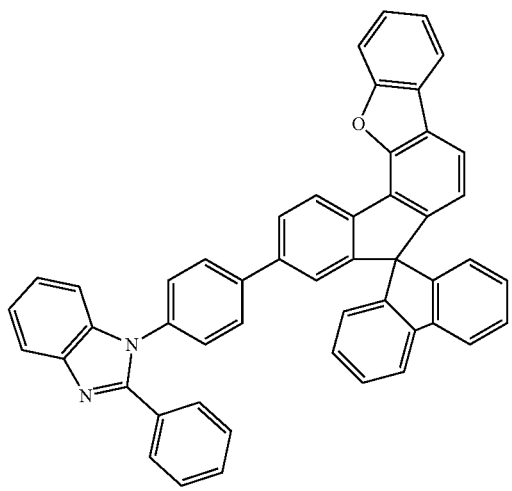
71
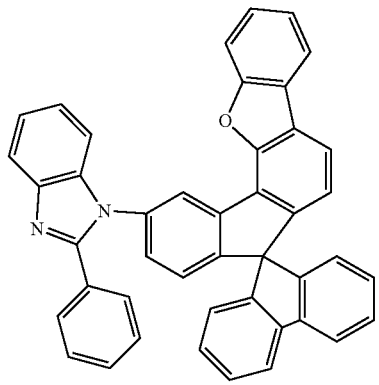

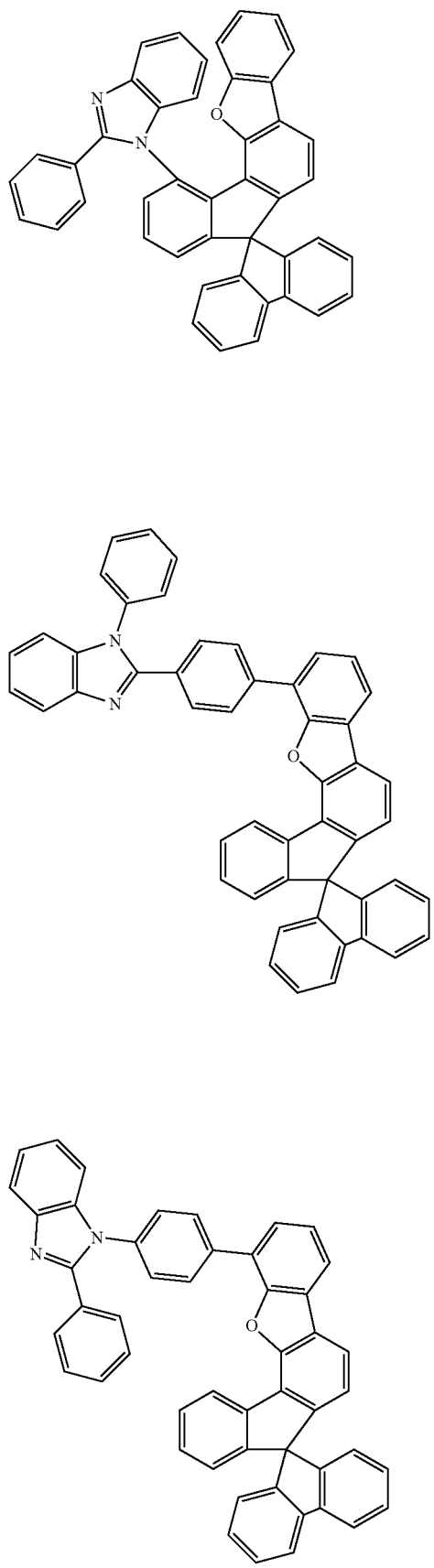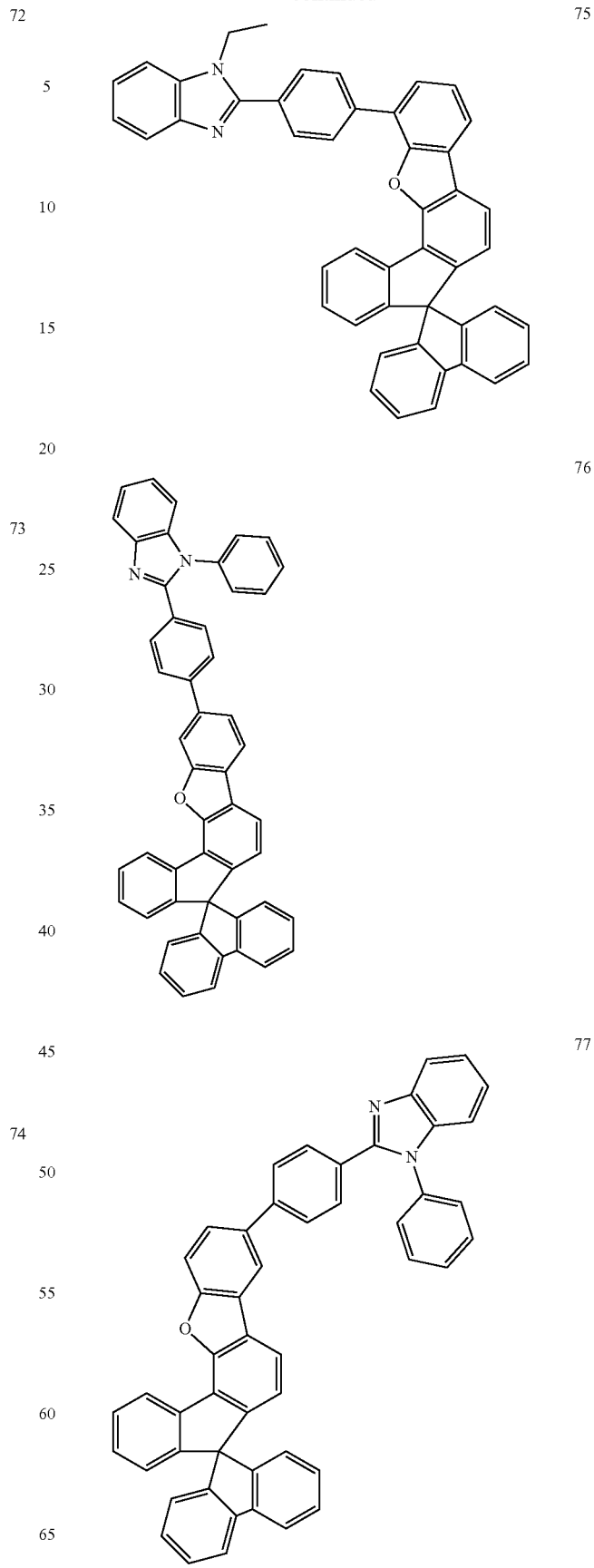

-continued
78
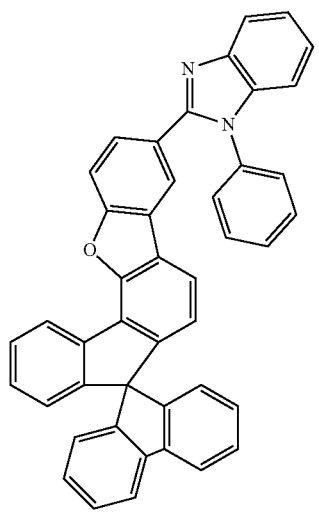
79
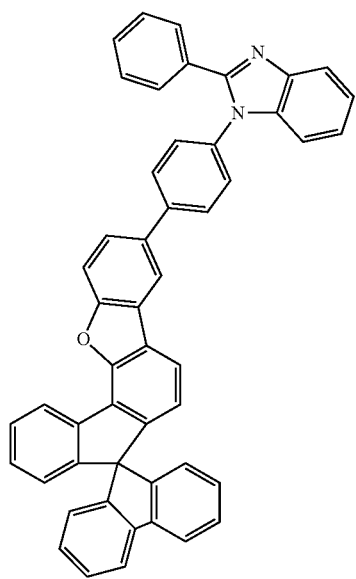
80
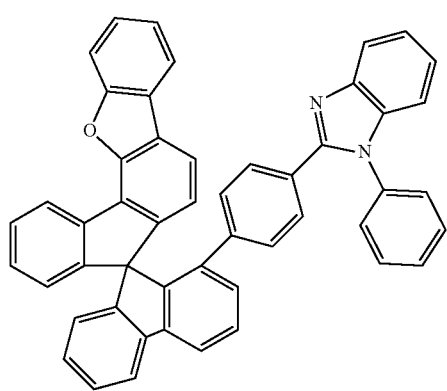
-continued
81
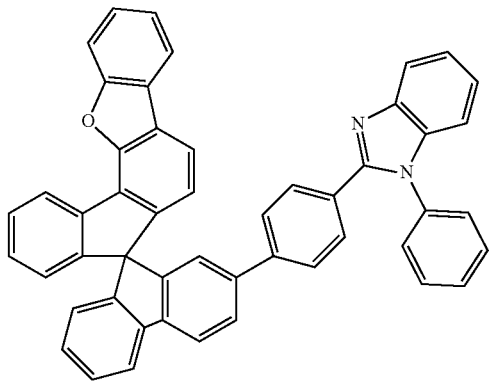
82
83
84

85
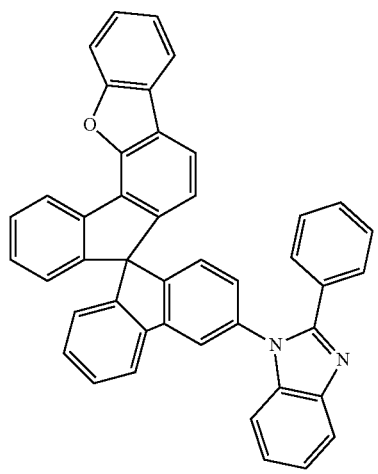
86
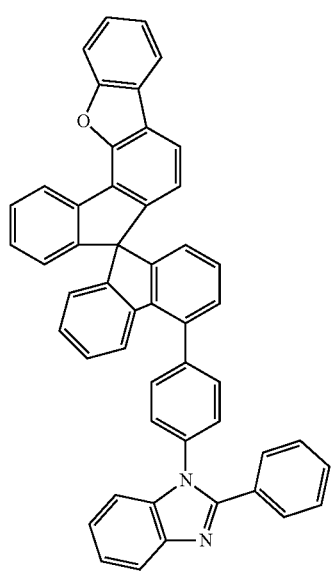
87
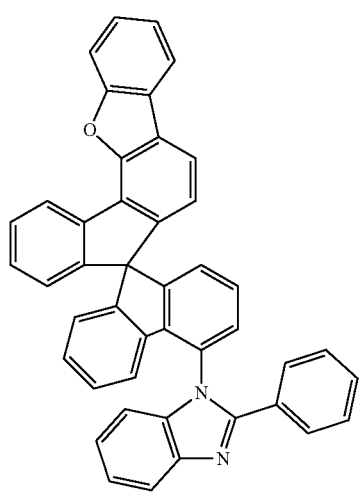
88
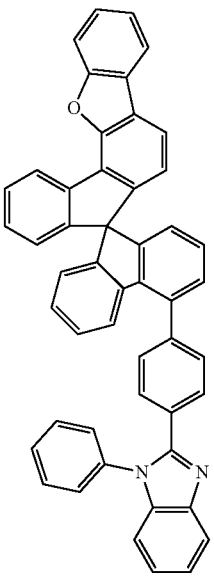
89

90
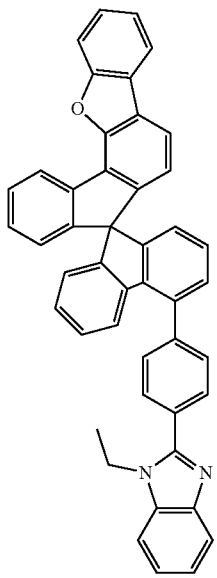
91
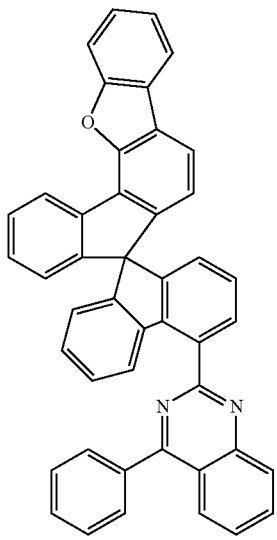
92
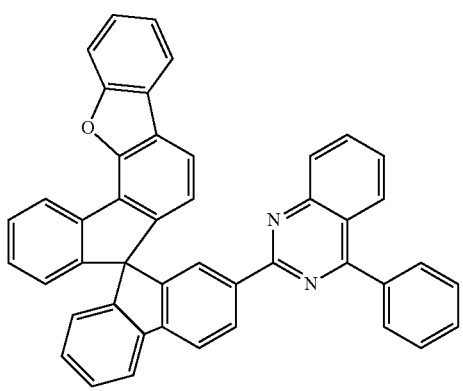
93
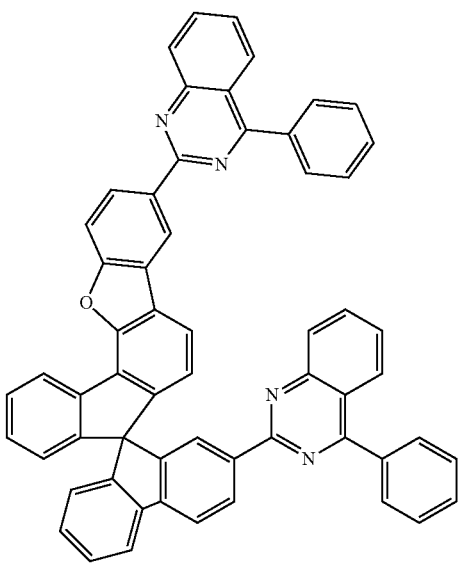
94
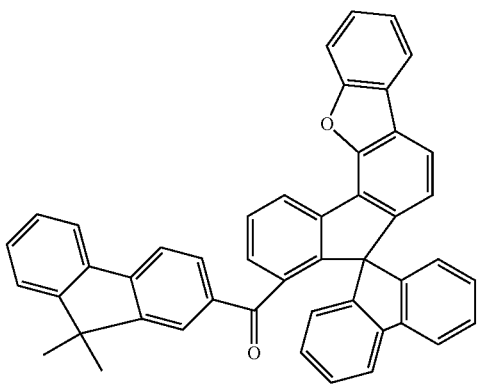
95
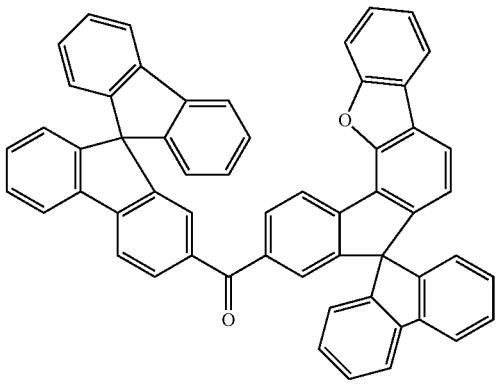

96
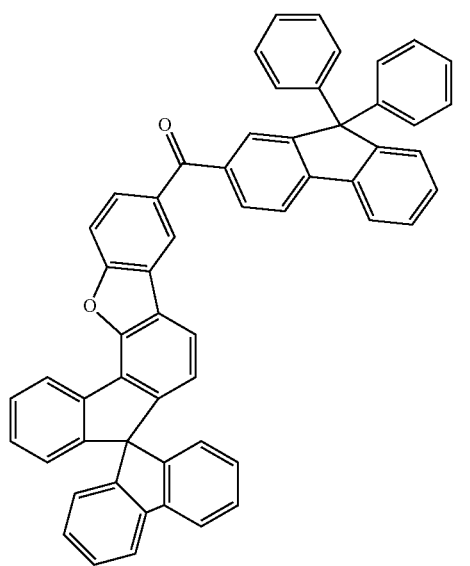
97
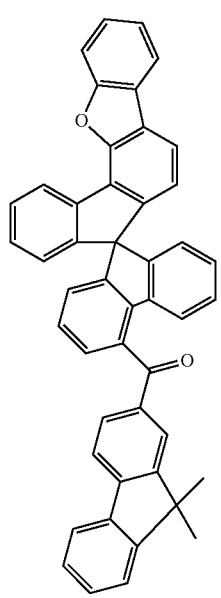
98
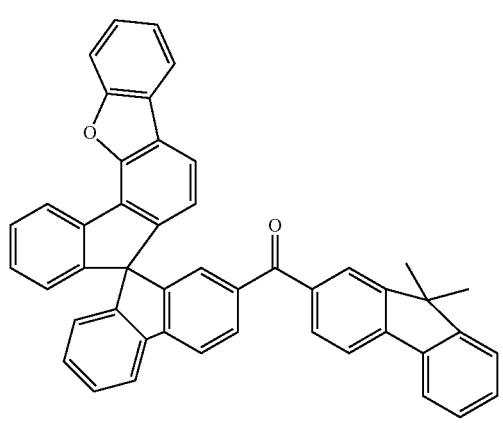
99
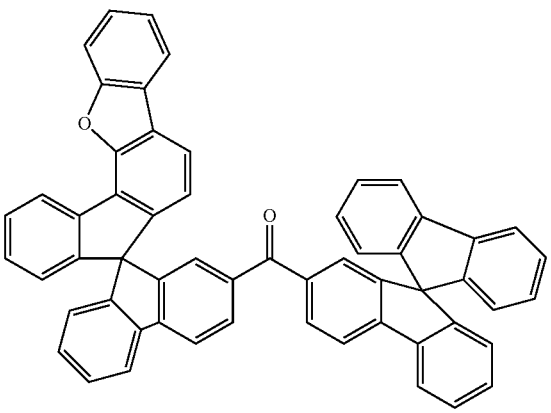
100
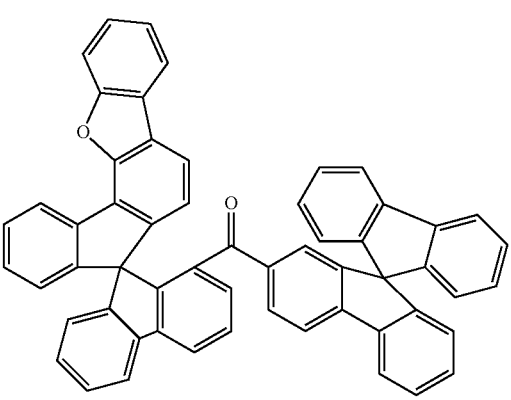
101
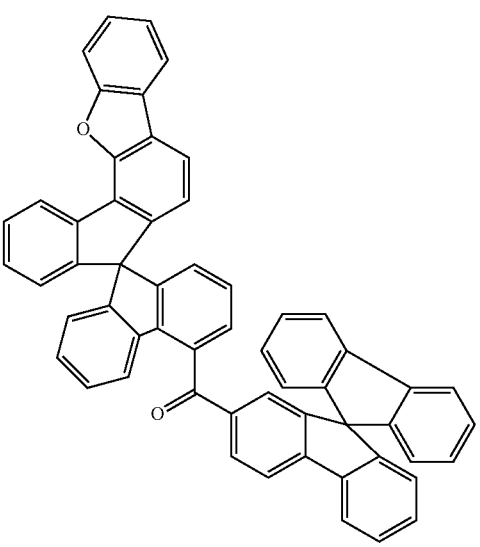

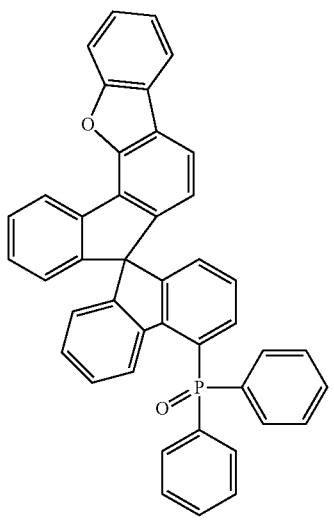
102
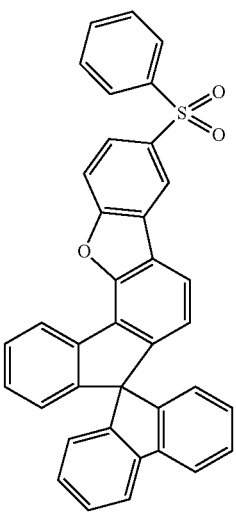
105
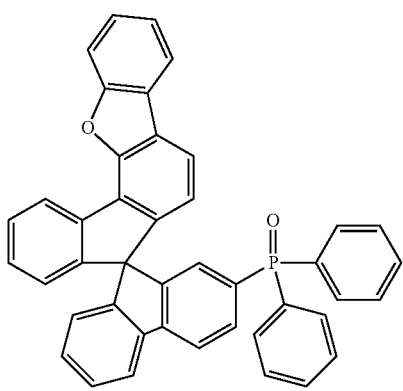
103
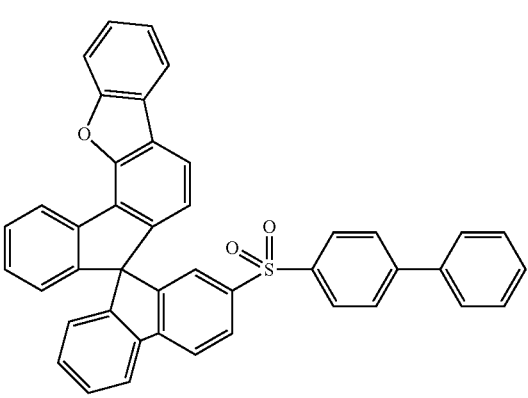
106
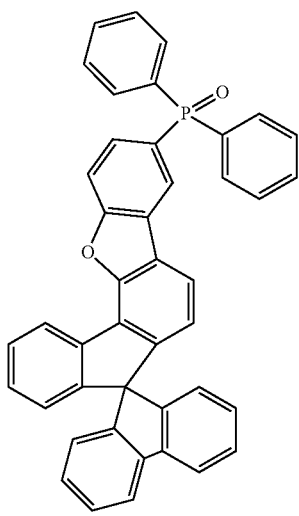
104
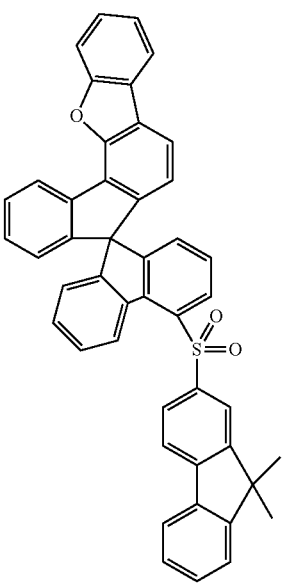
107

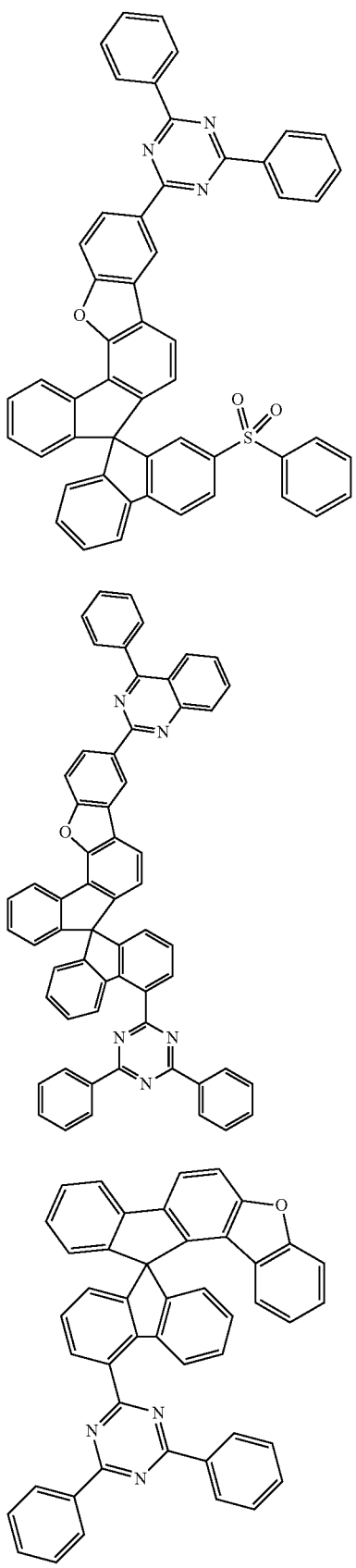
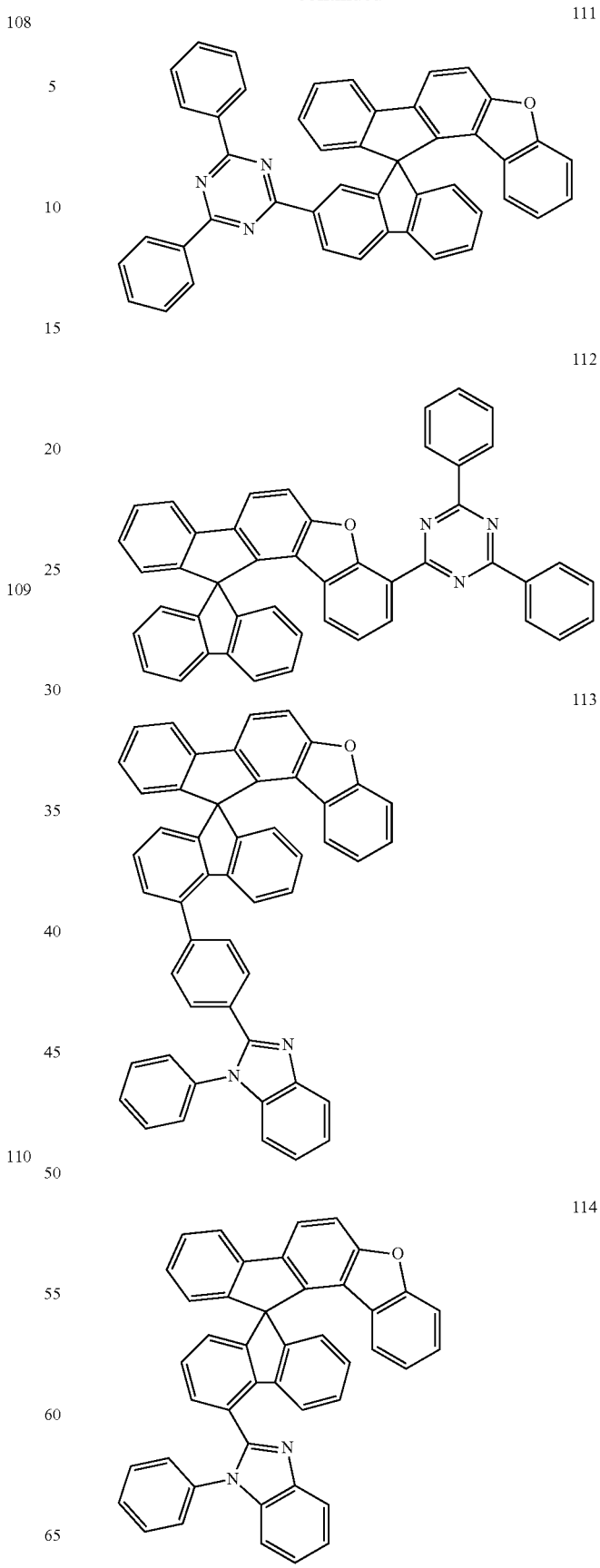

115
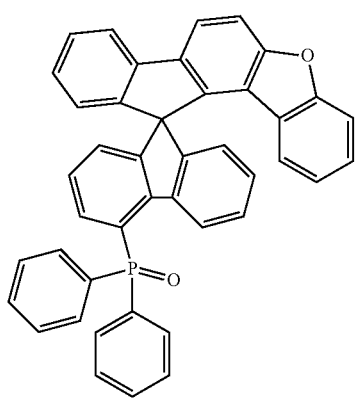
116
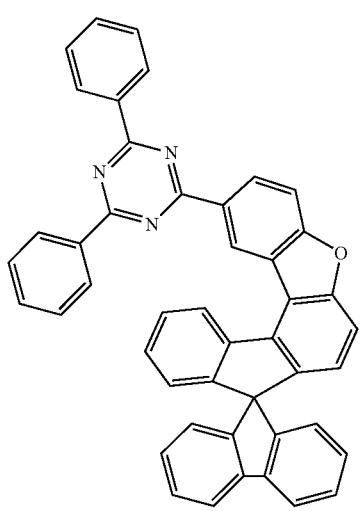
117
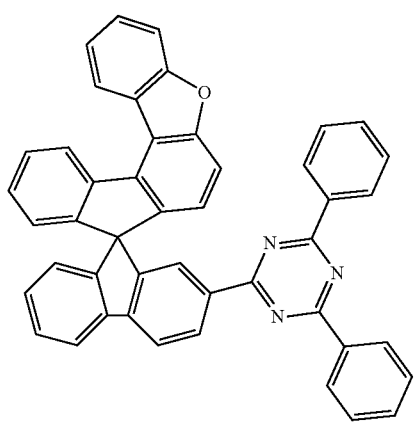
118
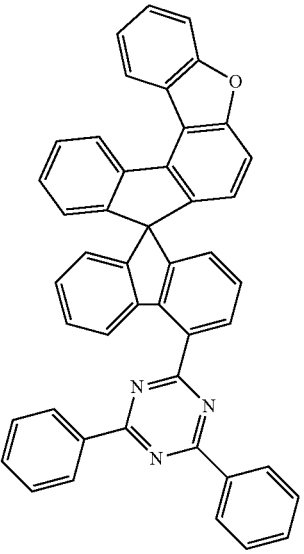
119
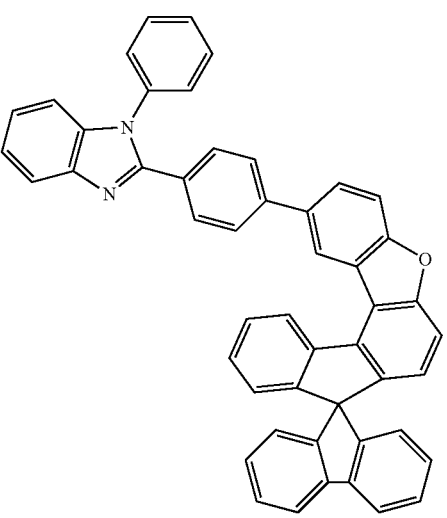
120
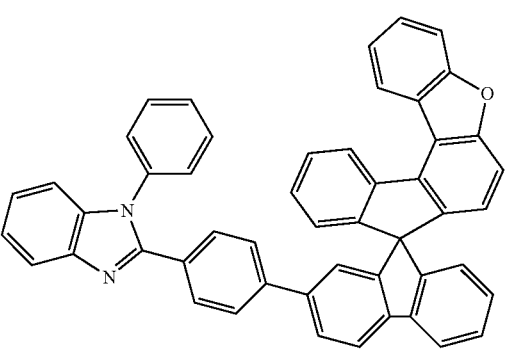

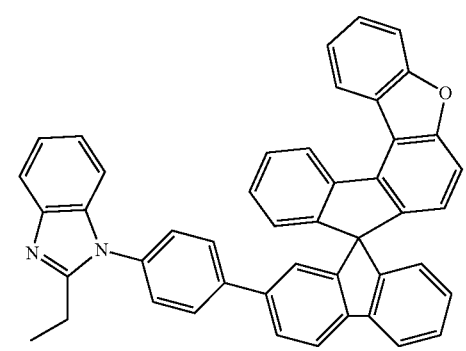
121
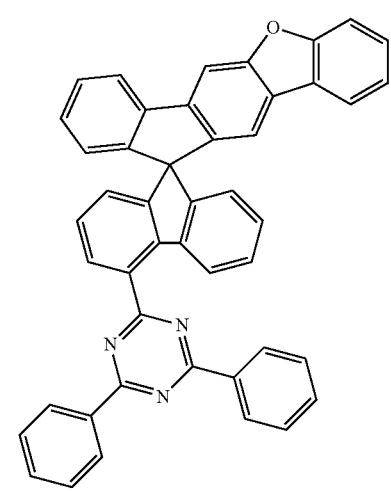
122
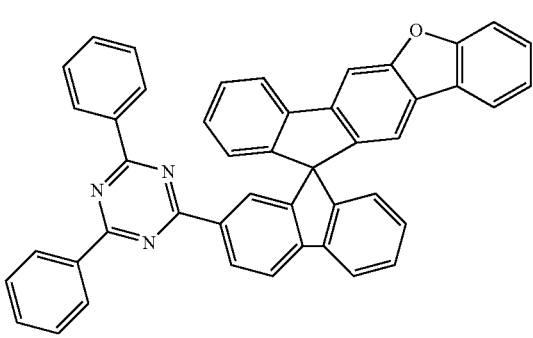
123
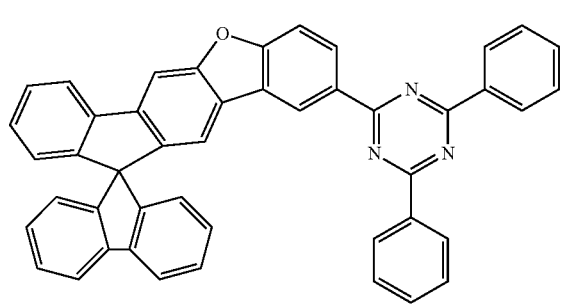
124
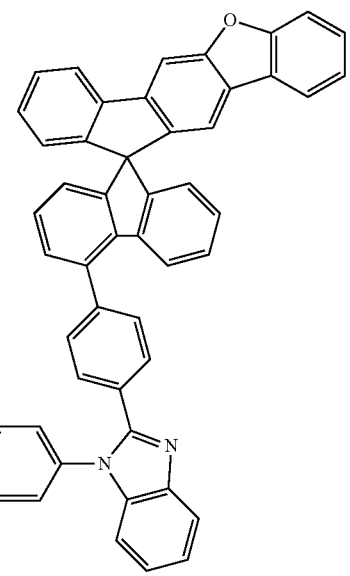
125
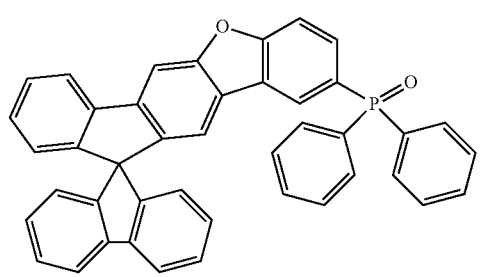
126
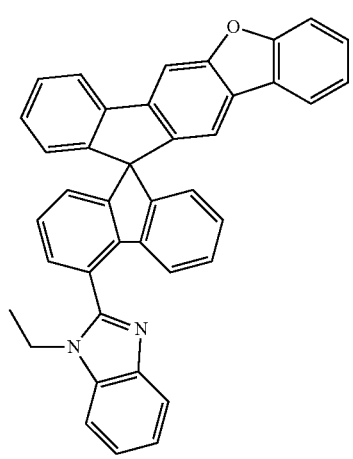
127

128
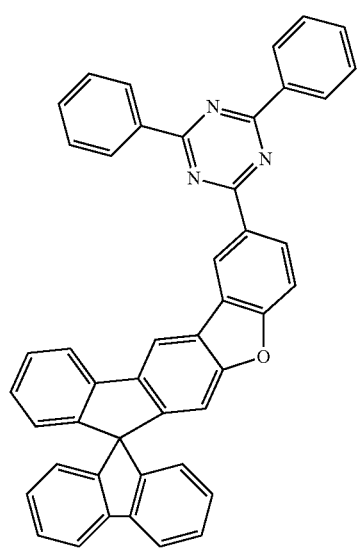
129
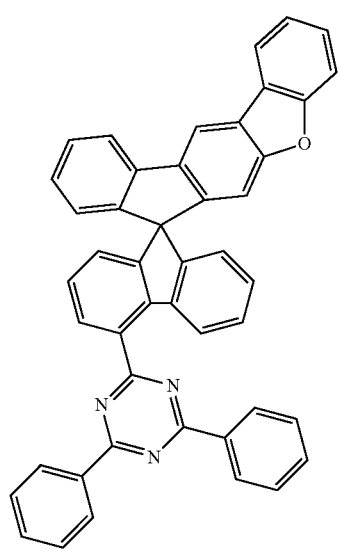
130
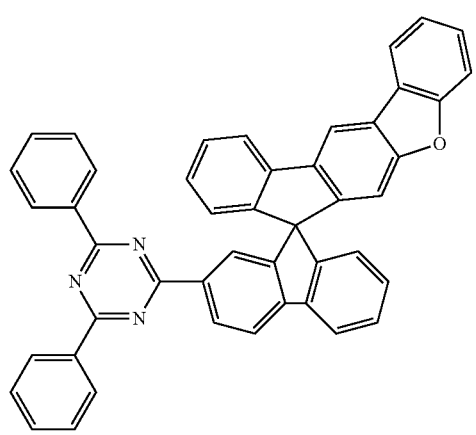
131
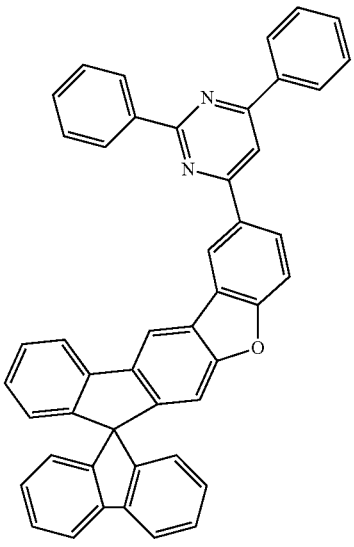
132
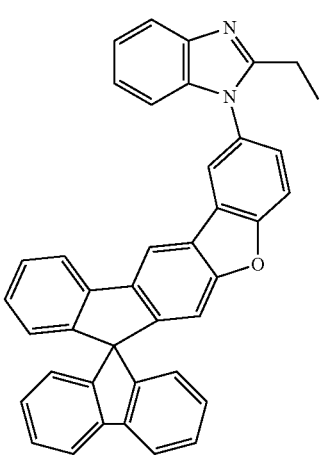
133
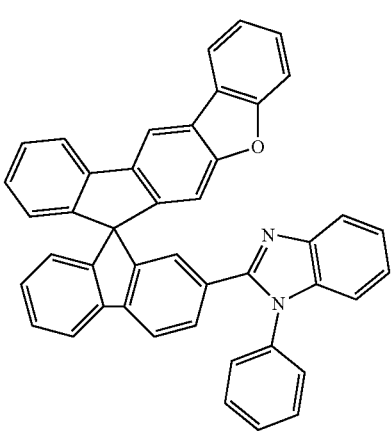

134
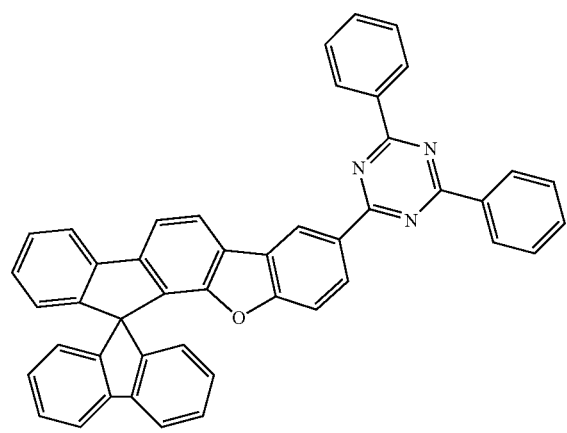
135
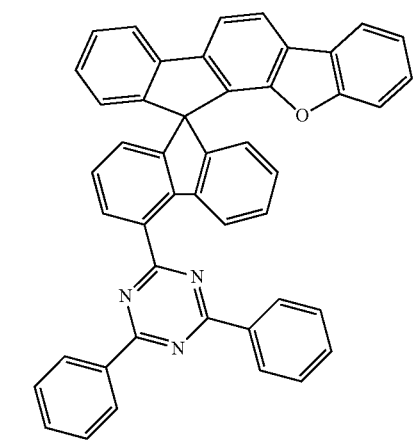
136
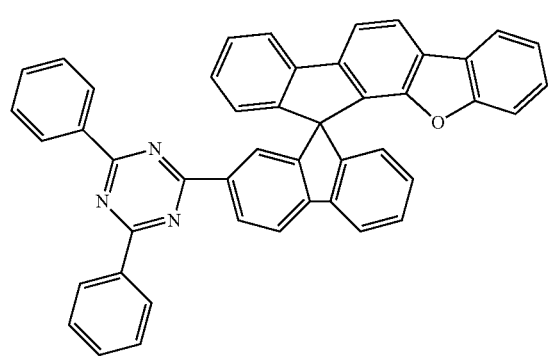
137
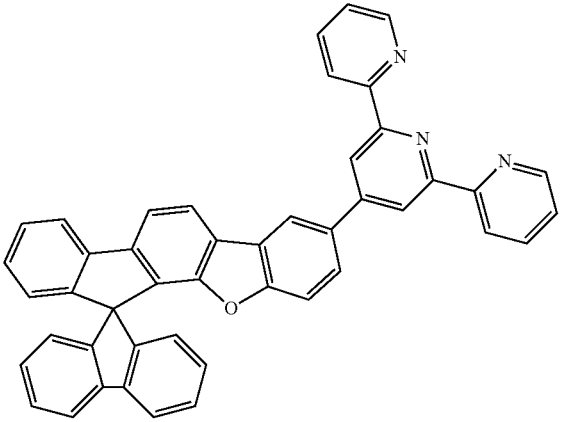
138
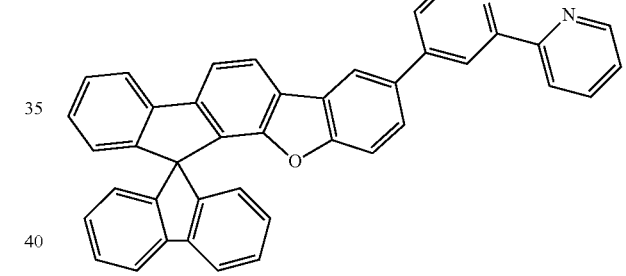
139
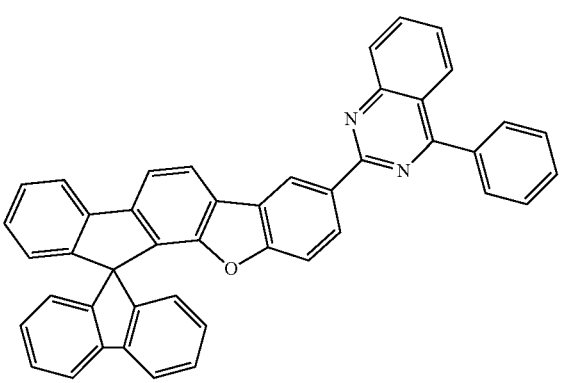

140

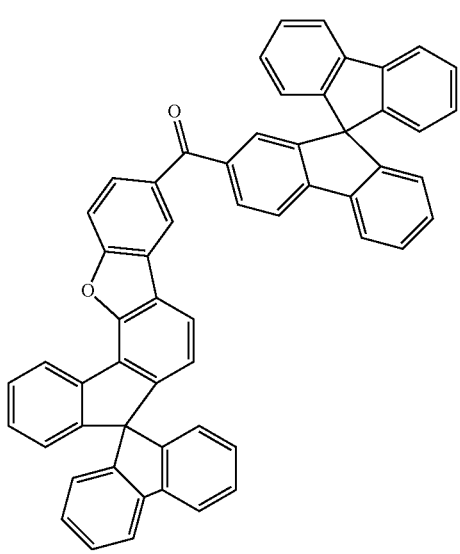

141

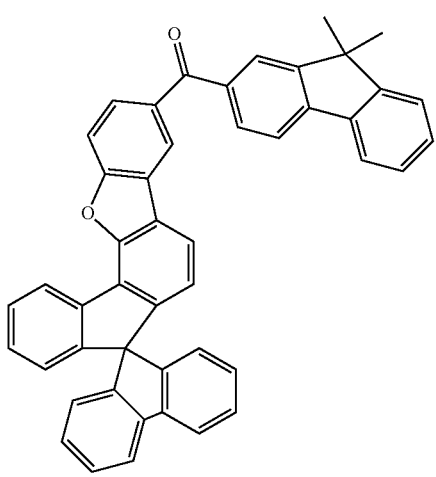

Under the prerequisite that the conditions indicated in Claim 1 are observed, the preferred embodiments mentioned above can be combined with one another as desired. In a particularly preferred embodiment of the invention, the preferred embodiments mentioned above apply simultaneously.

The compounds according to the invention can in principle be prepared by various processes. However, the processes described below have proven particularly suitable.

The present invention therefore furthermore relates to a process for the preparation of compounds containing structures of the formula (I) in which firstly the spirobifluorene skeleton is prepared, and, in a later step, a radical containing an electron-transporting group is introduced via a coupling reaction.

Particularly suitable and preferred coupling reactions, all of which result in C—C links and/or C—N links, are the BUCHWALD, SUZUKI, YAMAMOTO, STILLE, HECK, NEGISHI, SONOGASHIRA and HIYAMA coupling reactions.

In all the following synthesis schemes, the compounds are, for simplification of the structures, shown with a small number of substituents. This does not exclude the presence of any desired further substituents in the processes.

The six isomers of the spiro skeleton A to F, which are shown below for the preferred spiro compounds containing a dibenzofuran group, can be obtained in accordance with Schemes 1-8.

A

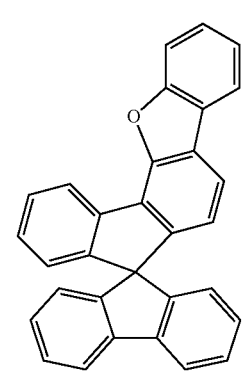

B

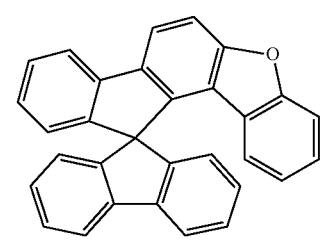

C

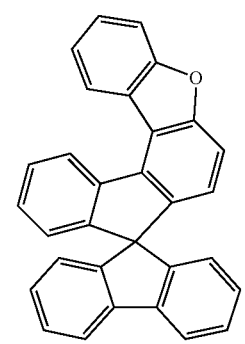

D

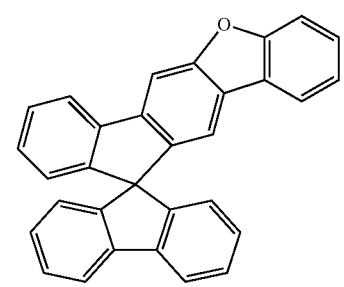

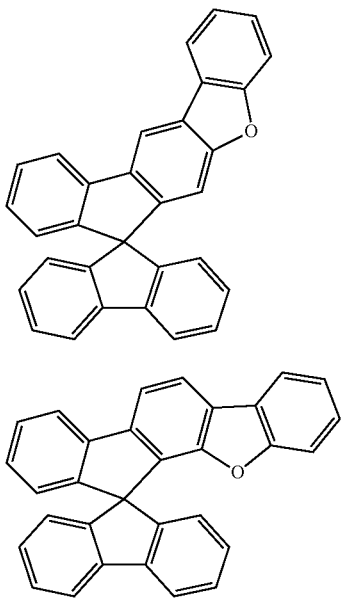

The corresponding halogenated spirobenzofluorene derivatives of type A, preferably the spirobenzofluorenofuran or -thiophene derivatives, can be prepared starting from dibenzothiophene- or dibenzofuranboronic acid derivatives by Suzuki coupling and subsequent lithiation and reaction with fluorenone derivatives, as shown by way of example in Scheme 1.

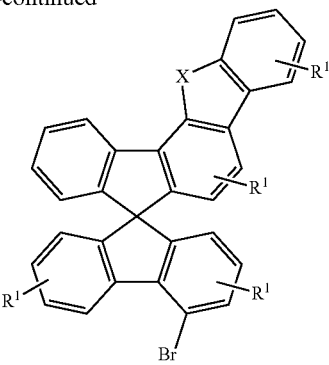

The halogenated spirobenzofluorenofuran or -thiophene of type B can be prepared starting from halogenated mercaptofluorenone derivatives or hydroxyfluorenone derivatives by Suzuki coupling and subsequent cyclisation and further reaction with monolithiated 2,2'-dibromobiphenyl derivatives and further cyclisation (Scheme 2).

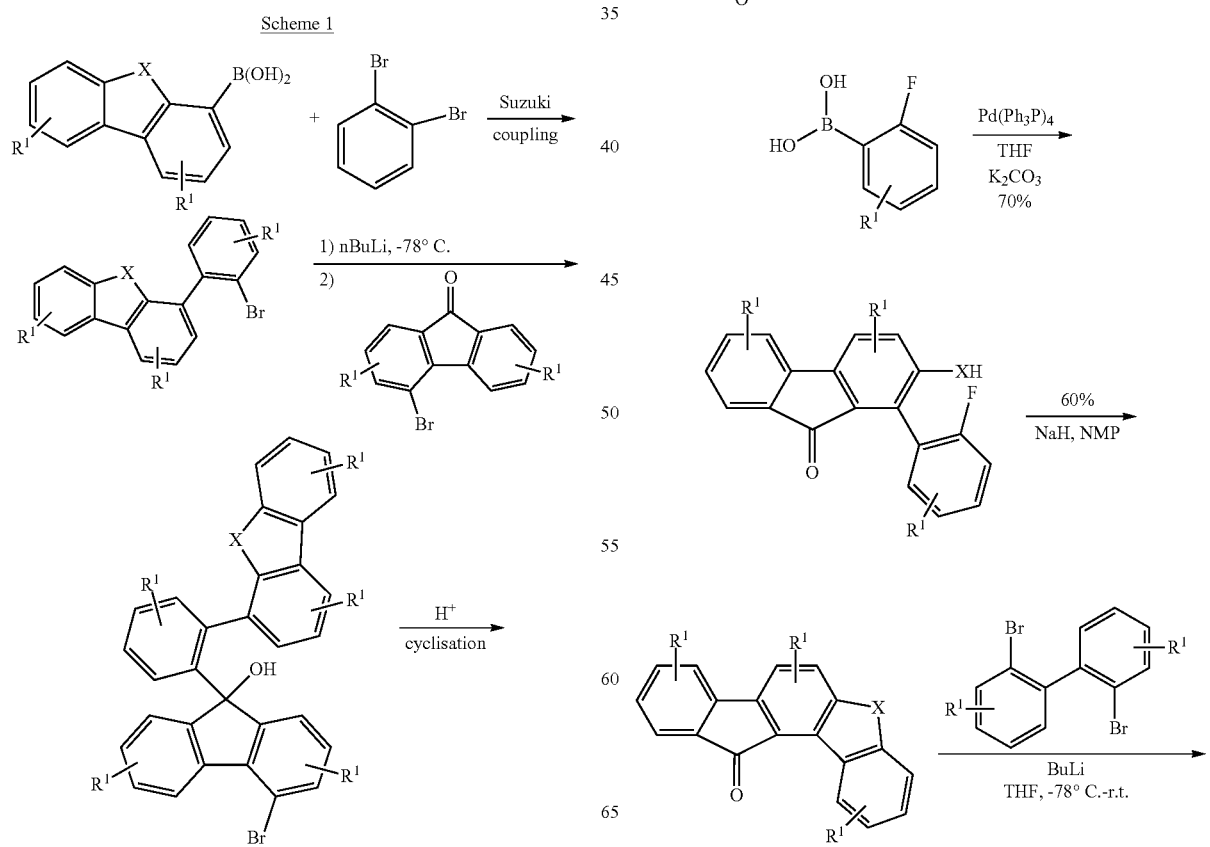

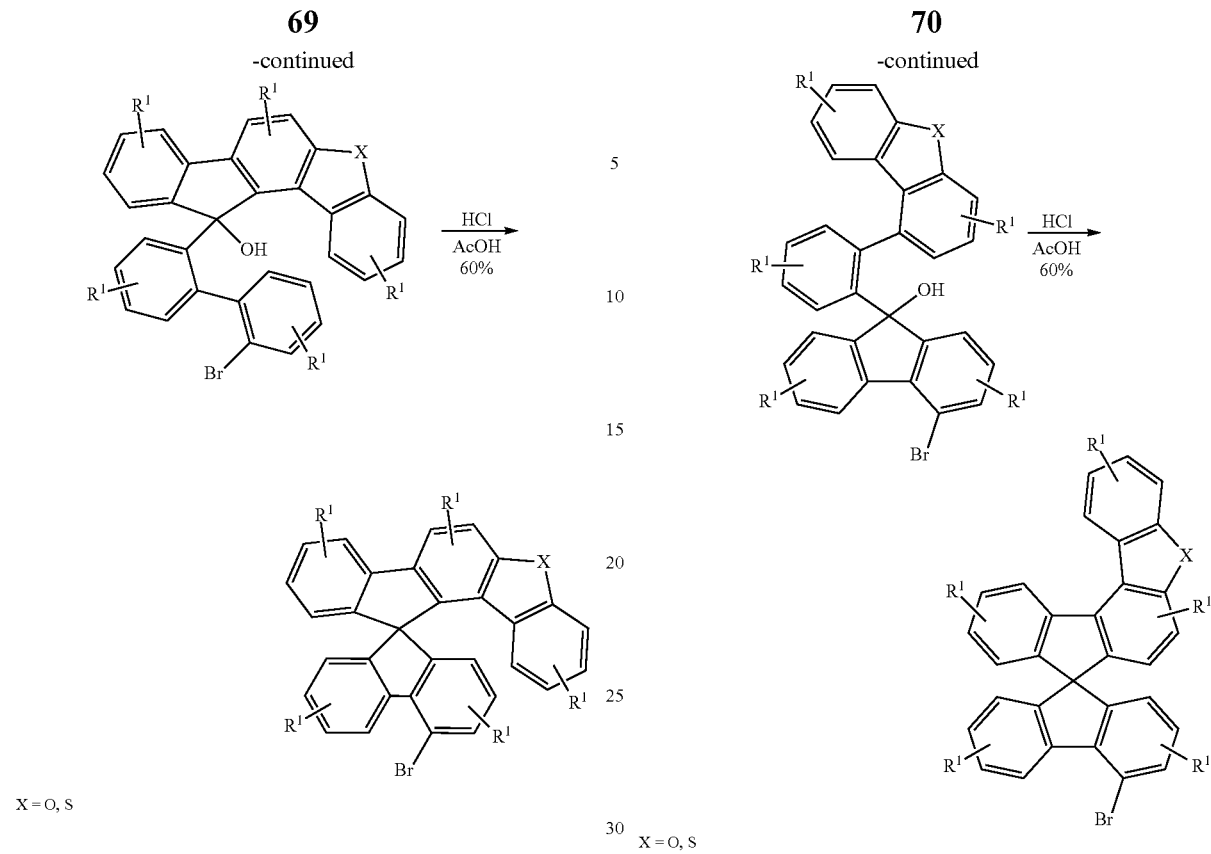

Furthermore, the corresponding halogenated spirobenzofluorenofuran or -thiophene derivatives of type C can be prepared starting from the corresponding boronic acid derivatives by Suzuki coupling and subsequent lithiation and further reaction with a 4-bromofluorenone derivative and subsequent cyclisation (Scheme 3).

The corresponding halogenated spirobenzofluorene derivatives of type D, preferably the spirobenzofluorenofuran or -thiophene derivatives, can be prepared starting from the benzofluorenofuranone derivative or benzofluorenothiophenone derivative by reaction with monolithiated 2,2′-dibromobiphenyl derivatives and subsequent cyclisation (Scheme 4).

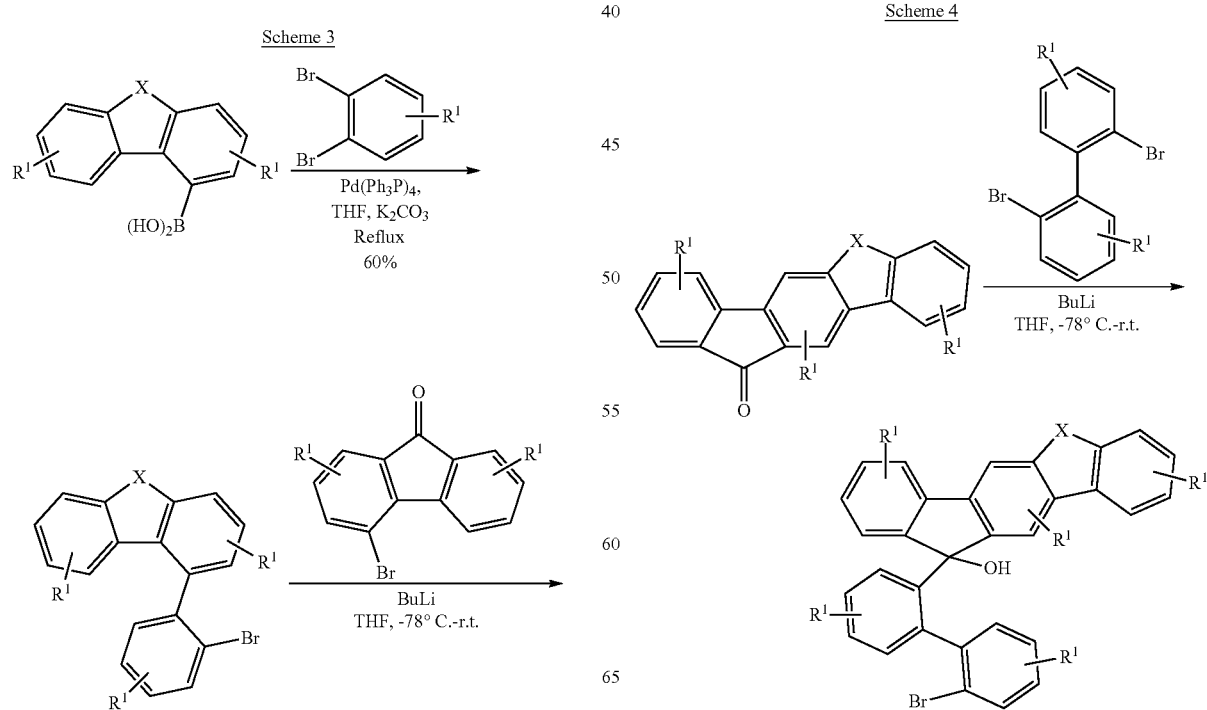

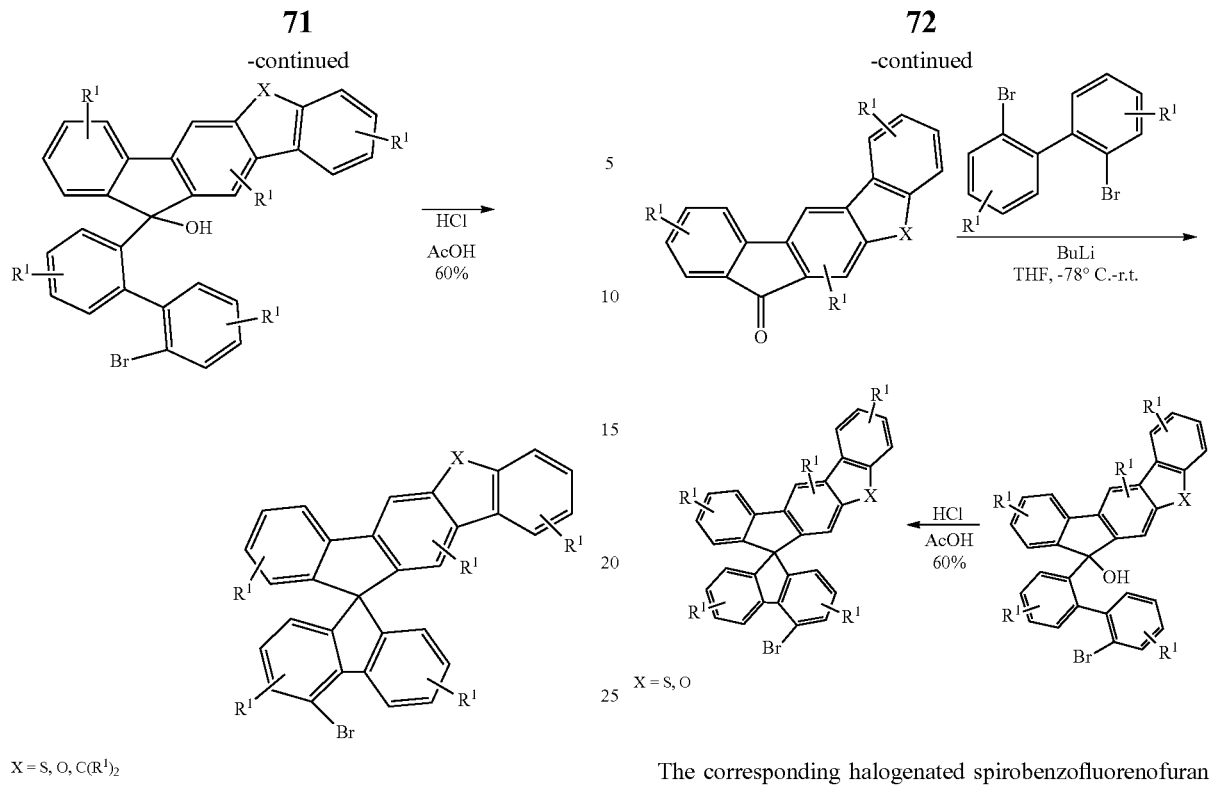

The corresponding halogenated spirobenzofluorenofuran or -thiophene derivatives of type E can be prepared starting from the halogenated mercaptofluorenone derivative or hydroxyfluorenone derivative by Suzuki coupling with subsequent cyclisation and further reaction with monolithiated 2,2'-dibromobiphenyl derivatives and further cyclisation (Scheme 5).

The corresponding halogenated spirobenzofluorenofuran or -thiophene derivatives of type F can be prepared starting from the benzofluorenofuran or -thiophene derivative or benzofluorenothiophene by reaction with monolithiated 2,2'-dibromobiphenyl derivatives and further cyclisation (Scheme 6).

Scheme 5

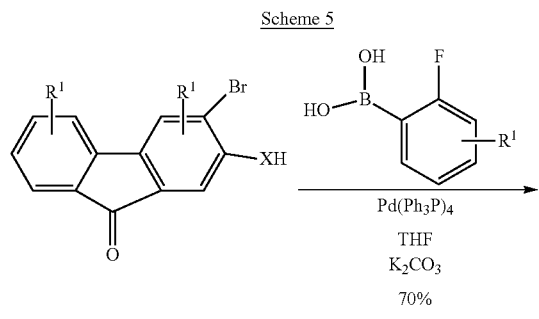

Scheme 6

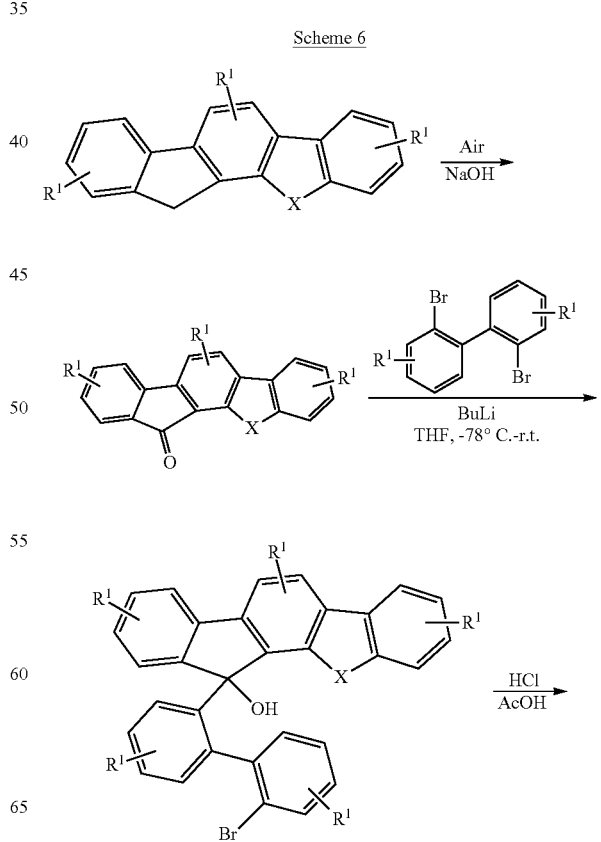

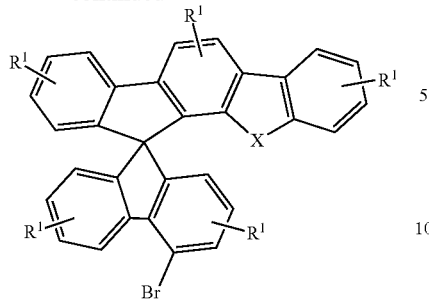

X = S, O

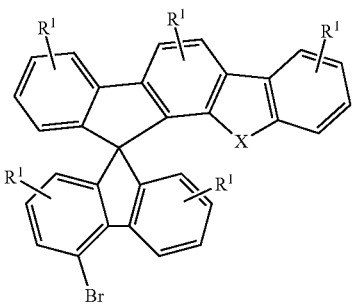

X = S, O, C(R¹)₂

A further way of preparing spirobenzofluorene derivatives of type F or D, preferably spirobenzofluorenofuran or -thiophene derivatives, is described in Scheme 7, where the synthetic procedure uses similar steps as shown in Scheme 6. The isomers are isolated by chromatography.

A further way of preparing spirofluorene derivatives, preferably dibenzofuran- or -thiophene-spirofluorene derivatives of type B or E, is described in Scheme 8, where the synthetic procedure uses similar steps as shown in Scheme 1. The isomers are isolated by chromatography.

Scheme 7

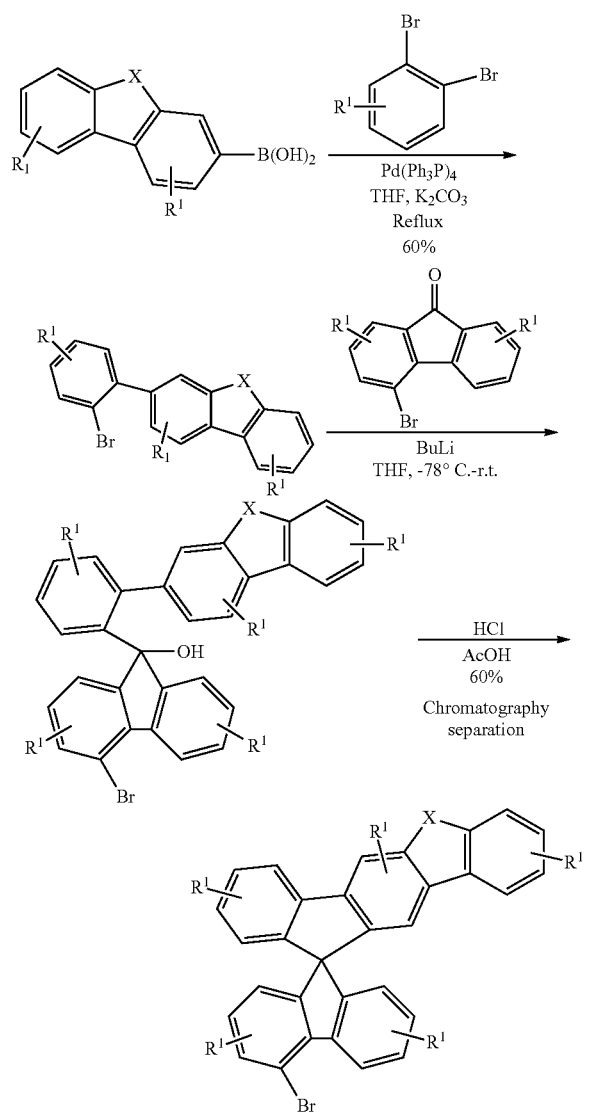

Scheme 8

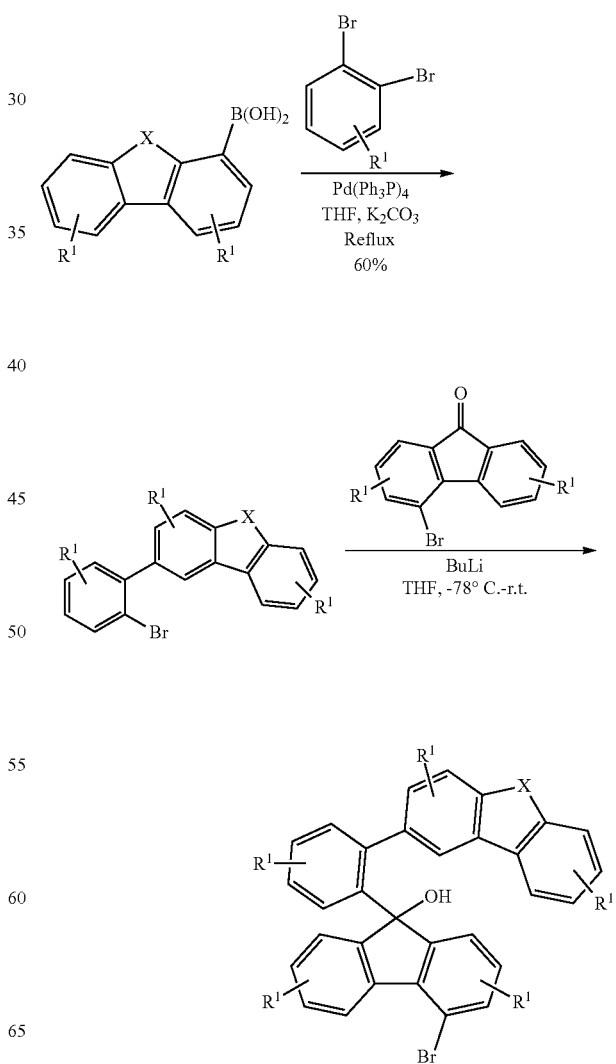

75
-continued
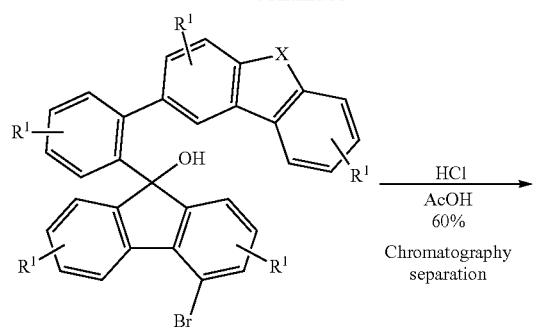
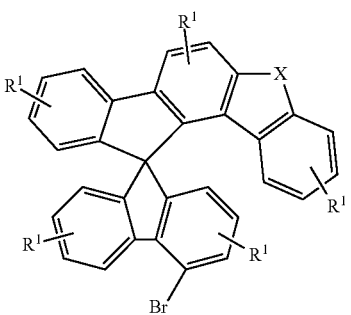
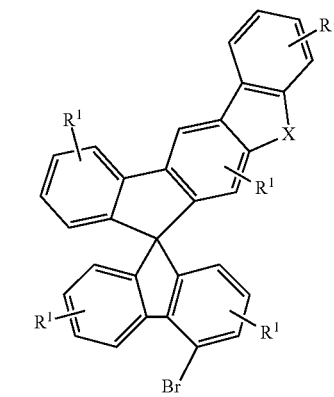
X = O, S, C(R¹)₂
The synthesis of halogen-free spirofluorene derivatives, preferably spiro-fluorenobenzofurans or -thiophenes, starts from halogen-free intermediates. Dibenzofuran or dibenzothiophene units can be functionalised by further lithiation or bromination (Scheme 9).
Scheme 9
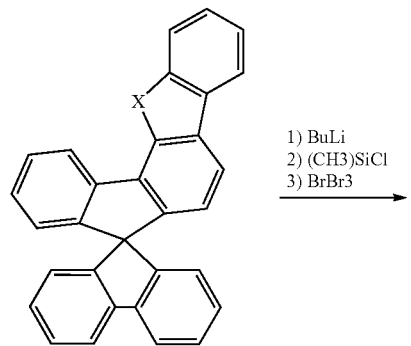
76
-continued
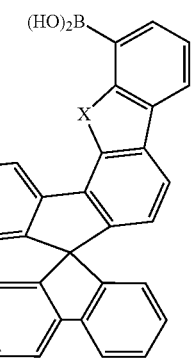
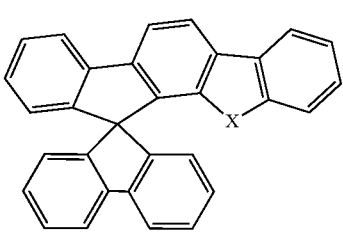
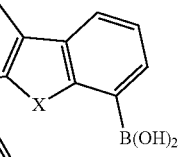
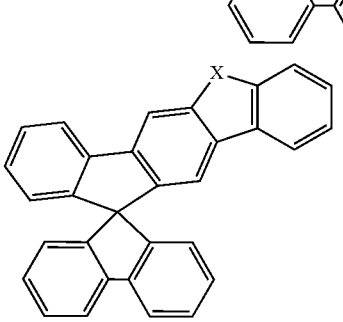
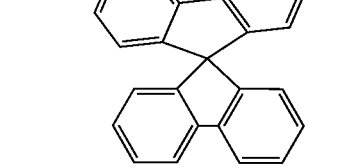
+
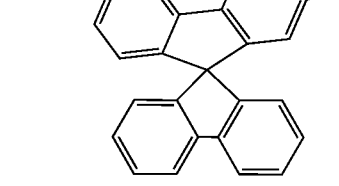
+

-continued

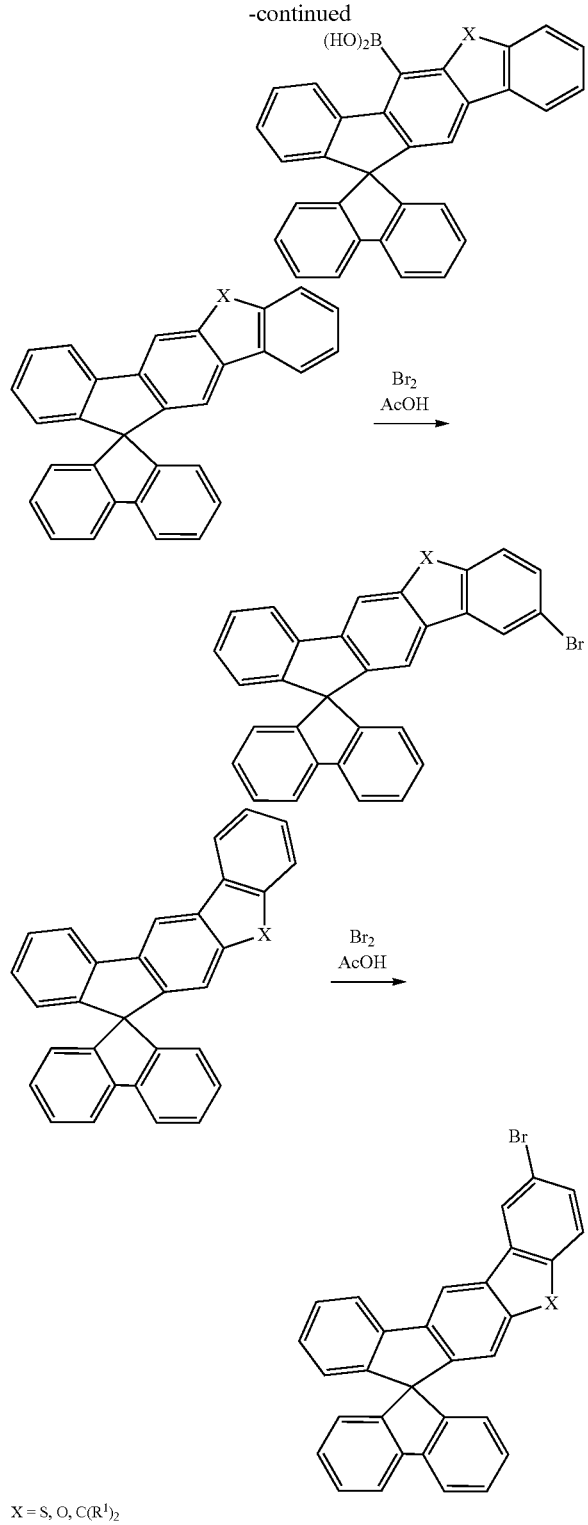

X = S, O, C(R¹)₂

The basic principles of the preparation processes described above are known in principle from the literature for similar compounds and can easily be adapted by the person skilled in the art for the preparation of the compounds according to the invention.

These processes, optionally followed by purification, such as, for example, recrystallisation or sublimation, enable the compounds according to the invention containing structures of the formula (I) to be obtained in high purity, preferably greater than 99% (determined by means of ¹H-NMR and/or HPLC).

The compounds according to the invention may also contain suitable substituents, for example relatively long alkyl groups (about 4 to 20 C atoms), in particular branched alkyl groups, or optionally substituted aryl groups, for example xylyl, mesityl or branched terphenyl or quaterphenyl groups, which effect solubility in common organic solvents, such as, for example, toluene or xylene, at room temperature in adequate concentration in order to be able to process the complexes from solution. These soluble compounds are particularly suitable for processing from solution, for example by printing processes. Furthermore, it should be noted that the compounds according to the invention containing at least one structure of the formula (I) already have increased solubility in these solvents.

The compounds according to the invention can also be mixed with a polymer. It is likewise possible to incorporate these compounds covalently into a polymer. This is possible, in particular, with compounds which are substituted by reactive leaving groups, such as bromine, iodine, chlorine, boronic acid or boronic acid ester, or by reactive, polymerisable groups, such as olefins or oxetanes. These can be used as monomers for the preparation of corresponding oligomers, dendrimers or polymers. The oligomerisation or polymerisation here preferably takes place via the halogen functionality or the boronic acid functionality or via the polymerisable group. It is furthermore possible to crosslink the polymers via such groups. The compounds and polymers according to the invention can be employed as crosslinked or uncrosslinked layer.

The invention therefore furthermore relates to oligomers, polymers or dendrimers containing one or more of the structures of the formula (I) shown above or compounds according to the invention, where one or more bonds are present from the compounds according to the invention or the structures of the formula (I) to the polymer, oligomer or dendrimer. Depending on the linking of the structures of the formula (I) or the compounds, these therefore form a side chain of the oligomer or polymer or are linked in the main chain. The polymers, oligomers or dendrimers may be conjugated, partially conjugated or non-conjugated. The oligomers or polymers may be linear, branched or dendritic. The same preferences as described above apply to the recurring units of the compounds according to the invention in oligomers, dendrimers and polymers.

For the preparation of the oligomers or polymers, the monomers according to the invention are homopolymerised or copolymerised with further monomers. Preference is given to copolymers, where the units of the formula (I) or the preferred embodiments indicated above are present to the extent of 0.01 to 99.9 mol %, preferably 5 to 90 mol %, particularly preferably 20 to 80 mol %. Suitable and preferred comonomers which form the polymer backbone are selected from fluorenes (for example in accordance with EP 842208 or WO 2000/022026), spirobifluorenes (for example in accordance with EP 707020, EP 894107 or WO 2006/061181), para-phenylenes (for example in accordance with WO 92/18552), carbazoles (for example in accordance with WO 2004/070772 or WO 2004/113468), thiophenes (for example in accordance with EP 1028136), dihydrophenanthrenes (for example in accordance with WO 2005/014689), cis- and trans-indeno-fluorenes (for example in accordance with WO 2004/041901 or WO 2004/113412), ketones (for example in accordance with WO 2005/040302), phenanthrenes (for example in accordance with WO 2005/

104264 or WO 2007/017066) or also a plurality of these units. The polymers, oligomers and dendrimers may also contain further units, for example hole-transport units, in particular those based on triarylamines, and/or electron-transport units.

Furthermore, the present compounds may have a relatively low molecular weight. The present invention accordingly furthermore relates to a compound which has a molecular weight of preferably at most 10,000 g/mol, particularly preferably at most 5000 g/mol and especially preferably at most 3000 g/mol.

Furthermore, preferred compounds are distinguished by being sublimable. These compounds generally have a molar mass of less than about 1200 g/mol.

Of particular interest are furthermore compounds according to the invention which are distinguished by a high glass-transition temperature. In this connection, particular preference is given to compounds according to the invention containing structures of the general formula (I) which have a glass-transition temperature of at least 70° C., particularly preferably at least 110° C., very particularly preferably at least 125° C. and especially preferably at least 150° C., determined in accordance with DIN 51005.

The present invention still furthermore relates to a formulation comprising a compound according to the invention or an oligomer, polymer or dendrimer according to the invention and at least one further compound. The further compound may preferably be a solvent. However, the further compound may also be a further organic or inorganic compound which is likewise employed in the electronic device, for example a matrix material. This further compound may also be polymeric.

Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention still furthermore relates to a composition comprising a compound according to the invention and at least one further organofunctional material. Functional materials are generally the organic or inorganic materials which are introduced between the anode and the cathode. The organofunctional material is preferably selected from the group consisting of fluorescent emitters, phosphorescent emitters, n-dopants, host materials, matrix materials, electron-transport materials, electron-injection materials, hole-conductor materials, hole-injection materials, electron-blocking materials and hole-blocking materials.

The present invention therefore furthermore relates, in particular, to a composition which is characterised in that the organofunctional material is an electron-transport material.

The preferred electron-transport materials include, inter alia, electron-deficient heteroaromatic compounds. The electron-deficient heteroaromatic compounds include, inter alia, pyridines, pyrazines, pyrimidines, pyridazines, 1,2,4-triazines, 1,3,5-triazines, quinolines, isoquinolines, quinoxalines, pyrazoles, imidazoles, benzimidazoles, thiazoles, benzothiazoles, oxazoles or benzoxazoles.

It may furthermore be provided in accordance with the invention that the composition, besides compounds containing structures of the formula (I), preferably comprises at least one n-dopant as organofunctional material.

n-Dopants herein are taken to mean reducing agents, i.e. electron donors. Preferred examples of n-dopants are $W(hpp)_4$ and further electron-rich metal complexes in accordance with WO 2005/086251 A2, P=N compounds (for example WO 2012/175535 A1, WO 2012/175219 A1), naphthylenecarbodiimides (for example WO 2012/168358 A1), fluorenes (for example WO 2012/031735 A1), free radicals and diradicals (for example EP 1837926 A1, WO 2007/107306 A1), pyridines (for example EP 2452946 A1, EP 2463927 A1), N-heterocyclic compounds (for example WO 2009/000237 A1) and acridines as well as phenazines (for example US 2007/145355 A1).

The present invention therefore also relates to a composition comprising at least one compound containing structures of the formula (I) and at least one further matrix or host material. According to a particular aspect of the present invention, the further matrix or host material has hole-transporting properties.

The preferred matrix or host materials which have hole-transporting properties include arylamines, triarylamines, bridged amines; preferred bridged amines here are dihydroacridines, dihydrophenazines, phenoxazines and phenothiazines, carbazoles, bridged carbazoles, biscarbazoles, indenocarbazoles and indolocarbazoles.

The present invention furthermore relates to a composition comprising at least one compound containing at least one structure of the formula (I) and at least one wide band gap material, where a wide band gap material is taken to mean a material in the sense of the disclosure of U.S. Pat. No. 7,294,849.

These systems exhibit particularly advantageous performance data in electroluminescent devices.

The additional compound can preferably have a band gap of 2.5 eV or more, preferably 3.0 eV or more, very preferably 3.5 eV or more. The band gap can be calculated, inter alia, by means of the energy levels of the highest occupied molecular orbital (HOMO) and the lowest unoccupied molecular orbital (LUMO), as described by way of example above.

The present invention also relates to a composition comprising at least one compound containing structures of the formula (I) and at least one phosphorescent emitter, where the term phosphorescent emitter is also taken to mean phosphorescent dopants.

The term phosphorescent dopants typically encompasses compounds in which the light emission takes place through a spin-forbidden transition, for example a transition from an excited triplet state or a state having a relatively high spin quantum number, for example a quintet state.

Suitable phosphorescent dopants are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

All luminescent iridium, platinum or copper complexes are regarded as phosphorescent compounds in the sense of the present application. Examples of phosphorescent dopants are given in a following section.

A dopant in a system comprising a matrix material and a dopant is taken to mean the component whose proportion in the mixture is the smaller. Correspondingly, a matrix material in a system comprising a matrix material and a dopant is taken to mean the component whose proportion in the mixture is the larger.

Preferred phosphorescent dopants for use in mixed-matrix systems are the preferred phosphorescent dopants indicated below.

Examples of phosphorescent dopants are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as are used in accordance with the prior art for phosphorescent OLEDs and as are known to the person skilled in the art in the area of organic electroluminescent devices are suitable for use in the devices according to the invention.

Explicit examples of phosphorescent dopants are shown in the following table

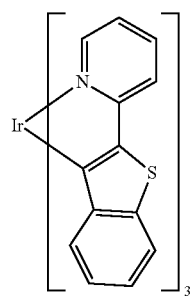

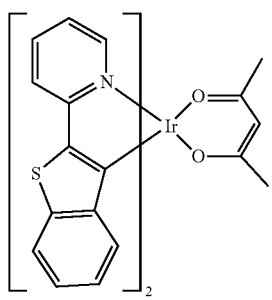

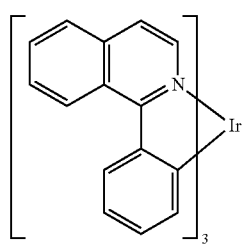

-continued

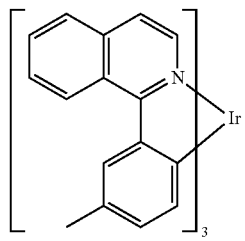

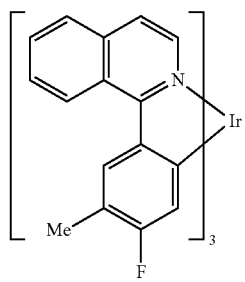

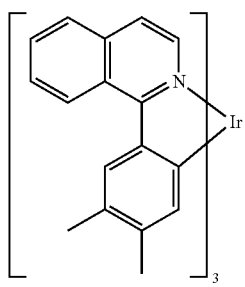

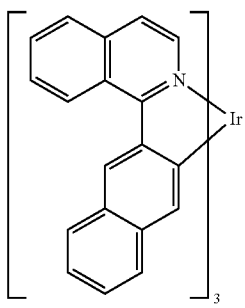

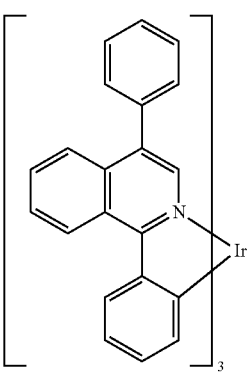

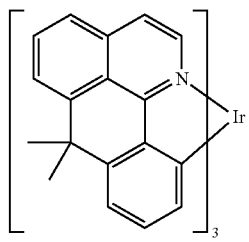
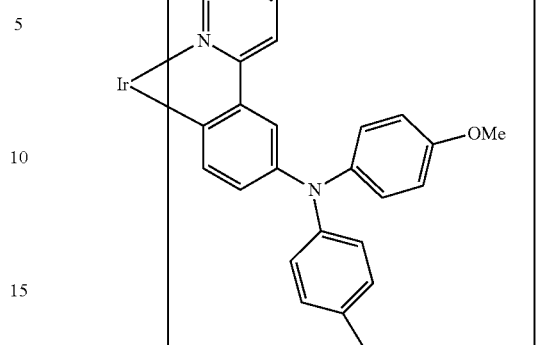
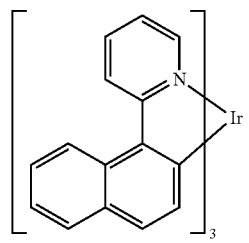
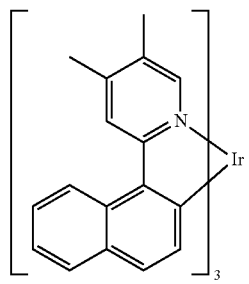
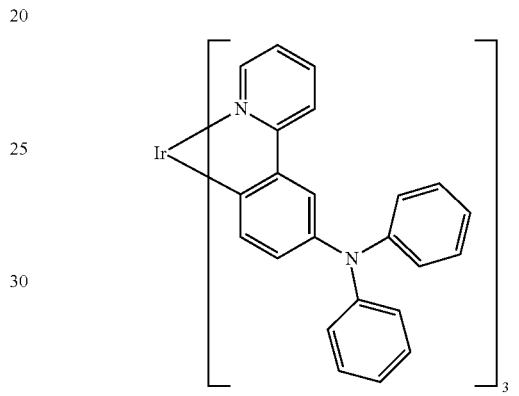
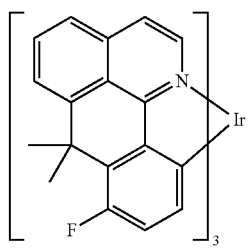
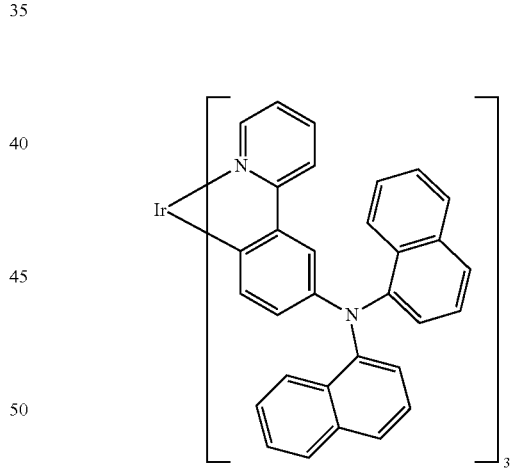
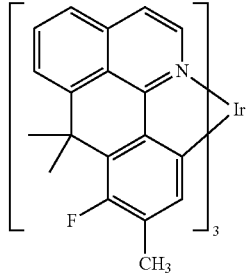
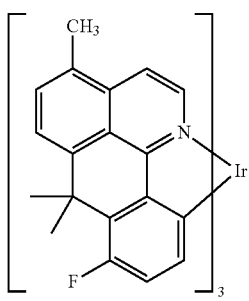
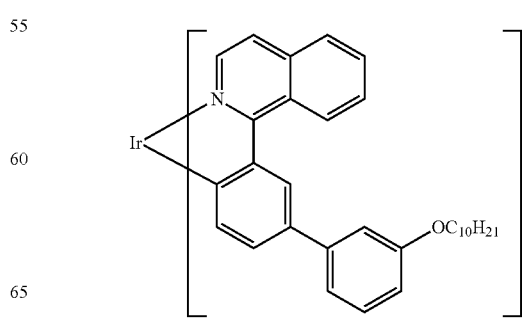

-continued
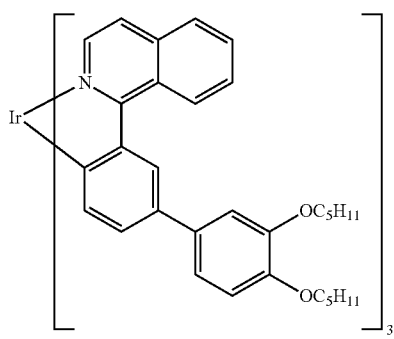
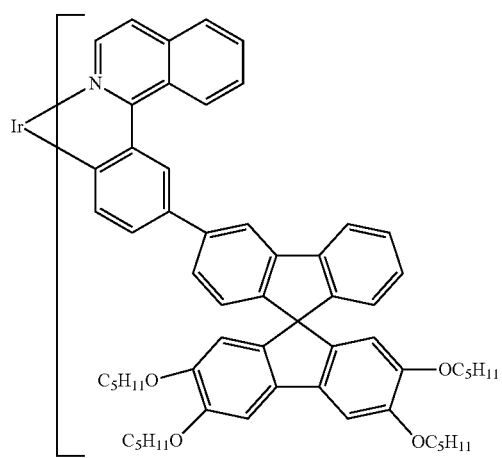
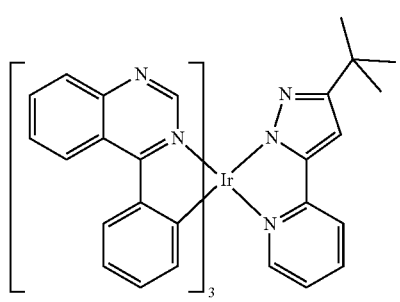
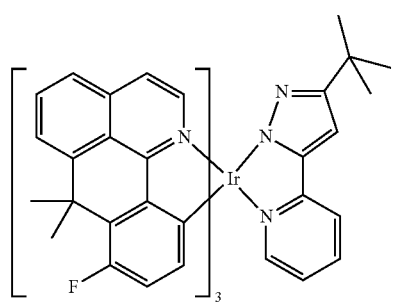
-continued
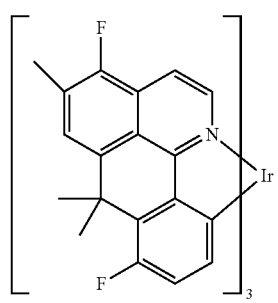
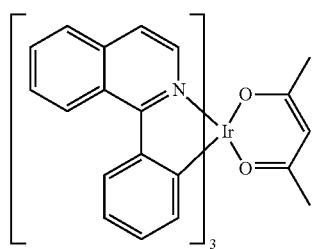
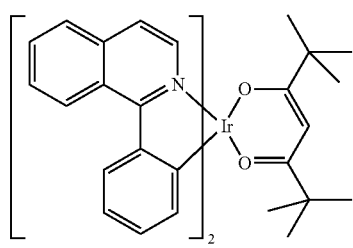
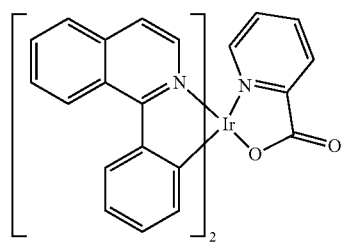
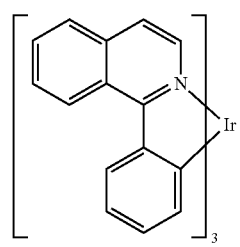
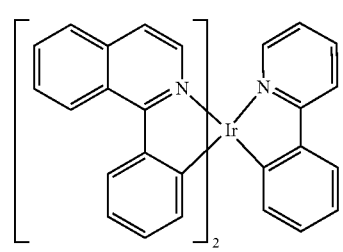

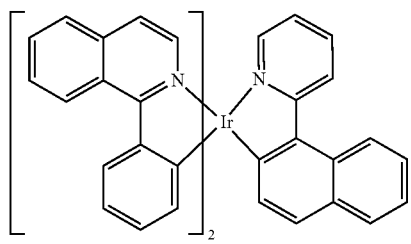
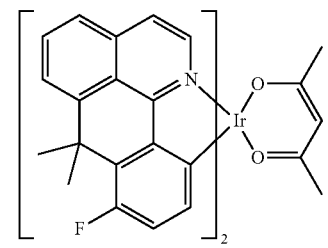
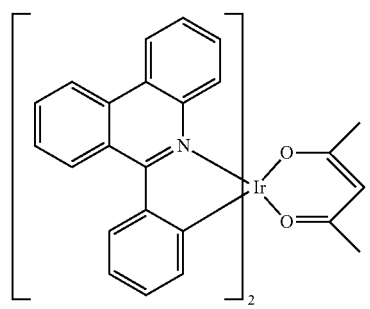
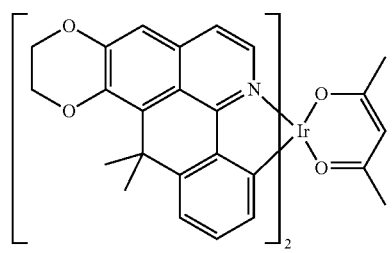
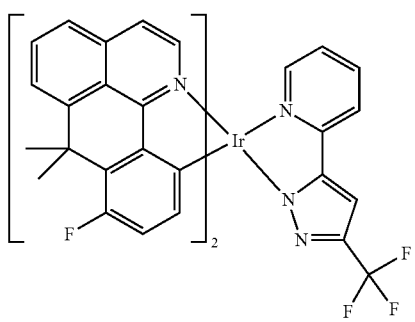
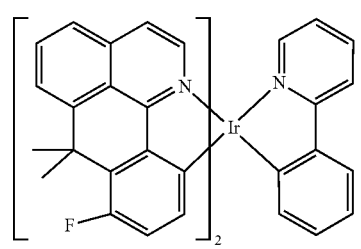
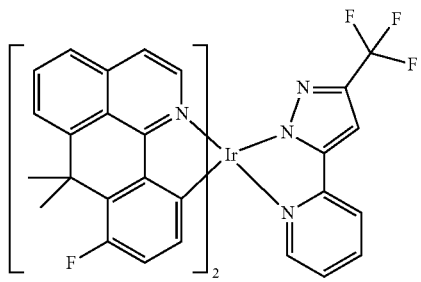
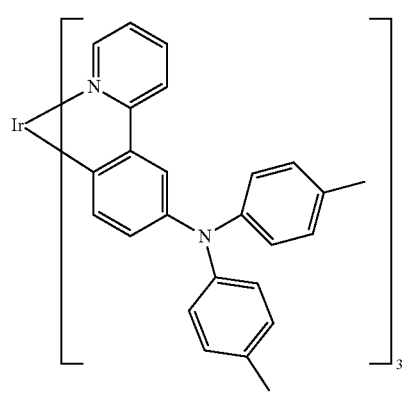
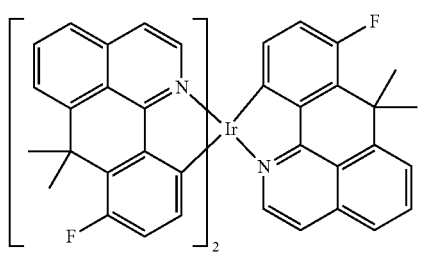
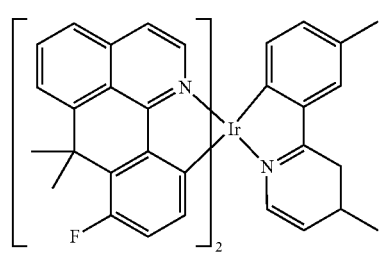
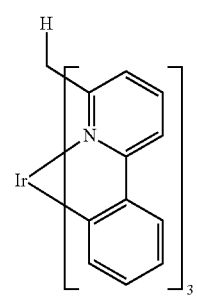

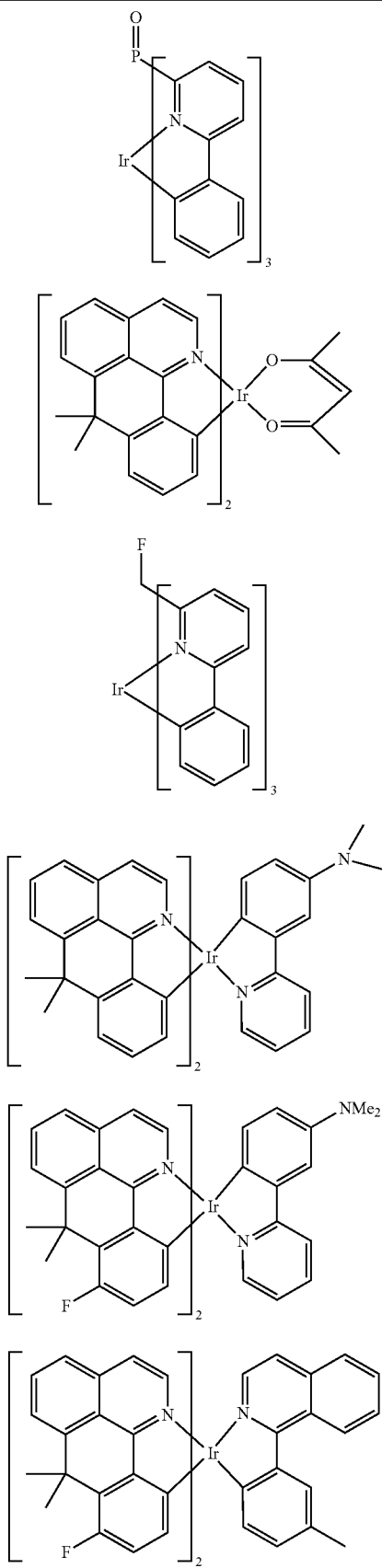
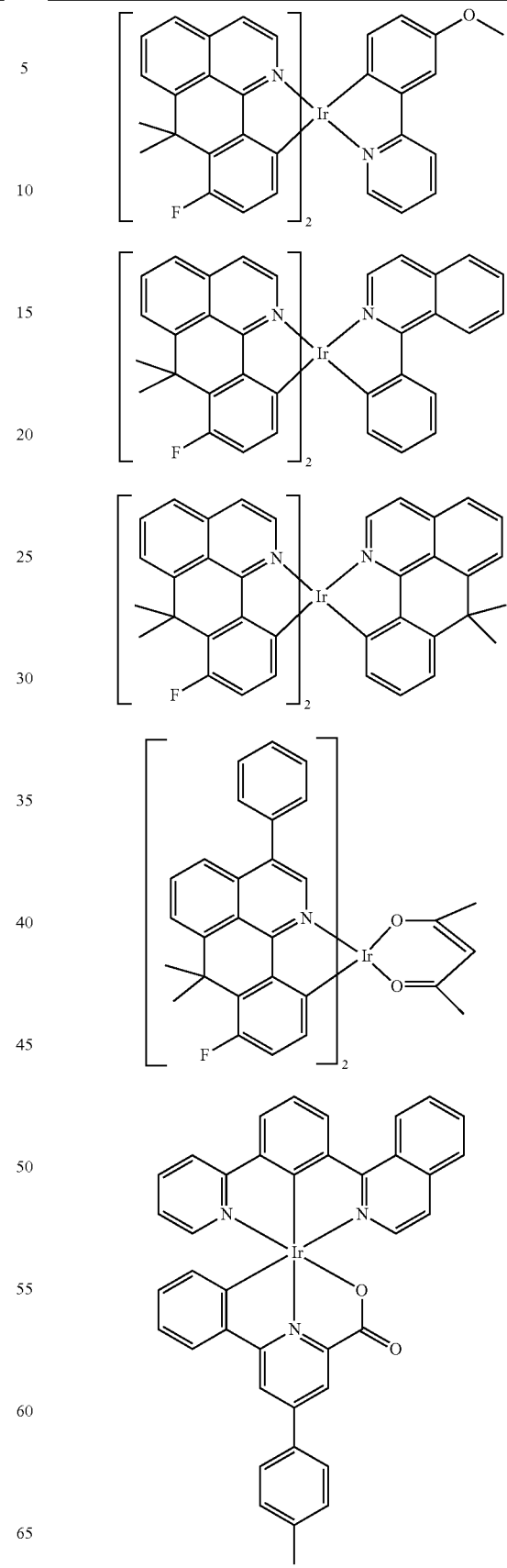

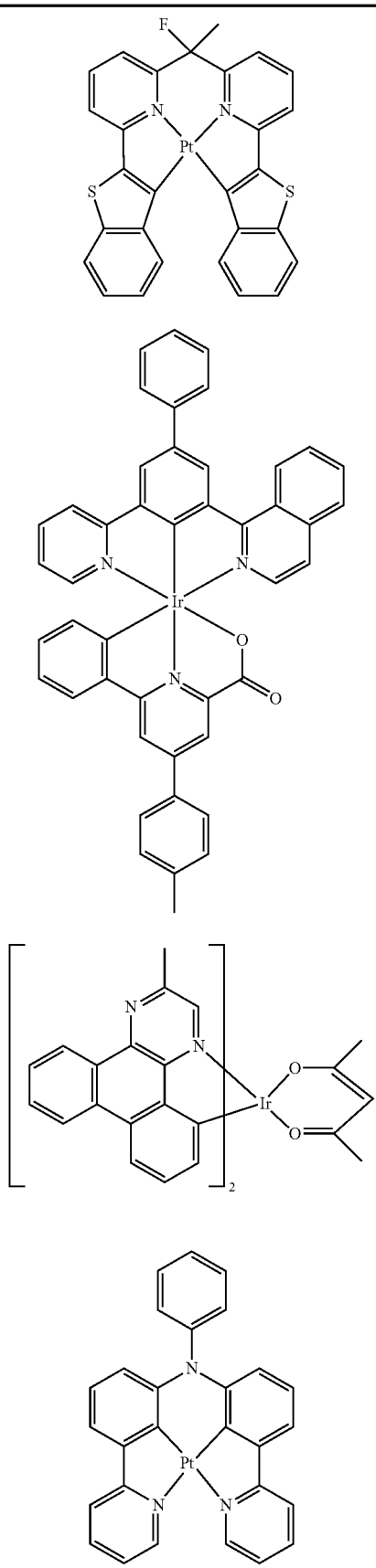
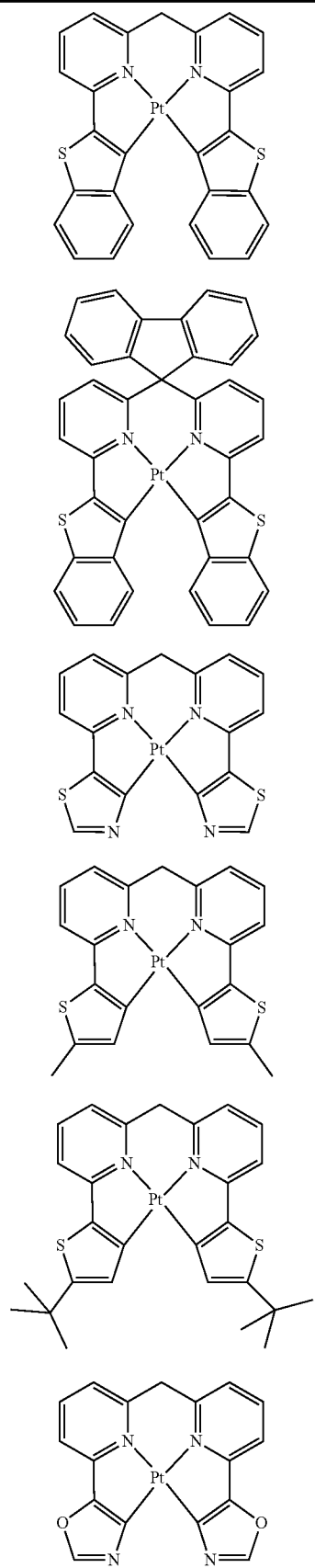

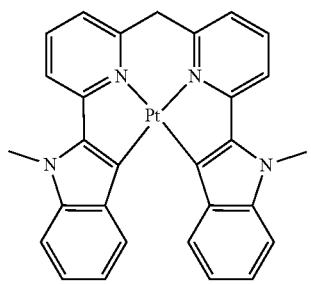
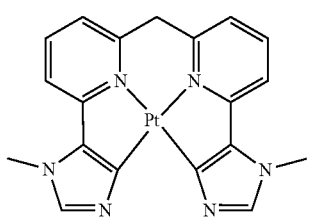
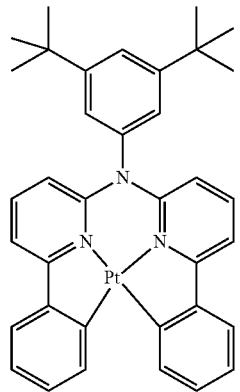
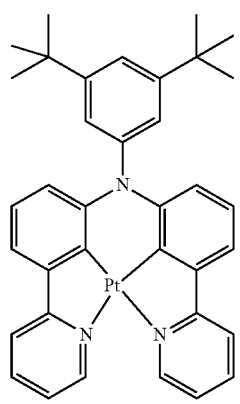
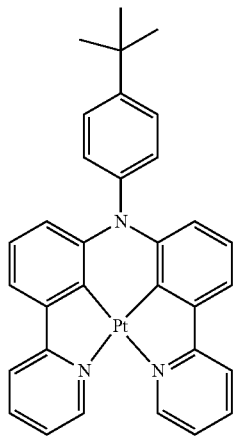
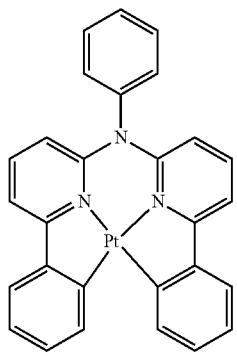
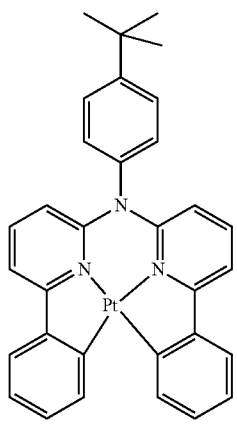
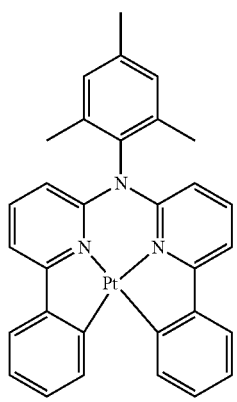

95
-continued
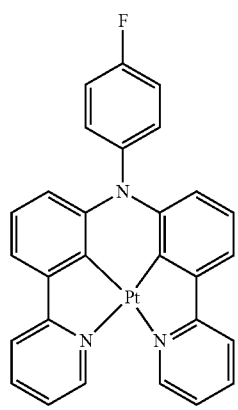
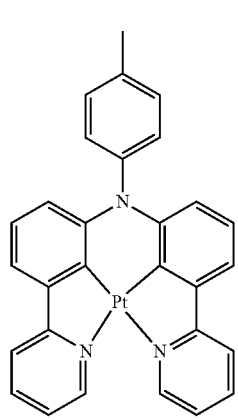
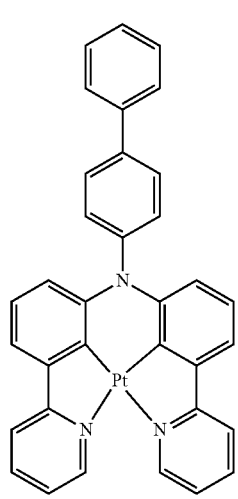
96
-continued
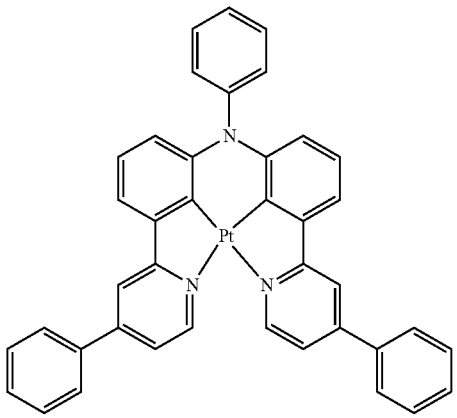
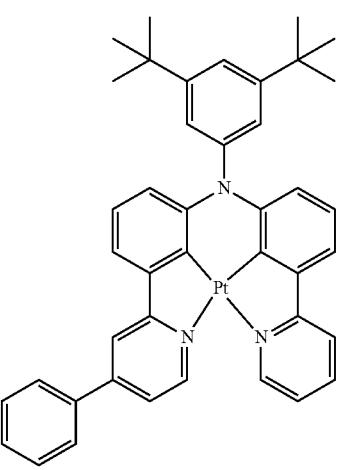
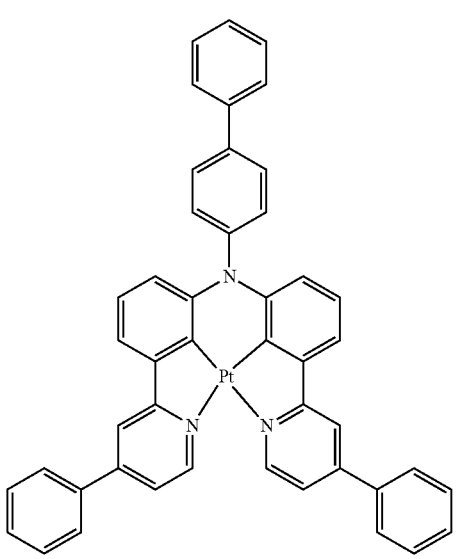

97
-continued
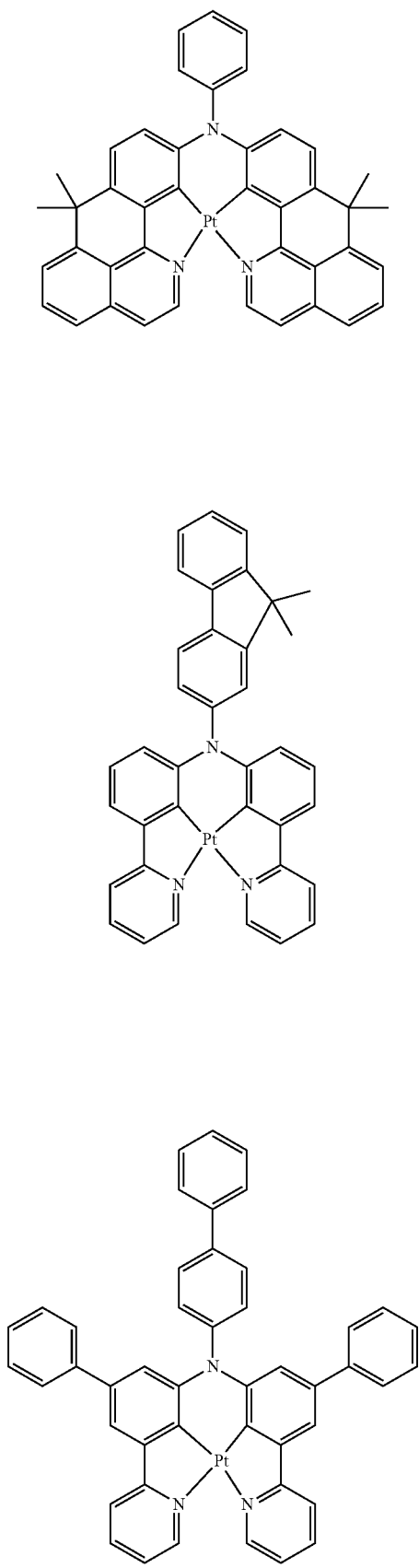
98
-continued
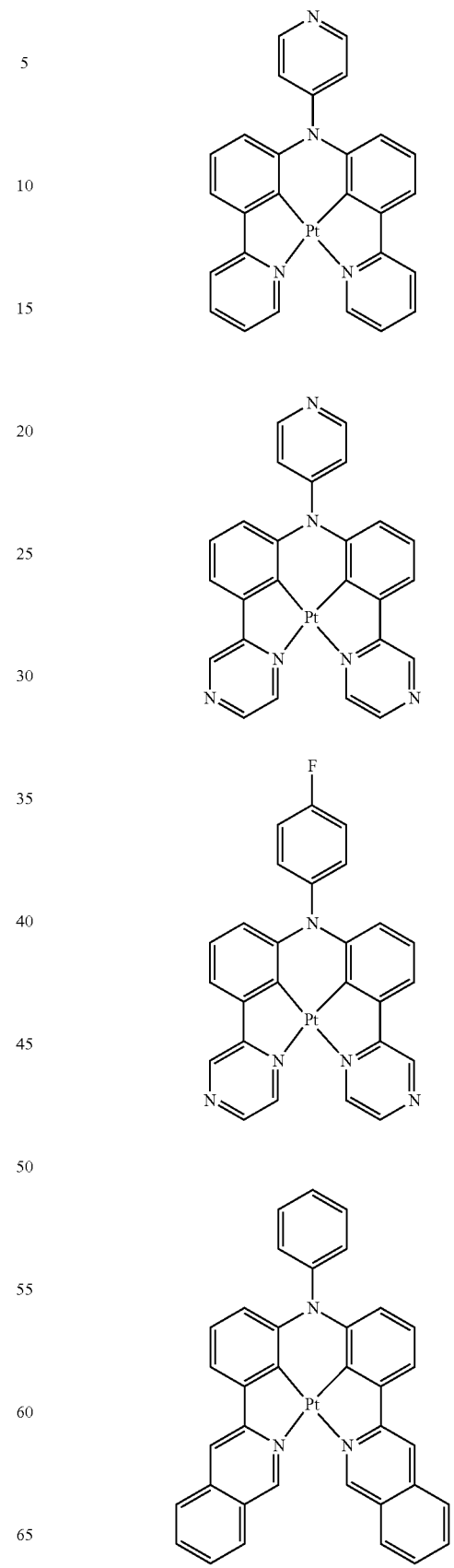

| 99 -continued | 100 -continued |
|---|---|
| 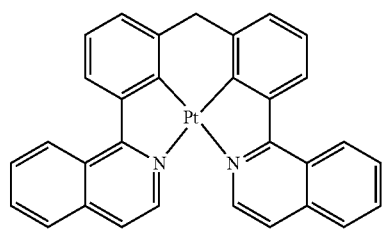 | 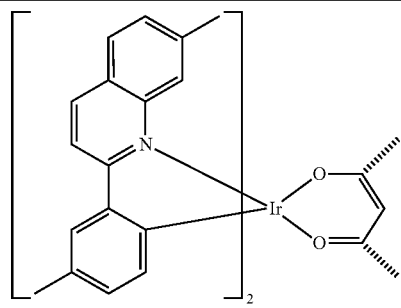 |
| 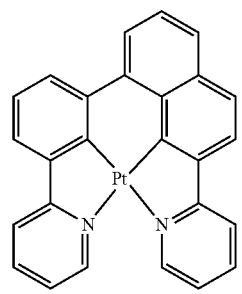 | 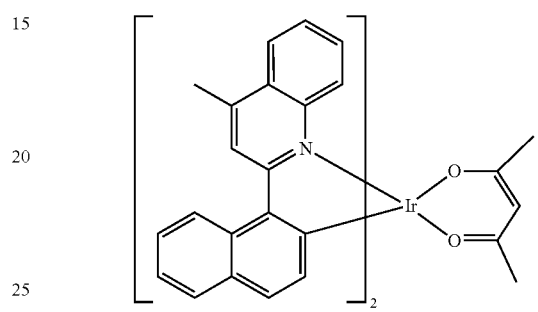 |
| 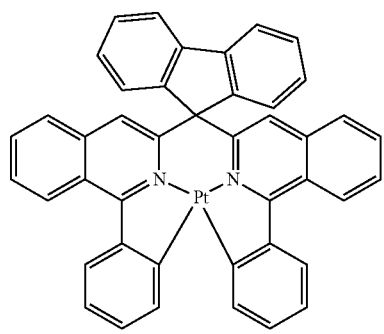 | 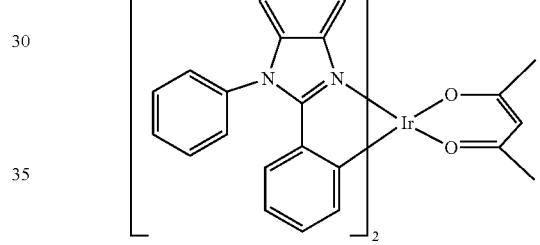 |
| 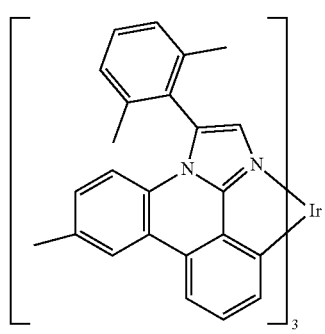 | 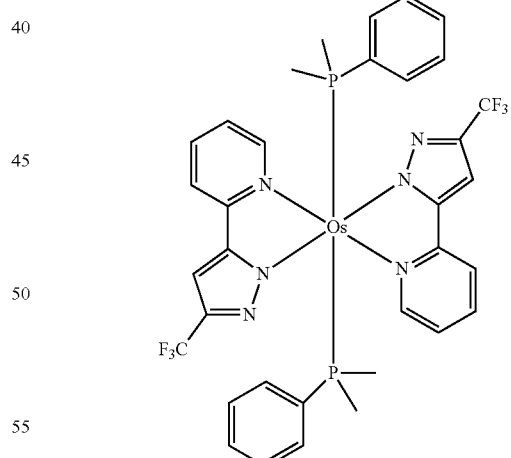 |
| 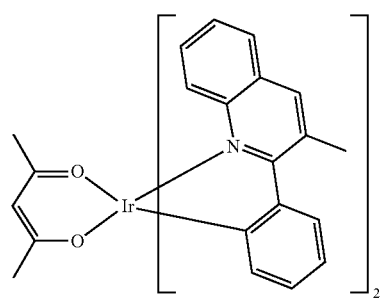 | 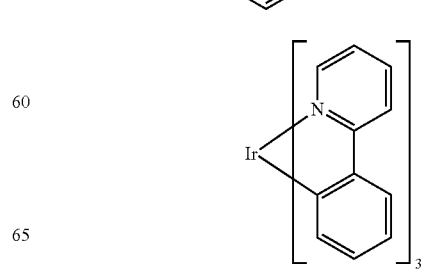 |

101
-continued
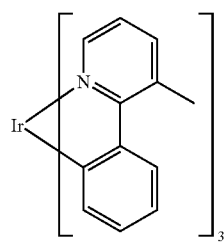
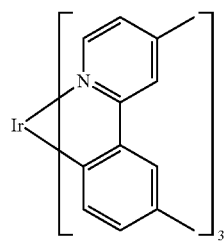
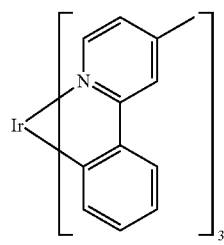
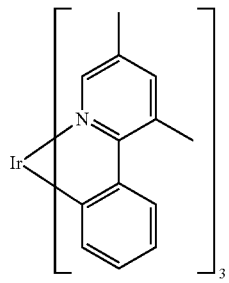
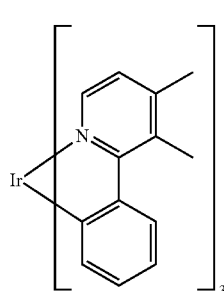
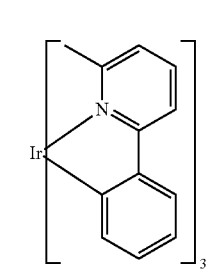
102
-continued
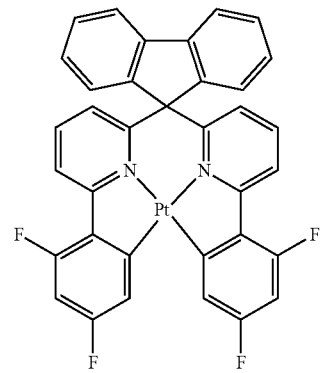
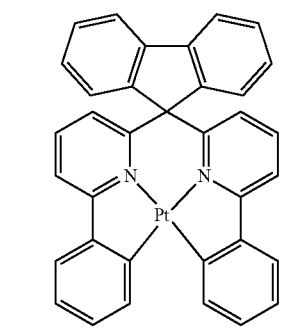
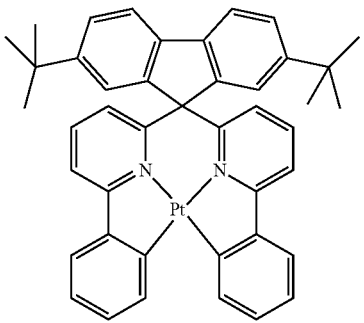
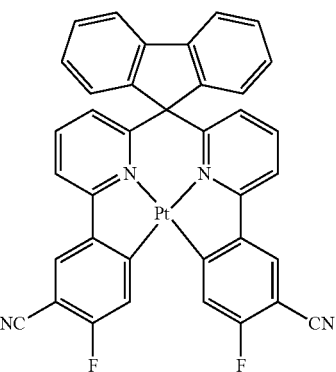

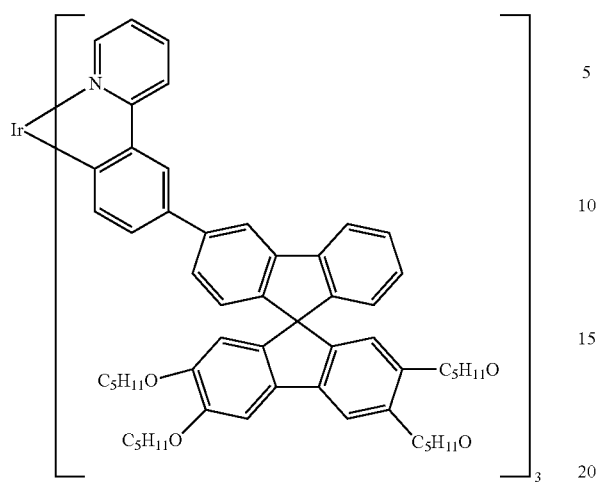
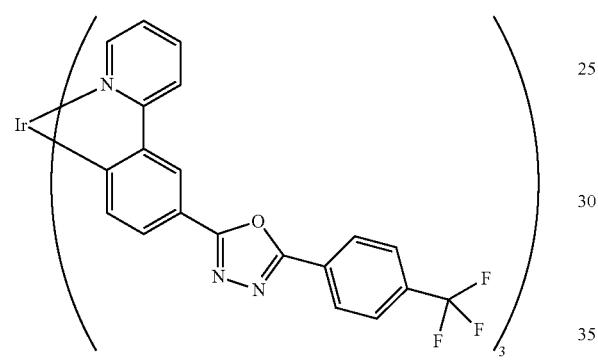
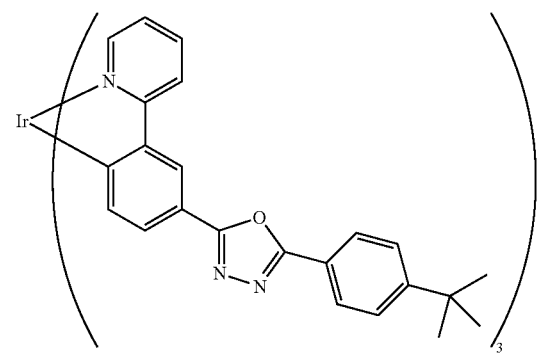
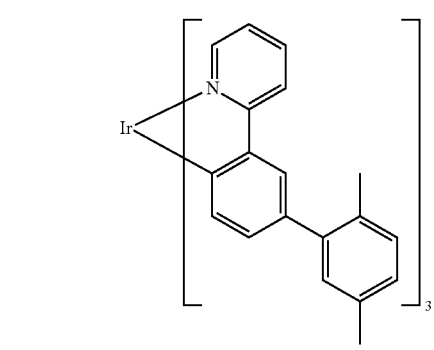
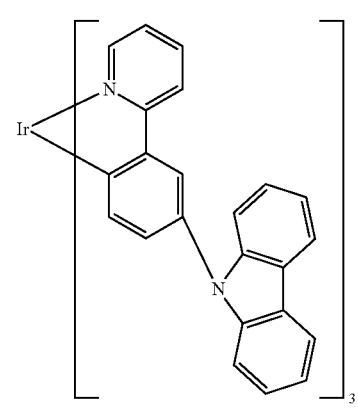
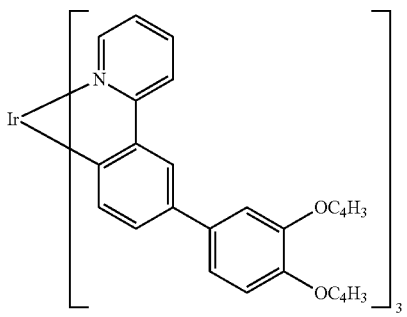
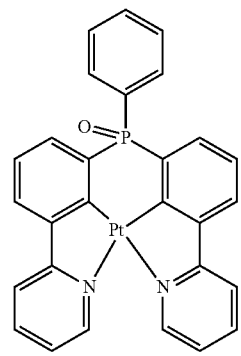
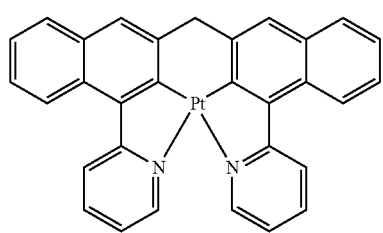

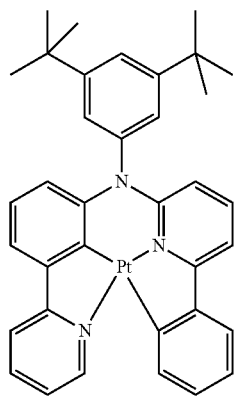
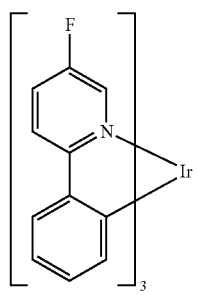
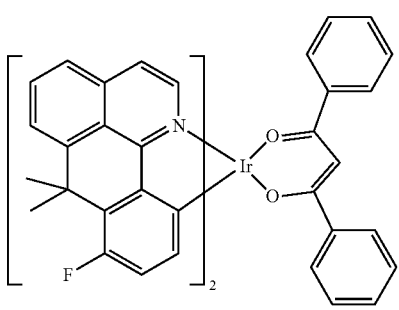
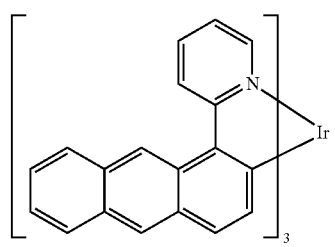
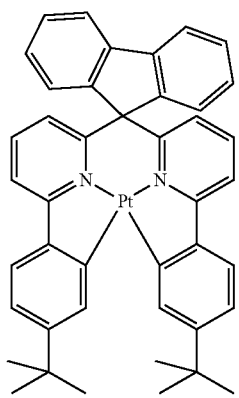
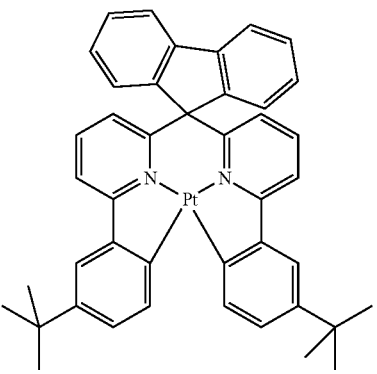
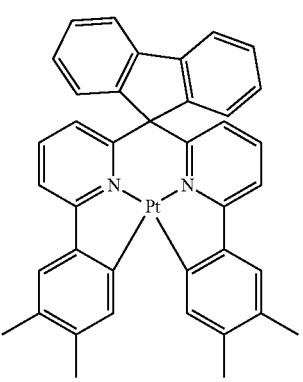
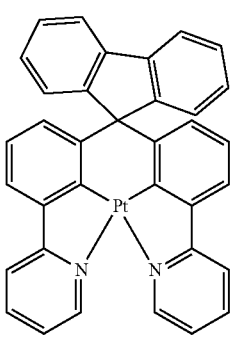
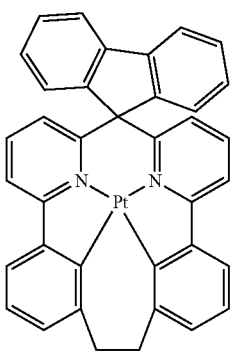

107
-continued
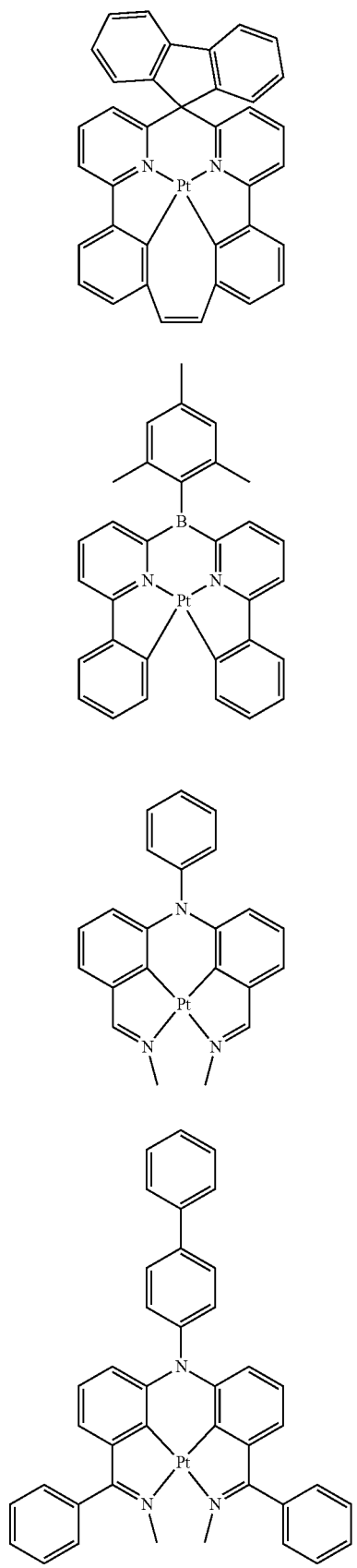
108
-continued
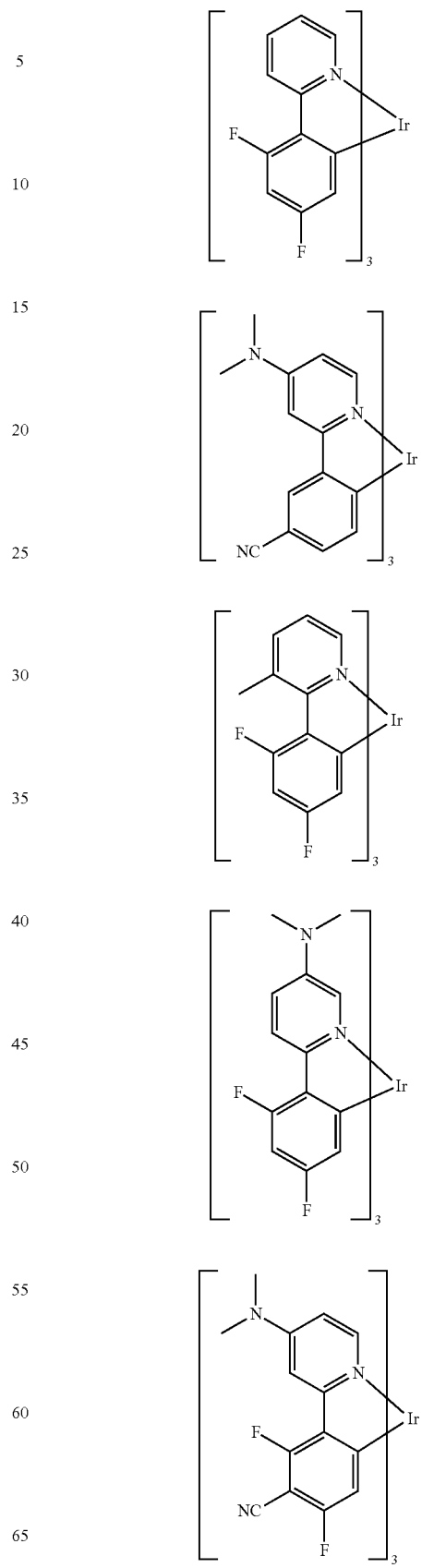

| 109 -continued | 110 -continued |
|---|---|
| 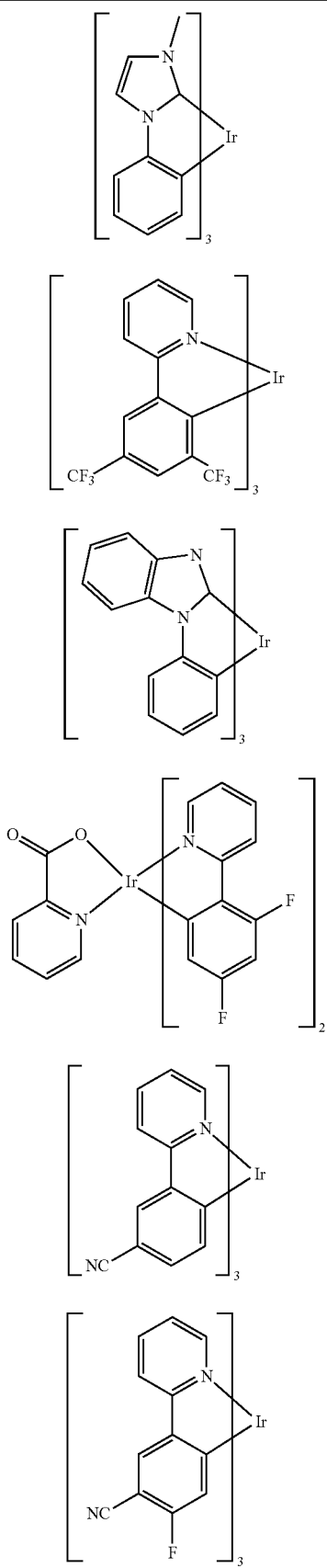 | 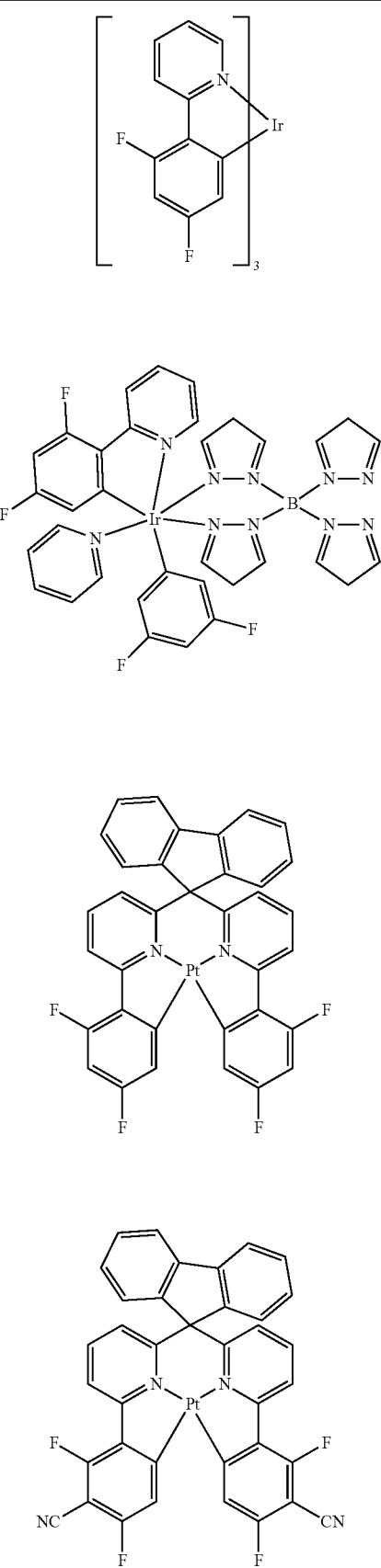 |

111
-continued
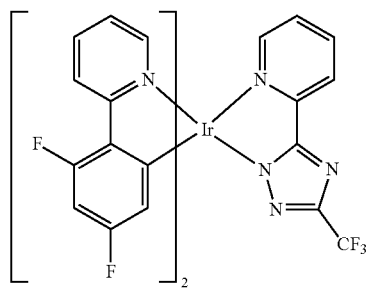
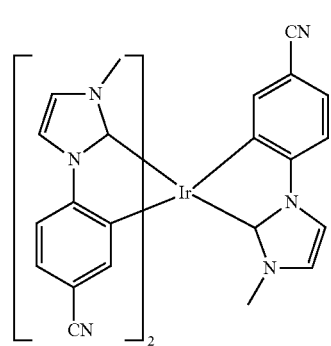
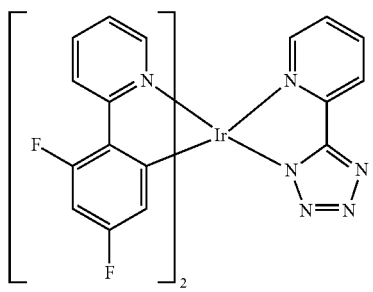
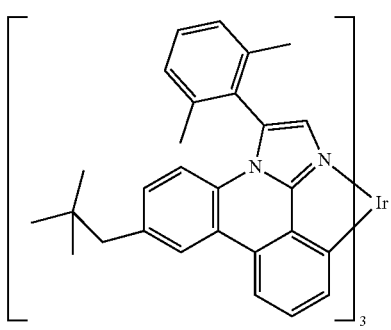
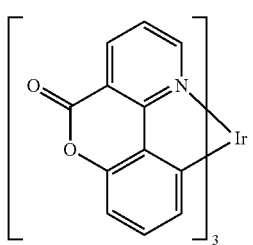
112
-continued
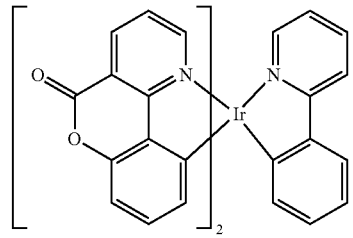
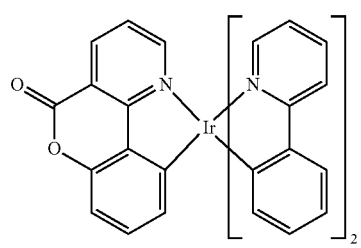
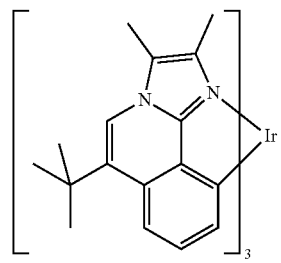
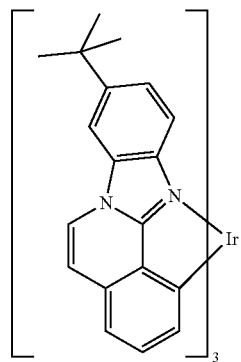
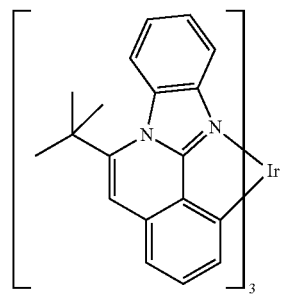

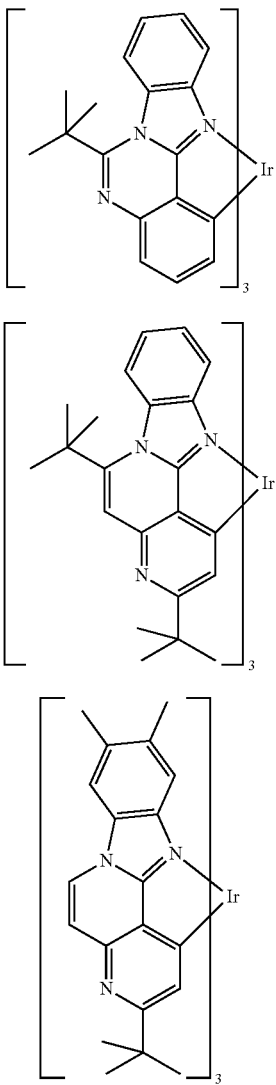

The compound described above containing structures of the formula (I) or the preferred embodiments indicated above can preferably be used as active component in an electronic device. An electronic device is taken to mean a device which comprises an anode, a cathode and at least one layer, where this layer comprises at least one organic or organometallic compound. The electronic device according to the invention thus comprises an anode, a cathode and at least one layer which comprises at least one compound containing structures of the formula (I). Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), comprising at least one compound containing structures of the formula (I) in at least one layer.

Particular preference is given to organic electroluminescent devices. Active components are generally the organic or inorganic materials which have been introduced between the anode and cathode, for example charge-injection, charge-transport or charge-blocking materials, but in particular emission materials and matrix materials. The compounds according to the invention exhibit particularly good properties as electron-transport material in organic electroluminescent devices. A preferred embodiment of the invention are therefore organic electroluminescent devices comprising at least one layer comprising at least one compound according to the invention.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers, charge-generation layers and/or organic or inorganic p/n junctions. It is possible here for one or more hole-transport layers to be p-doped, for example with metal oxides, such as $MoO_3$ or $WO_3$, or with (per)fluorinated electron-deficient aromatic compounds, and/or for one or more electron-transport layers to be n-doped. Interlayers which have, for example, an exciton-blocking function and/or control the charge balance in the electroluminescent device may likewise be introduced between two emitting layers. However, it should be pointed out that each of these layers does not necessarily have to be present.

The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013), or systems which have more than three emitting layers. It may also be a hybrid system, where one or more layers fluoresce and one or more other layers phosphoresce.

In a preferred embodiment of the invention, the organic electroluminescent device comprises the compound according to the invention containing structures of the formula (I) or the preferred embodiments indicated above as matrix material, preferably as electron-conducting matrix material in one or more emitting layers, preferably in combination with a further matrix material, preferably a hole-conducting matrix material. An emitting layer comprises at least one emitting compound.

The matrix material employed can in general be all materials which are known for this purpose in accordance with the prior art. The triplet level of the matrix material is preferably higher than the triplet level of the emitter.

Suitable matrix materials for the compounds according to the invention are ketones, phosphine oxides, sulfoxides and sulfones, for example in accordance with WO 2004/013080, WO 2004/093207, WO 2006/005627 or WO 2010/006680, triarylamines, carbazole derivatives, for example CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example in accordance with WO 2007/063754 or WO 2008/056746, indenocarbazole derivatives, for example in accordance with WO 2010/136109 or WO 2011/000455, azacarbazoles, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, diazasilole derivatives, for example in accordance with WO 2010/054729, diazaphosphole derivatives, for example in accordance with WO 2010/054730, triazine derivatives, for example in accordance with WO 2010/015306, WO 2007/063754 or WO 2008/056746, zinc complexes, for example in accordance with EP 652273 or WO 2009/062578, dibenzofuran derivatives, for example in accordance with WO 2009/148015, or bridged carbazole derivatives, for example in accordance with US 2009/0136779, WO 2010/050778, WO 2011/042107 or WO 2011/088877.

It may also be preferred to employ a plurality of different matrix materials as a mixture, in particular at least one electron-conducting matrix material and at least one hole-conducting matrix material. Preference is likewise given to the use of a mixture of a charge-transporting matrix material and an electrically inert matrix material which is not involved or not essentially involved in charge transport, as described, for example, in WO 2010/108579.

It is furthermore preferred to employ a mixture of two or more triplet emitters together with a matrix. The triplet emitter having the shorter-wave emission spectrum serves as co-matrix for the triplet-emitter having the longer-wavelength emission spectrum.

In a preferred embodiment, a compound according to the invention containing structures of the formula (I) can particularly preferably be employed as matrix material in an emission layer of an organic electronic device, in particular in an organic electroluminescent device, for example in an OLED or OLEC. The matrix material comprising a compound containing structures of the formula (I) is present in the electronic device in combination with one or more dopants, preferably phosphorescent dopants.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a further preferred embodiment of the invention, the compound containing structures of the formula (I) is used as a component of mixed-matrix systems. The mixed-matrix systems preferably comprise two or three different matrix materials, particularly preferably two different matrix materials. Preferably, one of the two matrix materials is a material having hole-transporting properties and the other material is a material having electron-transporting properties. The desired electron-transporting and hole-transporting properties of the mixed-matrix components may, however, also be combined mainly or completely in a single mixed-matrix component, where the further mixed-matrix component(s) fulfil(s) other functions. The two different matrix materials here may be present in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. More precise information on mixed-matrix systems is given, inter alia, in the application WO 2010/108579.

Particularly suitable matrix materials which can be used as matrix components of a mixed-matrix system in combination with the compounds according to the invention are selected from the preferred matrix materials for phosphorescent dopants indicated below or the preferred matrix materials for fluorescent dopants, depending on what type of dopant is employed in the mixed-matrix system.

Furthermore, the present invention relates to an electronic device, preferably an organic electroluminescent device, which comprises one or more compounds according to the invention and/or at least one oligomer, polymer or dendrimer according to the invention as electron-conducting compound in one or more electron-conducting layers.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag, may also be used in addition to the said metals, in which case combinations of the metals, such as, for example, Mg/Ag, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). Organic alkali-metal complexes, for example Liq (lithium quinolinate), are likewise suitable for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order either to facilitate irradiation of the organic material (O-SCs) or the coupling-out of light (OLEDs/PLEDs, O-LASERs). Preferred anode materials here are conductive mixed metal oxides. Particular preference is given to indium tin oxide (ITO) or indium zinc oxide (IZO). Preference is furthermore given to conductive, doped organic materials, in particular conductive doped polymers, for example PEDOT, PANI or derivatives of these polymers. It is furthermore preferred for a p-doped hole-transport material to be applied to the anode as hole-injection layer, where suitable p-dopants are metal oxides, for example $MoO_3$ or $WO_3$, or (per)fluorinated electron-deficient aromatic compounds. Further suitable p-dopants are HAT-CN (hexacyanohexaazatriphenylene) or the compound NPD9 from Novaled. A layer of this type simplifies hole injection in materials having a low HOMO, i.e. a large value of the HOMO.

All materials as are used in accordance with the prior art for the layers can generally be used in the further layers, and the person skilled in the art will be able to combine each of these materials with the materials according to the invention in an electronic device without inventive step.

The device is correspondingly structured (depending on the application), provided with contacts and finally hermetically sealed, since the lifetime of such devices is drastically shortened in the presence of water and/or air.

Preference is furthermore given to an electronic device, in particular an organic electroluminescent device, which is characterised in that one or more layers are applied by means of a sublimation process, in which the materials are vapour-deposited in vacuum sublimation units at an initial pressure of usually less than $10^{-5}$ mbar, preferably less than $10^{-6}$ mbar. It is also possible for the initial pressure to be even lower or even higher, for example less than $10^{-7}$ mbar.

Preference is furthermore given to an electronic device, in particular an organic electroluminescent device, which is characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an electronic device, in particular an organic electroluminescent device, which is characterised in that one or more layers are produced from solution, such as, for example, by spin coating, or by means of any desired printing process, such as, for example, screen printing, flexographic printing, offset printing or nozzle printing, but particularly preferably LITI (light induced thermal imaging, thermal transfer printing) or ink-jet printing. Soluble compounds are necessary for this purpose, which are obtained, for example, through suitable substitution.

The electronic device, in particular the organic electroluminescent device, may also be produced as a hybrid system by applying one or more layers from solution and applying one or more other layers by vapour deposition. Thus, for example, it is possible to apply an emitting layer comprising a compound according to the invention containing structures of the formula (I) and a matrix material from solution and to apply a hole-blocking layer and/or an electron-transport layer on top by vacuum vapour deposition.

These processes are generally known to the person skilled in the art and can be applied by him without problems to electronic devices, in particular organic electroluminescent devices, comprising compounds containing structures of the formula (I) or the preferred embodiments indicated above.

The electronic devices according to the invention, in particular organic electroluminescent devices, are distinguished over the prior art by one or more of the following surprising advantages:

1. Electronic devices, in particular organic electroluminescent devices, comprising compounds, oligomers, polymers or dendrimers containing structures of the formula (I), in particular as electron-conducting materials, have a very good lifetime.
2. Compounds, oligomers, polymers or dendrimers containing structures of the formula (I) are distinguished by excellent thermal stability, where compounds having a molar mass of less than about 1200 g/mol are readily sublimable.
3. Compounds, oligomers, polymers or dendrimers containing structures of the formula (I) have very high solubility and form very good films from solutions.
4. Compounds, oligomers, polymers or dendrimers containing structures of the formula (I) exhibit very high redox stability in solution. This greatly simplifies handling, enabling the compounds to be purified and stored very well.
5. Electronic devices, in particular organic electroluminescent devices, comprising compounds, oligomers, polymers or dendrimers containing structures of the formula (I) as electron-conducting materials have excellent efficiency. In particular, the efficiency is significantly higher compared with analogous compounds which do not contain a structural unit of the formula (I).
6. The compounds, oligomers, polymers or dendrimers according to the invention containing structures of the formula (I) exhibit very high stability and result in compounds having a very long lifetime.
7. Compounds, oligomers, polymers or dendrimers containing structures of the formula (I) in electronic devices, in particular organic electroluminescent devices, enable the formation of optical loss channels to be avoided. These devices are consequently distinguished by a high PL efficiency and thus a high EL efficiency of emitters or excellent energy transfer from the matrices to dopants.
8. The use of compounds, oligomers, polymers or dendrimers containing structures of the formula (I) in layers of electronic devices, in particular organic electroluminescent devices, results in high mobility of the electron-conductor structures.
9. Compounds, oligomers, polymers or dendrimers containing structures of the formula (I) have an excellent glass-transition temperature.
10. The compounds, oligomers, polymers or dendrimers containing structures of the formula (I) have a surprisingly high triplet level $T_1$.

These above-mentioned advantages are not accompanied by an impairment of the other electronic properties.

The present invention furthermore relates to the use of a compound according to the invention and/or an oligomer, polymer or dendrimer according to the invention as hole-blocking material, electron-injection material and/or electron-transport material in an electronic device.

It should be pointed out that variations of the embodiments described in the present invention fall within the scope of this invention. Each feature disclosed in the present invention can, unless this is explicitly excluded, be replaced by alternative features which serve the same, an equivalent or a similar purpose. Thus, each feature disclosed in the present invention is, unless stated otherwise, to be regarded as an example of a generic series or as an equivalent or similar feature.

All features of the present invention can be combined with one another in any way, unless certain features and/or steps are mutually exclusive. This applies, in particular, to preferred features of the present invention. Equally, features of non-essential combinations can be used separately (and not in combination).

It should furthermore be pointed out that many of the features, and in particular those of the preferred embodiments of the present invention, are themselves inventive and are not to be regarded merely as part of the embodiments of the present invention. For these features, independent protection can be sought in addition or as an alternative to each invention presently claimed.

The teaching on technical action disclosed with the present invention can be abstracted and combined with other examples.

The invention is explained in greater detail by the following examples, without wishing to restrict them thereby.

The person skilled in the art will be able to use the descriptions to produce further electronic devices according to the invention without inventive step and thus carry out the invention throughout the range claimed.

EXAMPLES

The following syntheses are carried out, unless indicated otherwise, under a protective-gas atmosphere in dried solvents. The solvents and reagents can be purchased, for example, from Sigma-ALDRICH or ABCR. The numbers in square brackets for chemical compounds which are known from the literature relate to the CAS numbers.

A-1) Example 1: Synthesis of Compounds (1-1) to (1-19)

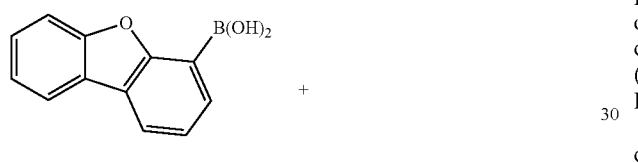

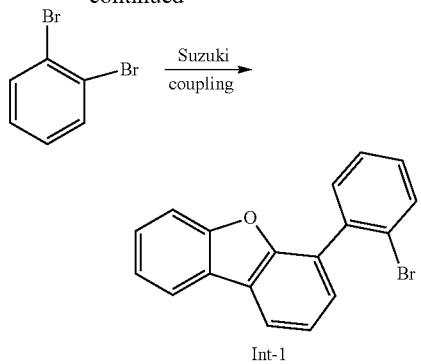

Synthesis of 4-(2-bromophenyl)dibenzofuran Int-1

100 g (462 mmol) of dibenzofuran-4-boronic acid, 106 g (439 mmol) of 1,2-dibromobenzene and 10.7 g (9.2 mmol) of Pd(Ph$_3$P)$_4$ are suspended in 980 ml of dioxane. 979 ml of 2 M potassium carbonate solution are slowly added to this suspension, and the reaction mixture is heated under reflux for 16 h. After cooling, the organic phase is separated off, filtered through silica gel, washed three times with 200 ml of water and subsequently evaporated to dryness. The residue is purified by chromatography on silica gel. Yield: 87 g (270 mmol), 58% of theory, purity according to HPLC>98%.

The following compounds are prepared analogously to the described synthesis of compound Int-1:

| | Starting material 1 | Starting material 2 | Product | Yield |
|---|---|---|---|---|
| Int-2 | 2) [402936-15-6] | | | 62% |
| Int-3 | 2) [162607-19-4] | | | 52% |
| Int-4 | 2) [402936-15-6] | | | 55% |

-continued
| | Starting material 1 | Starting material 2 | Product | Yield |
|---|---|---|---|---|
| Int-5 | 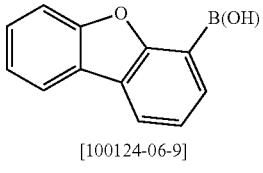 [100124-06-9] | 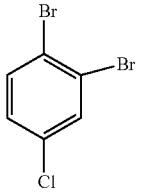 | 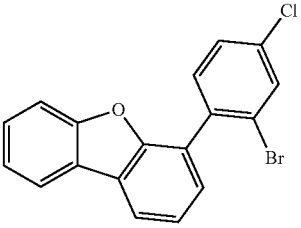 [SMILES: Clc1ccc(-c2cccc3c2oc2ccccc23)c(Br)c1] | 35% |
| Int-6 | 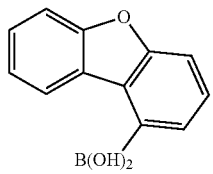 [162607-19-4] | 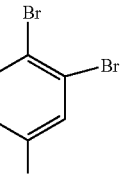 | 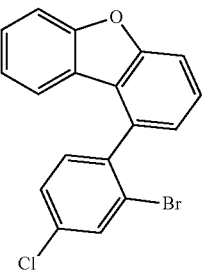 [SMILES: Clc1ccc(-c2cccc3oc4ccccc4c23)c(Br)c1] | 40% |
| Int-7 | 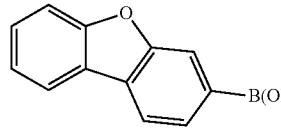 [395087-98-5] | 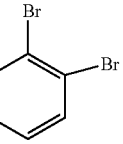 | 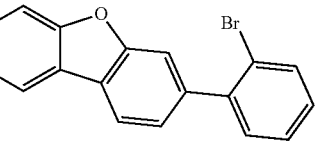 | 43% |
| Int-8 | 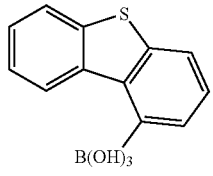 [1245943-60-5] | 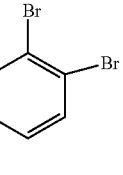 | 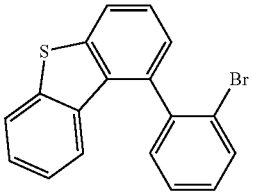 [SMILES: Brc1ccccc1-c1cccc2sc3ccccc3c12] | 42% |
| Int-9 | 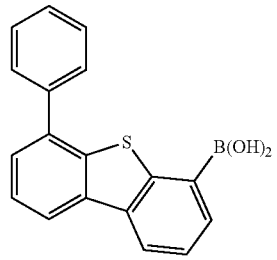 [1115640-18-0] | 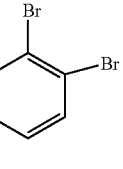 | 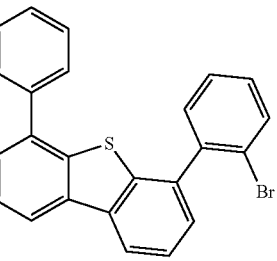 | 40% |

The following compounds are prepared analogously to the described synthesis of compound Int-29.

| | Starting material 1 | Starting material 2 | Product | Yield |
|---|---|---|---|---|
| Int-10 | | [2041-19-2] | | 80% |
| Int-11 | | [216312-73-1] | | 70% |
| Int-12 | | [4269-17-4] | | 70% |

-continued

| | Starting material 1 | Starting material 2 | Product | Yield |
|---|---|---|---|---|
| Int-13 | | [4269-17-4] | | 72% |
| Int-14 | | [486-25-9] | | 75% |
| Int-15 | | [4269-17-4] | | 80% |
| Int-16 | | [3096-49-9] | | 75% |

-continued

| | Starting material 1 | Starting material 2 | Product | Yield |
|---|---|---|---|---|
| Int-17 | (dibenzofuran-Ph with Cl, Br) | 2,7-diphenyl-fluorenone [115033-91-5] | (spiro product) | 73% |
| Int-18 | (dibenzofuran-Ph with Cl, Br) | 4-bromofluorenone [4269-17-4] | (spiro product with Br) | 70% |
| Int-19 | (dibenzofuran-Ph with Cl, Br) | fluorenone [486-25-9] | (spiro product) | 75% |
| Int-20 | (dibenzofuran-Ph with Cl, Br) | 2,7-difluorofluorenone [24313-53-9] | (spiro product with F) | 65% |

-continued
| | Starting material 1 | Starting material 2 | Product | Yield |
|---|---|---|---|---|
| Int-21 | 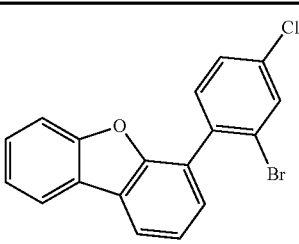 | 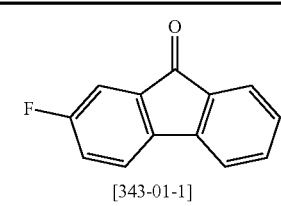 [343-01-1] | 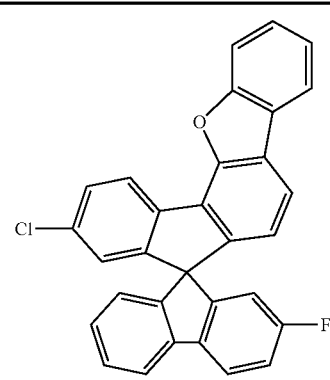 | 58% |
| Int-22 | 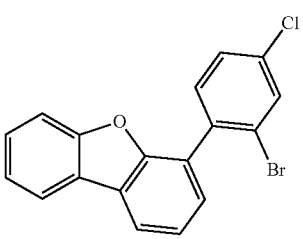 [SMILES: Clc1ccc(-c2cccc3c2oc2ccccc23)c(Br)c1] | 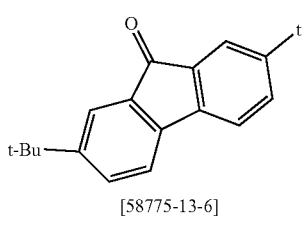 [58775-13-6] | 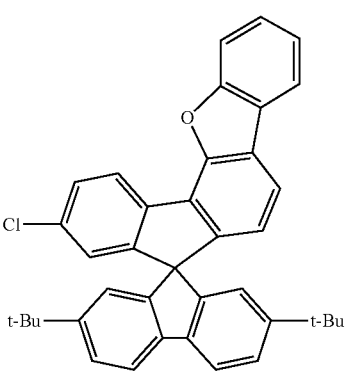 [SMILES: CC(C)(C)c1ccc2c(c1)C1(c3cc(C(C)(C)C)ccc3-2)c2cc(Cl)ccc2-c2c1ccc1c2oc2ccccc21] | 80% |
| Int-23 | 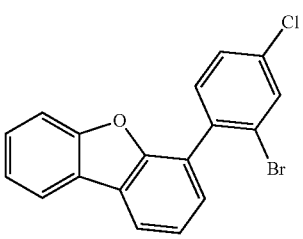 [SMILES: Clc1ccc(-c2cccc3c2oc2ccccc23)c(Br)c1] | 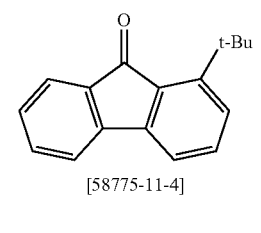 [SMILES: CC(C)(C)c1cccc2c1C(=O)c1ccccc1-2] [58775-11-4] | 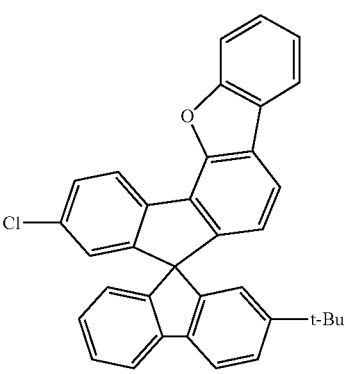 [SMILES: CC(C)(C)c1ccc2c(c1)C1(c3ccccc3-2)c2cc(Cl)ccc2-c2c1ccc1c2oc2ccccc21] | 72% |
| Int-24 | 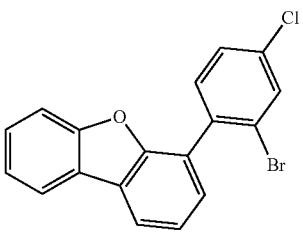 [SMILES: Clc1ccc(-c2cccc3c2oc2ccccc23)c(Br)c1] | 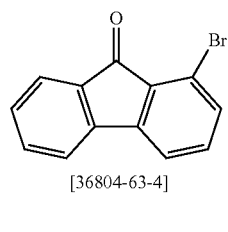 [SMILES: O=C1c2ccccc2-c2cccc(Br)c21] [36804-63-4] | 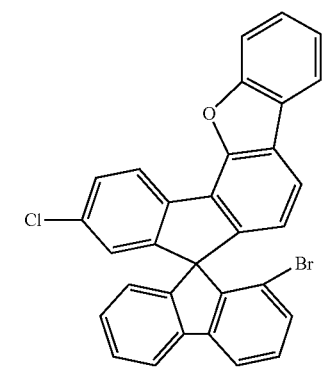 [SMILES: Clc1ccc2c(c1)C1(c3ccccc3-c3cccc(Br)c31)c1ccc3c(oc4ccccc43)c1-2] | 75% |

-continued
| | Starting material 1 | Starting material 2 | Product | Yield |
|---|---|---|---|---|
| Int-25 | 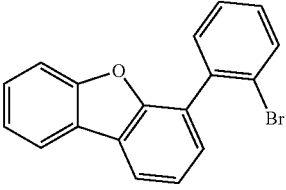 [SMILES: Brc1ccccc1-c1cccc2c1oc1ccccc12] | 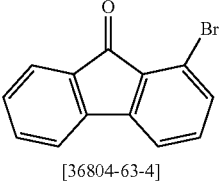 [SMILES: O=C1c2ccccc2-c2cccc(Br)c21][36804-63-4] | 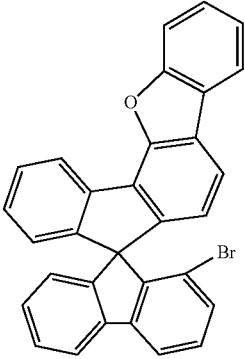 [SMILES: Brc1cccc2c1C1(c3ccccc3-2)c2ccccc2-c2c1ccc1c2oc2ccccc21] | 67% |
| Int-26 | 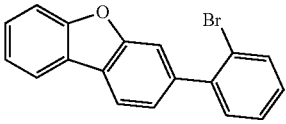 [SMILES: Brc1ccccc1-c1ccc2c(c1)oc1ccccc12] | 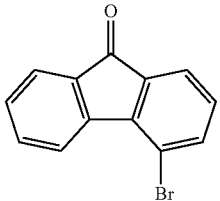[4269-17-4] | 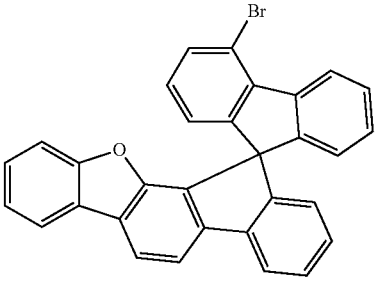 [SMILES: Brc1cccc2c1-c1ccccc1C21c2ccccc2-c2ccc3c(oc4ccccc43)c21] | 59% |
| Int-27 | 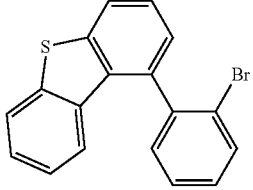 [SMILES: Brc1ccccc1-c1cccc2sc3ccccc3c12] | 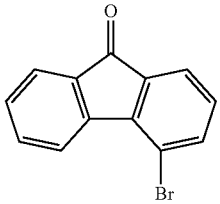[4269-17-4] | 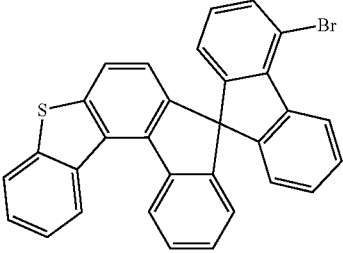 [SMILES: Brc1cccc2c1-c1ccccc1C21c2ccccc2-c2c1ccc1sc3ccccc3c21] | 47% |
| Int-28 | 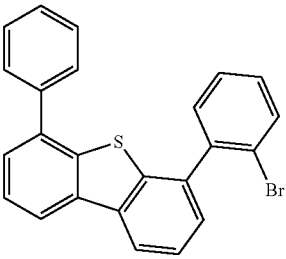 [SMILES: Brc1ccccc1-c1cccc2c1sc1c(-c3ccccc3)cccc12] | 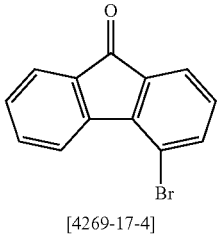 [SMILES: O=C1c2ccccc2-c2c(Br)cccc21][4269-17-4] | 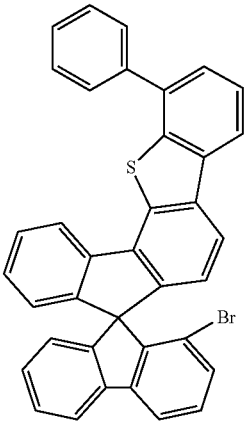 [SMILES: Brc1cccc2c1C1(c3ccccc3-2)c2ccccc2-c2c1ccc1c2sc2c(-c3ccccc3)cccc21] | 51% |

Synthesis of Compound (1-1)

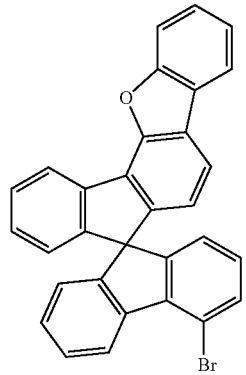 [SMILES: Brc1cccc2c1-c1ccccc1C21c2ccccc2-c2c1ccc1c2oc2ccccc21]

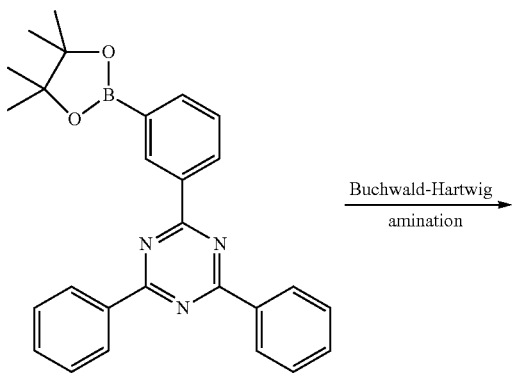

Buchwald-Hartwig amination →

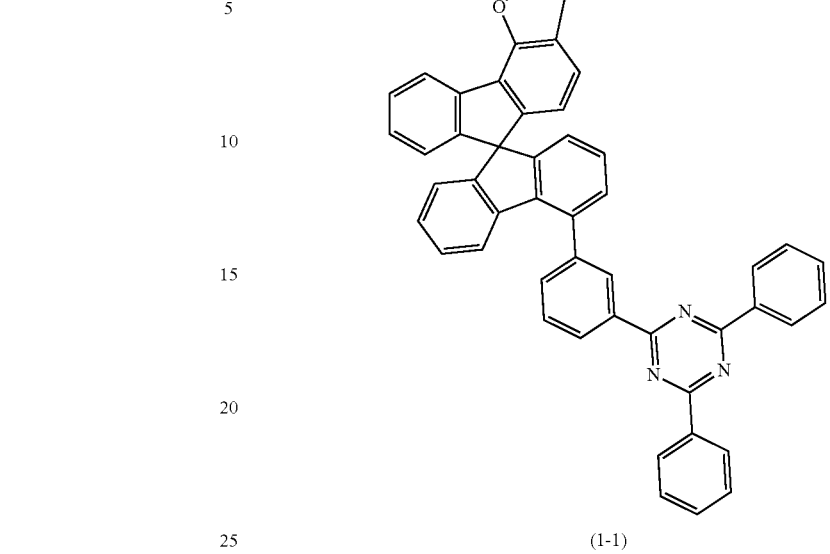

(1-1)

15.5 g (32 mmol) of bromospiro derivative, 15.2 g (35 mmol) of 2,4-diphenyl-6-(3-(4,4,5,5-tetramethyl-1,3,2-dioxaborolanyl)phenyl-1,3,5-triazine dibromodibenzofuran, 31 ml (63 mmol) of $Na_2CO_3$ (2 M solution) are suspended in 120 ml of toluene and 120 ml of ethanol. 0.73 g (0.63 mmol) of $Pd(PPh_3)_4$ is added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from dichloromethane/isopropanol and finally sublimed in a high vacuum ($p=5\times10^{-5}$ mbar). The purity is 99.9% (HPLC). The yield of compound (1-1) is 16.6 g (23 mmol), corresponding to 73% of theory.

Synthesis of Compounds (1-2) to (1-19)

The following compounds (1-2) to (1-19) are also prepared analogously to the synthesis of compound (1-1) described in Example 1:

| | Starting material 1 | Starting material 2 | Product | Yield |
|---|---|---|---|---|
| 1-2 | | | | 74% |

-continued
| | Starting material 1 | Starting material 2 | Product | Yield |
|---|---|---|---|---|
| 1-3 | 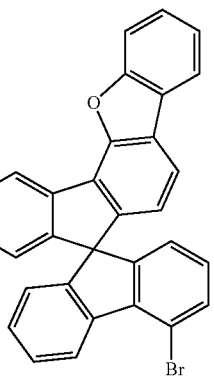 | 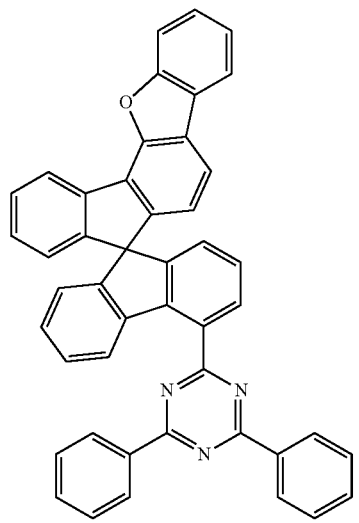 [SMILES: c1ccc(-c2nc(-c3ccccc3)nc(-c3cccc4c3-c3ccccc3C43c4ccccc4-c4c3ccc3c4oc4ccccc43)n2)cc1][1251825-65-6] | 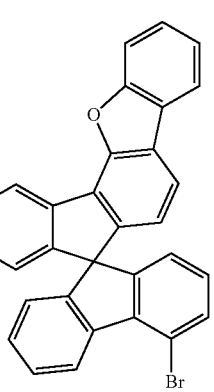 | 81% |
| 1-4 | 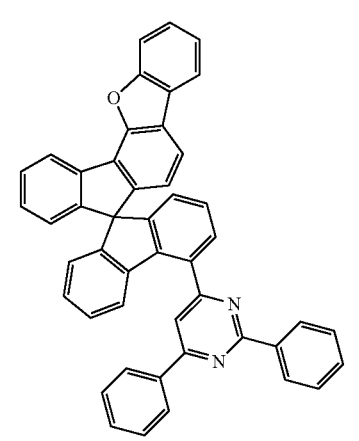 [SMILES: c1ccc(-c2cc(-c3cccc4c3-c3ccccc3C43c4ccccc4-c4c3ccc3c4oc4ccccc43)nc(-c3ccccc3)n2)cc1] | 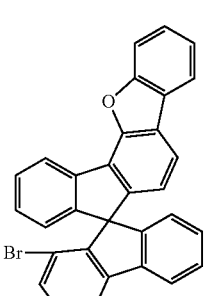[1251825-66-7] | 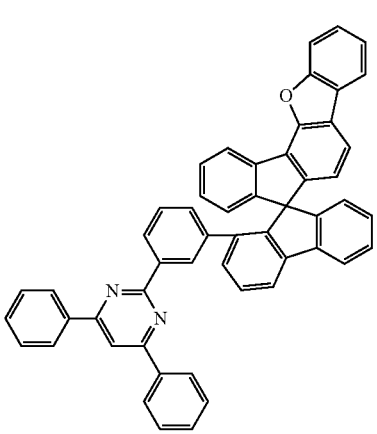 [SMILES: c1ccc(-c2cc(-c3ccccc3)nc(-c3cccc(-c4cccc5c4C4(c6ccccc6-5)c5ccccc5-c5c4ccc4c5oc5ccccc54)c3)n2)cc1] | 84% |
| 1-5 |  | [1381862-91-4] |  | 67% |

-continued
| | Starting material 1 | Starting material 2 | Product | Yield |
|---|---|---|---|---|
| 1-6 | 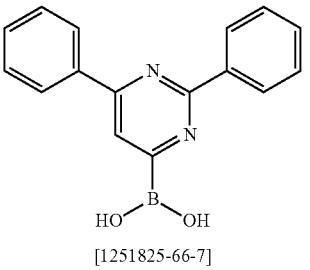 [SMILES: OB(O)c1cc(-c2ccccc2)nc(-c2ccccc2)n1] | 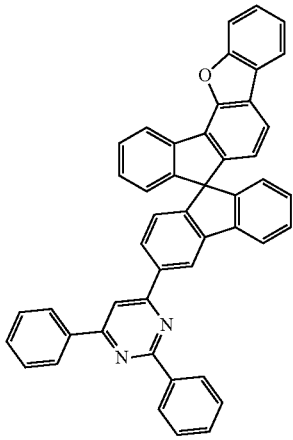 [SMILES: c1ccc(-c2cc(-c3ccc4c(c3)-c3ccccc3C43c4ccccc4-c4c3ccc3c4oc4ccccc43)nc(-c3ccccc3)n2)cc1] [1251825-66-7] | 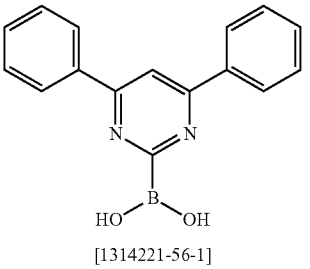 [SMILES: OB(O)c1nc(-c2ccccc2)cc(-c2ccccc2)n1] | 72% |
| 1-7 | 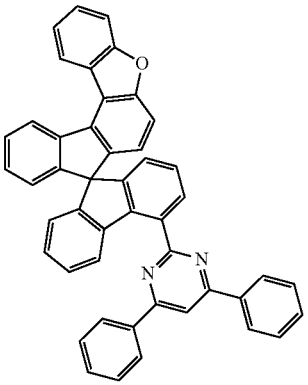 [SMILES: c1ccc(-c2cc(-c3ccccc3)nc(-c3cccc4c3-c3ccccc3C43c4ccccc4-c4c3ccc3oc5ccccc5c43)n2)cc1] | 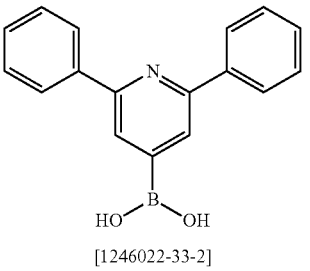 [SMILES: OB(O)c1cc(-c2ccccc2)nc(-c2ccccc2)c1] [1314221-56-1] | 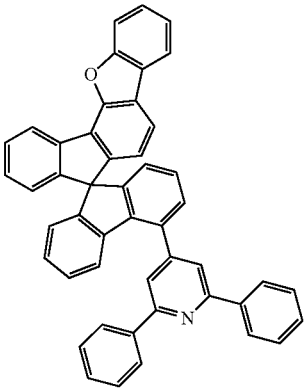 [SMILES: c1ccc(-c2cc(-c3cccc4c3-c3ccccc3C43c4ccccc4-c4c3ccc3c4oc4ccccc43)cc(-c3ccccc3)n2)cc1] | 82% |
| 1-8 | | [1246022-33-2] | | 77% |

-continued

| | Starting material 1 | Starting material 2 | Product | Yield |
|---|---|---|---|---|
| 1-9 | | [1251825-65-6] | | 71% |
| 1-10 | | [867044-33-5] | | 81% |
| 1-11 | | [952514-79-3]<br>2eq. | | 72% |

-continued
| | Starting material 1 | Starting material 2 | Product | Yield |
|---|---|---|---|---|
| 1-12 |  | 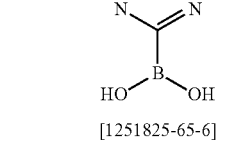  [1251825-65-6] | 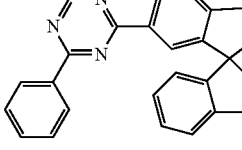 | 70% |
| 1-13 | 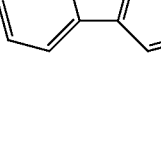 |   [1214723-26-7] |  | 80% |
| 1-14 | 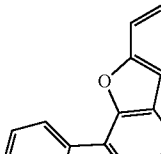 | 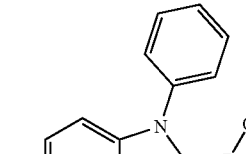  [1251825-65-6] | 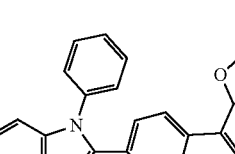 | 76% |
| 1-15 | 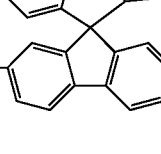 | 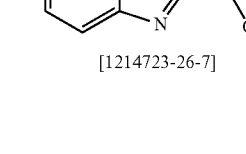  [1251825-65-6] | 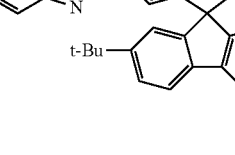 | 70% |

-continued

| | Starting material 1 | Starting material 2 | Product | Yield |
|---|---|---|---|---|
| 1-16 | | [1251825-65-6] | | 66% |
| 1-17 | | [1214723-25-7] | | 72% |
| 1-18 | [1376933-75-3] | [1251825-65-6] | | 76% |

-continued

| Starting material 1 | Starting material 2 | Product | Yield |
|---|---|---|---|
| 1-19 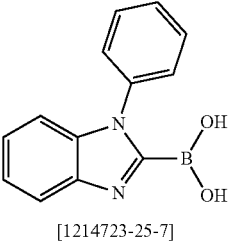 [SMILES: OB(O)c1nc2ccccc2n1-c1ccccc1] | 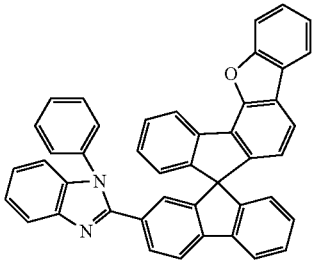 [SMILES: c1ccc(-n2c(-c3ccc4c(c3)C3(c5ccccc5-4)c4ccccc4-c4c3ccc3c4oc4ccccc43)nc3ccccc32)cc1] [1214723-25-7] | 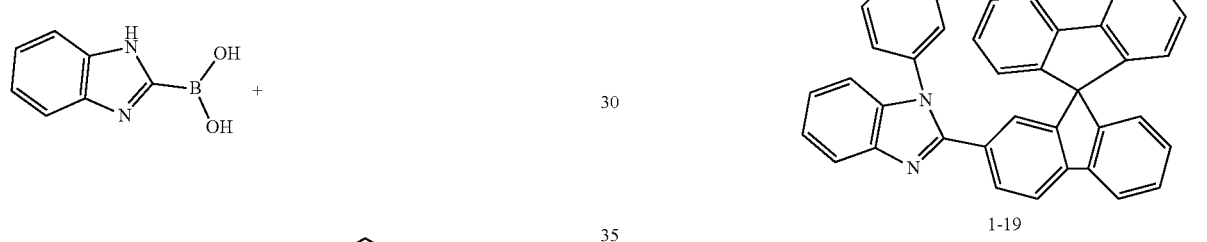 | 77% |

Compound 1-19 can alternatively also be prepared in accordance with the following scheme, in which the unsubstituted benzimidazoleboronic acid is employed in order to obtain compound 1-19a. Step (1) here is carried out analogously to those in the syntheses of compounds 1-1 to 1-19.

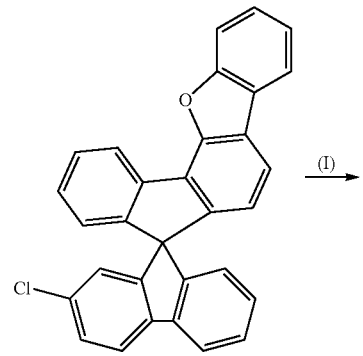

-continued

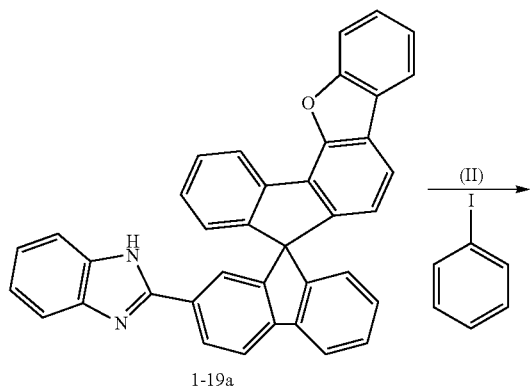

1-19

In step (II), the product from step (I) is reacted with iodobenzene. To this end, 26 g (50 mmol) of compound 1-19a, 560 mg (25 mmol) of Pd(OAc)$_2$, 19.3 g (118 mmol) of CuI, 20.8 g (100 mmol) of iodobenzene are suspended in 300 ml of degassed DMF under protective gas, and the reaction mixture is heated under reflux at 140° C. for 24 h. After the mixture has been cooled, the solvent is removed in vacuo, the residue is dissolved in dichloromethane, and water is added. The organic phase is then separated off and filtered through silica gel. The product is purified by means of column chromatography on silica gel with toluene/heptane (1:2) and finally sublimed in a high vacuum (p=5×10$^{-7}$ mbar) (purity 99.9%). The yield is 18.5 g (30 mmol), corresponding to 62% of theory.

A-2) Example 2: Synthesis of Compounds (2-1) to (2-4)

Synthesis of Intermediate Int-29

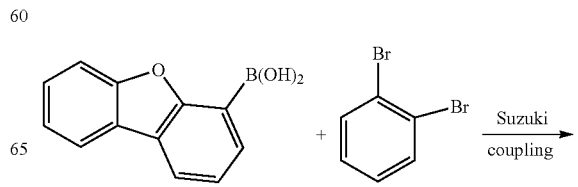

-continued

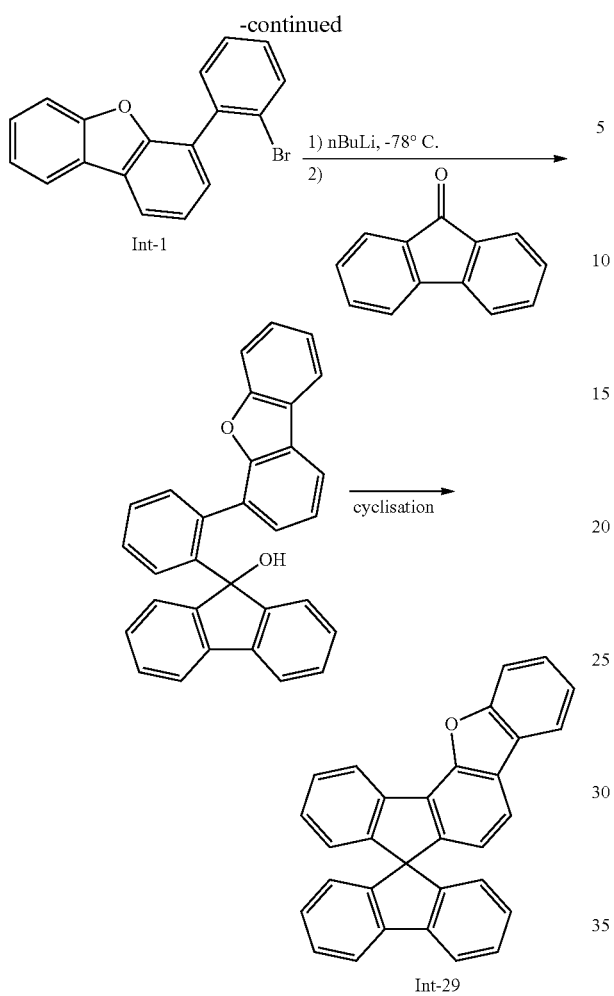

Int-1

Int-29

Synthesis of Compounds (Int-30) to (Int-32)

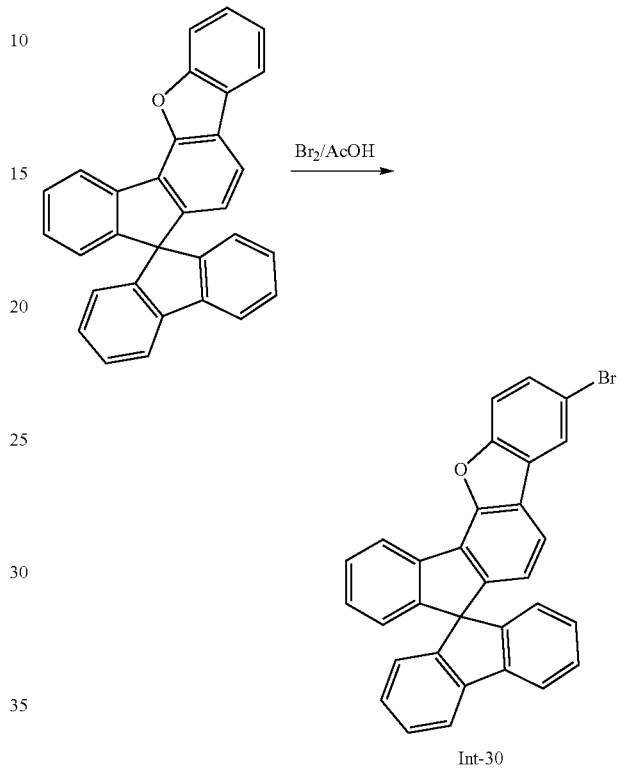

Int-30

31 g (90 mmol) of 4-(2-bromophenyl)dibenzofuran is initially introduced in 300 ml of THF at −78° C. At this temperature, 40 ml of BuLi (2 M in hexane) are added dropwise. After 1 hour, 16.9 g (94 mmol) of fluoren-9-one in 200 ml of THF are added dropwise. The batch is left to stir overnight at room temperature, added to ice-water and extracted with dichloromethane. The combined organic phases are washed with water and dried over sodium sulfate. The solvent is removed in vacuo, and the residue is, without further purification, heated under reflux at 100° C. overnight with 94 ml of HCl and 1074 ml of AcOH. After cooling, the precipitated solid is filtered off with suction, washed once with 100 ml of water, three times with 100 ml of ethanol each time and finally recrystallised from heptane. Yield: 23.1 g (57 mmol), 58%; purity about 98% according to $^1$H-NMR.

15.0 g (36.9 mmol) of a spiro derivative are dissolved in 150 ml of AcOH, and 5.7 g (29 mmol) of bromine dissolved in 20 ml of AcOH are added in portions at room temperature. When the addition is complete, the mixture is heated to 50-60° C., and, when the reaction is complete, water and ethyl acetate are added, and the organic phase is separated off, dried and evaporated. The crude product is subsequently washed by stirring a number of times with hot MeOH/heptane (1:1). Yield: 14.3 g (80%) of the bromospiro derivative Int-30.

The following brominated compounds are prepared analogously:

| Starting material 1 | Bromination reagent | Product | Yield |
|---|---|---|---|
| Int-31 | Br/AcOH | | 58% |

-continued

| Starting material 1 | Bromination reagent | Product | Yield |
|---|---|---|---|
| Int-32 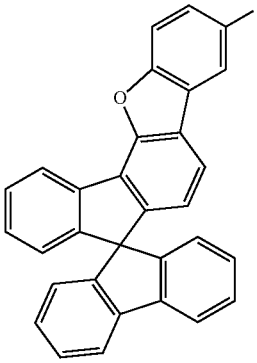 | Br/AcOH | | 55% |

Synthesis of Compounds (Int-33) to (Int-40)

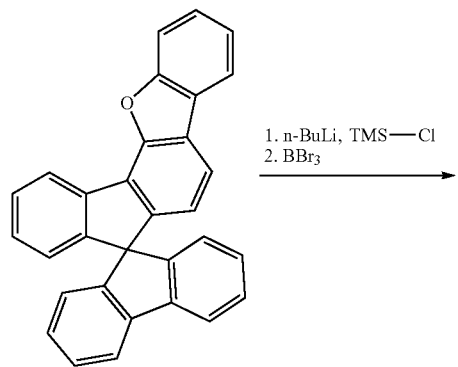

1. n-BuLi, TMS—Cl
2. BBr₃ n-Butyllithium (2.5 M in hexane, 19.7 ml, 49.2 mmol) is added to a solution of 8.0 g (19.7 mmol) of a spiro derivative and 2.93 ml (19.7 mmol) of TMEDA in 100 ml of dried tetrahydrofuran at 0° C. at such a rate that the temperature does not rise above 10° C., and the mixture is subsequently stirred at room temperature for 4 h. The reaction mixture is then cooled to −78° C., chlorotrimethylsilane (7.51 ml, 58.0 mmol) is added, and the mixture is stirred overnight, during which the reaction mixture is allowed to warm to room temperature. The reaction mixture is filtered through a little silica gel and evaporated in a rotary evaporator. The oily residue is dissolved in 100 ml of dried dichloromethane, boron tribromide (2.24 ml, 23.6 mmol) is added, and the mixture is stirred overnight. When the reaction is complete, the reaction mixture is added to ice. The organic phase is separated off, and the aqueous phase is extracted with ethyl acetate. The combined organic phases are dried and evaporated. The cloudy, slightly brownish crude product is reacted further without further purification. Yield: 9.3 g (105%).

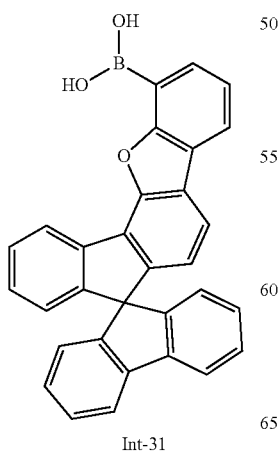

Int-31

The following borylated compounds are prepared analogously. Isomers are separated by chromatography as corresponding pinacol esters:

| Starting material 1 | Reagent | Product 1 | Product 2 |
|---|---|---|---|
| Int-32-33 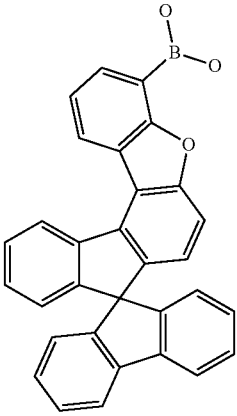 | BuLi/BBr3 | 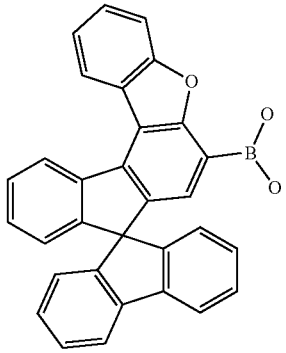 31% | 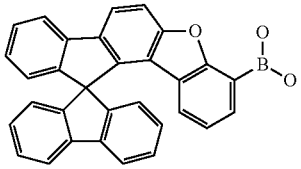 67% |
| Int-34-35 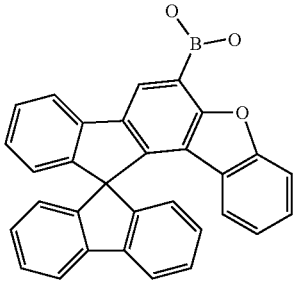 | BuLi/BBr3 | 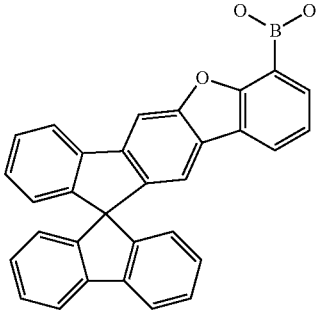 45% | 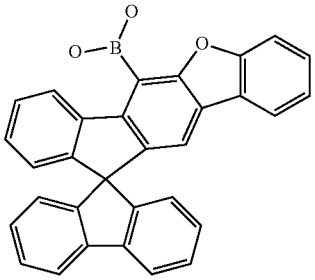 52% |
| Int-36-37 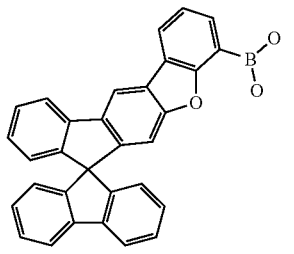 | BuLi/BBr3 | 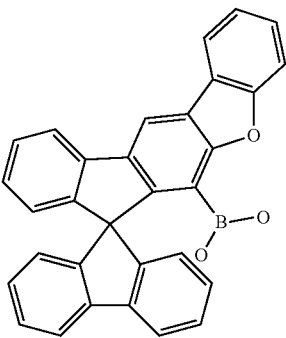 38% | 58% |
| Int-38-39 | BuLi/BBr3 | 77% | 13% |

-continued

| Starting material 1 | Reagent | Product 1 | Product 2 |
|---|---|---|---|
| Int-40 | BuLi/ BBr3 | 94% | |

Synthesis of Compounds (2-1) to (2-4)

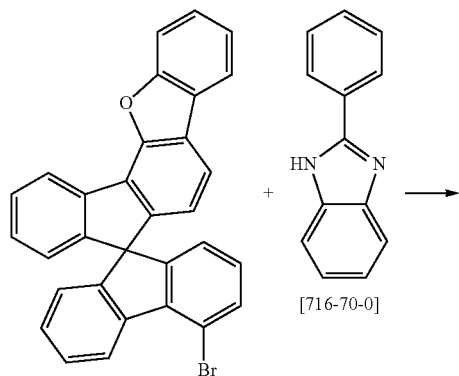

[716-70-0]

39 g (81 mmol) of a bromospiro derivative, 115 g (406 mmol) of 2-phenyl-1-benzimidazole, 22.4 g (162 mmol) of potassium carbonate, 1.84 g (8.1 mmol) of 1,3-di(2-pyridyl)-1,3-propanedione, 1.55 g (8.1 mmol) of copper iodide and 1000 ml of DMF are heated under reflux for 30 h. The reaction mixture is subsequently evaporated to dryness in a rotary evaporator. The residue is dissolved in THF and filtered through a short silica-gel bed, and the solvent is then removed in vacuo. The solid is subsequently recrystallised from heptane/THF and extracted with hot heptane/toluene over aluminium oxide. The solid which precipitated out on cooling is filtered off and dried. The yield of compound (2-1) is 36 g (60 mmol), 75%.

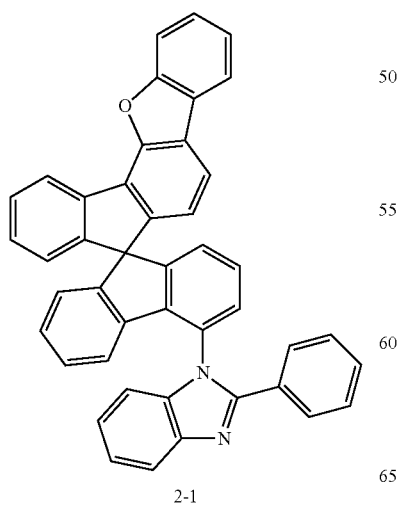

2-1

The following compounds (2-2) to (2-4) are also prepared analogously to the synthesis of compound (2-1) described in Example 2:

| | | Starting | | |
|---|---|---|---|---|
| | Starting material 1 | material 2 | Product | Yield |
| 2-2 | 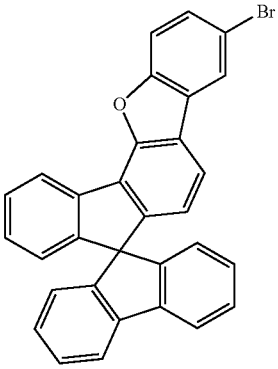 [SMILES: Brc1ccc2oc3c4c(ccc3c2c1)C1(c2ccccc2-c2ccccc21)c1ccccc1-4] | 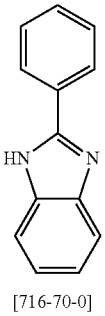
[716-70-0] | 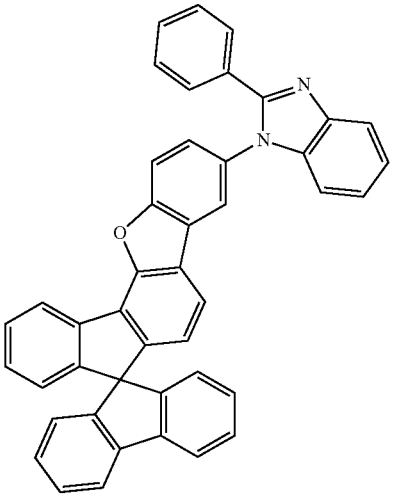 [SMILES: c1ccc(-c2nc3ccccc3n2-c2ccc3oc4c5c(ccc4c3c2)C2(c3ccccc3-c3ccccc32)c2ccccc2-5)cc1] | 82% |
| 2-3 | 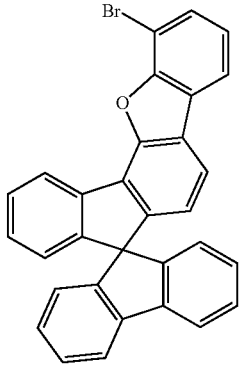 [SMILES: Brc1cccc2c1oc1c3c(ccc12)C1(c2ccccc2-c2ccccc21)c1ccccc1-3] | 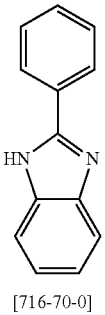 [SMILES: c1ccc(-c2nc3ccccc3[nH]2)cc1]
[716-70-0] | 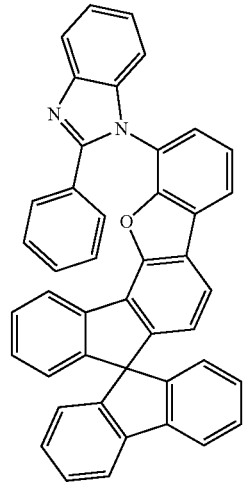 [SMILES: c1ccc(-c2nc3ccccc3n2-c2cccc3c2oc2c4c(ccc23)C2(c3ccccc3-c3ccccc32)c2ccccc2-4)cc1] | 64% |
| 2-4 | 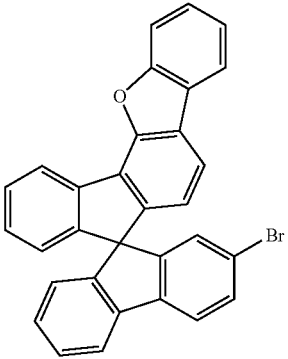
[1376933-75-3] | 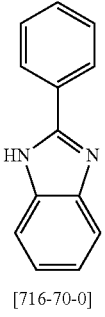
[716-70-0] | 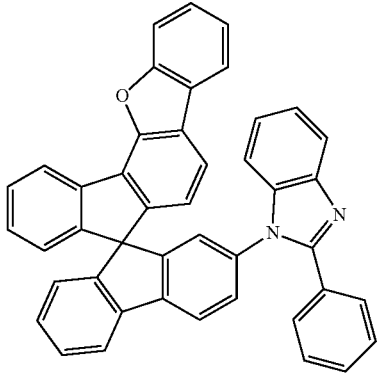 [SMILES: c1ccc(-c2nc3ccccc3n2-c2ccc3c(c2)C2(c4ccccc4-3)c3ccccc3-c3c2ccc2c3oc3ccccc32)cc1] | 68% | vfA-3) Example 3: Synthesis of Compounds 3-1 to 3-5

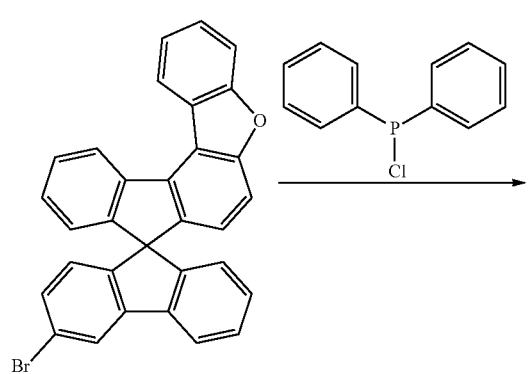

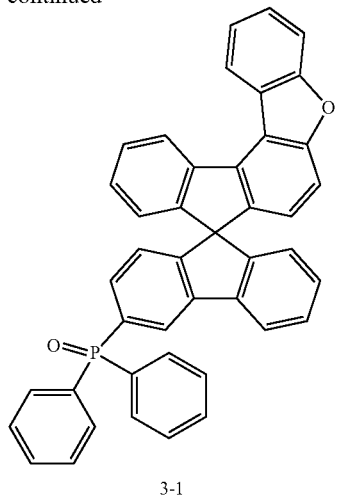

3-1

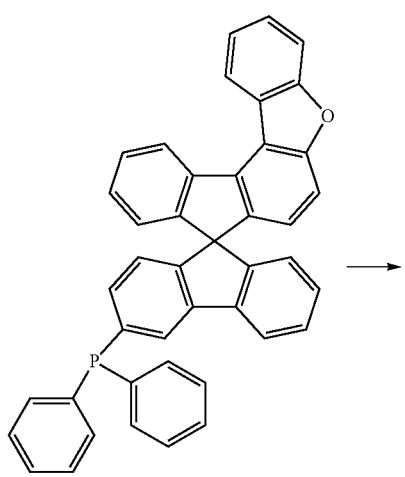

110 ml (276 mmol) of n-butyllithium (2.5 M in hexane) are added dropwise to a solution, cooled to −78° C., of 137 g (270 mmol) of bromospiro derivative in 1500 ml of THF. The reaction mixture is stirred at −78° C. for 30 min. The mixture is allowed to come to room temperature, re-cooled to −78° C., and a mixture of 50 ml (270 mmol) of chlorodiphenylphosphine is then added rapidly, and the mixture is stirred at −70° C. for a further 3 hours. After the mixture has warmed to −10° C., it is hydrolysed using 135 ml of 2 N hydrochloric acid. The organic phase is separated off, washed with water, dried over sodium sulfate and evaporated to dryness. The residue is dissolved in 300 ml of $CH_2Cl_2$ and stirred with 270 ml of 30% hydrogen peroxide solution at room temperature for 12 hours. The organic phase is separated off and evaporated, the colourless solid is filtered off with suction, washed with n-heptane and dried in vacuo and recrystallised from dichloromethane/toluene and finally sublimed in a high vacuum ($p=5\times10^{-5}$ mbar). The purity is 99.9% (HPLC). The yield of compound (3-1) is 119 g (191 mmol), corresponding to 70% of theory.

The following compounds are obtained analogously:

| | Starting material 1 | Starting material 2 | Product | Yield |
|---|---|---|---|---|
| 3-2 | | [1079-66-9] | | 72% |

-continued
| | Starting material 1 | Starting material 2 | Product | Yield |
|---|---|---|---|---|
| 3-3 | 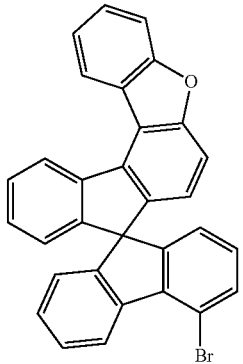 [SMILES: Brc1cccc2c1-c1ccccc1C21c2ccccc2-c2c1ccc1oc3ccccc3c21] | 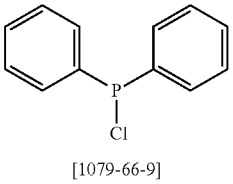 [SMILES: ClP(c1ccccc1)c1ccccc1][1079-66-9] | 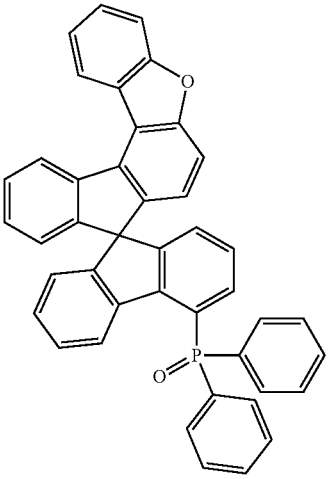 [SMILES: O=P(c1ccccc1)(c1ccccc1)c1cccc2c1-c1ccccc1C21c2ccccc2-c2c1ccc1oc3ccccc3c21] | 69% |
| 3-4 | 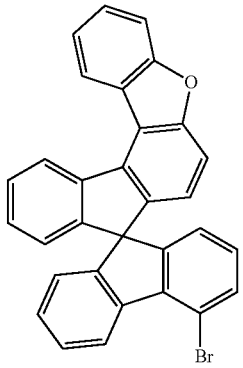 [SMILES: Brc1cccc2c1-c1ccccc1C21c2ccccc2-c2c1ccc1oc3ccccc3c21] | 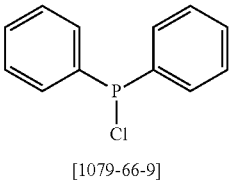 [SMILES: ClP(c1ccccc1)c1ccccc1][1079-66-9] | 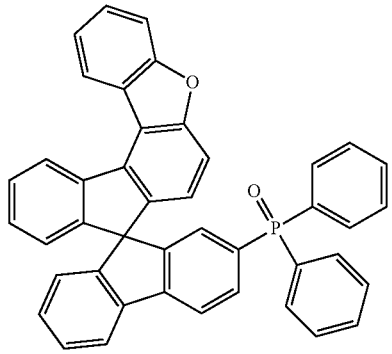 [SMILES: O=P(c1ccccc1)(c1ccccc1)c1ccc2c(c1)C1(c3ccccc3-2)c2ccccc2-c2c1ccc1oc3ccccc3c21] | 72% |
| 3-5 | 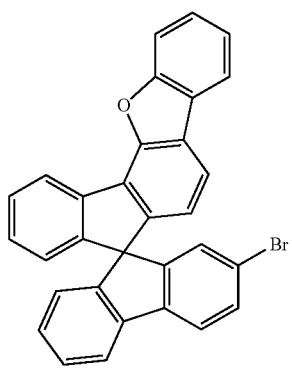 [SMILES: Brc1ccc2c(c1)C1(c3ccccc3-2)c2ccccc2-c2c1ccc1c2oc2ccccc21] | 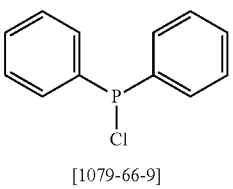 [SMILES: ClP(c1ccccc1)c1ccccc1][1079-66-9] | 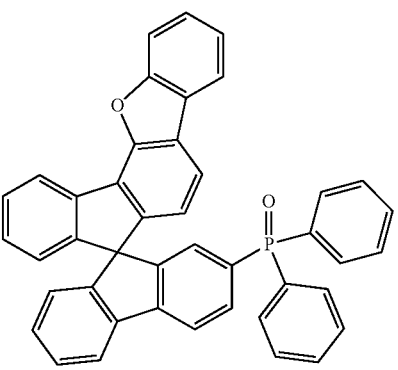 [SMILES: O=P(c1ccccc1)(c1ccccc1)c1ccc2c(c1)C1(c3ccccc3-2)c2ccccc2-c2c1ccc1c2oc2ccccc21] | 73% |

A-4) Example 4: Synthesis of Compounds 4-1 to 4-18

Synthesis of Intermediate Int-41

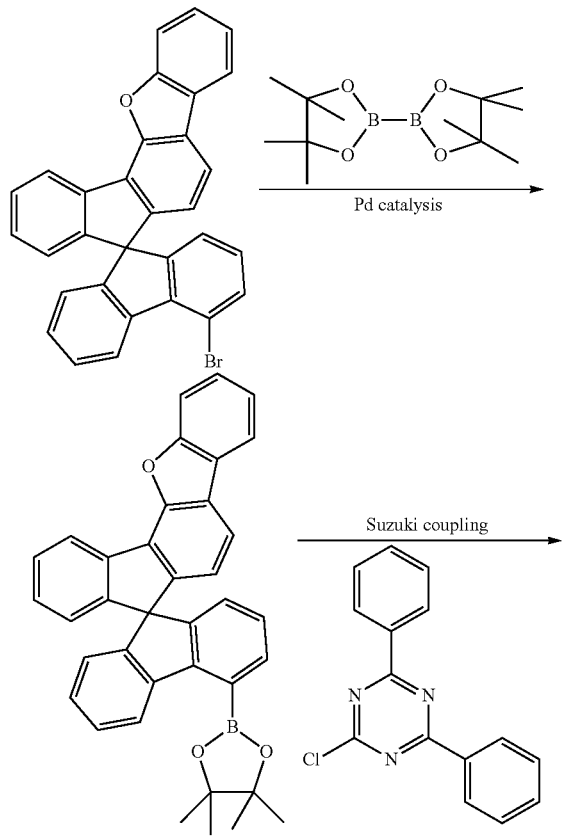

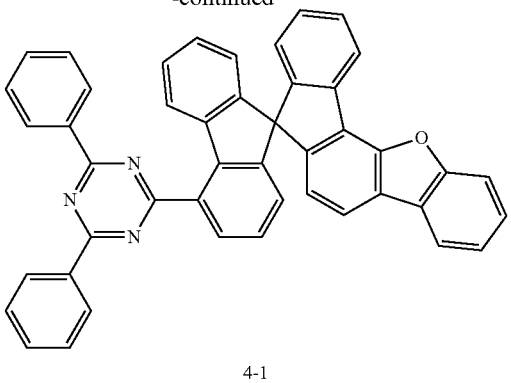

4-1

50 g (103 mmol) of the bromospirofluorene derivative, 32 g (123 mmol) of bis(pinacolato)diborane and 30 g (309 mmol) of potassium acetate are suspended in 800 ml of dioxane. 2.5 g (3.09 mmol) of 1,1-bis(diphenylphosphino)ferrocenepalladium(II) dichloride complex with DCM are added to this suspension. The reaction mixture is heated under reflux for 16 h. After cooling, the organic phase is separated off, washed three times with 400 ml of water and subsequently evaporated to dryness. The residue is recrystallised from toluene (52 g, 95% yield).

The following compounds are prepared analogously:

| | Starting material 1 | Product | Yield |
|---|---|---|---|
| Int-42 | 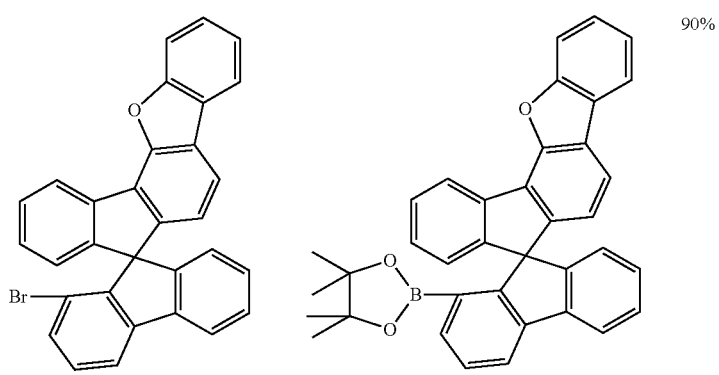 | | 90% |

| Starting material 1 | Product | Yield |
|---|---|---|
| Int-43 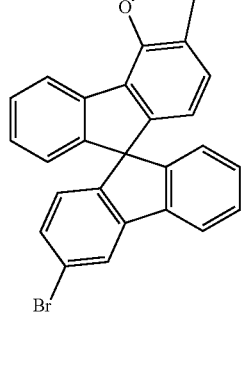 | | 80% |
| Int-44 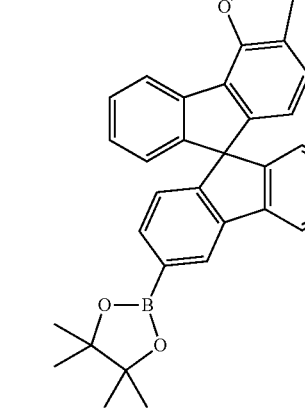 | | 88% |
| Int-45 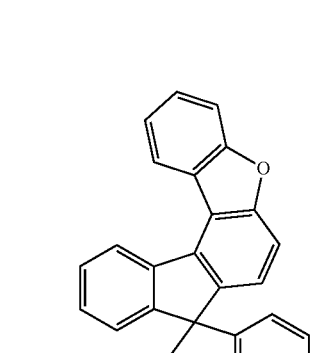 | | 88% |

-continued
| Starting material 1 | | Product | Yield |
|---|---|---|---|
| Int-46 | 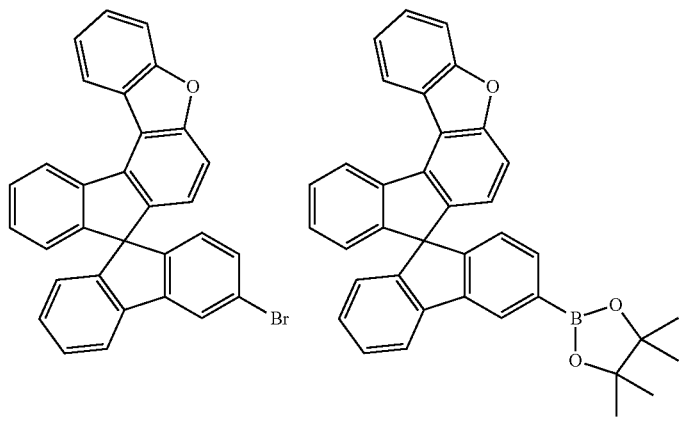 | | 91% |
| Int-47 | 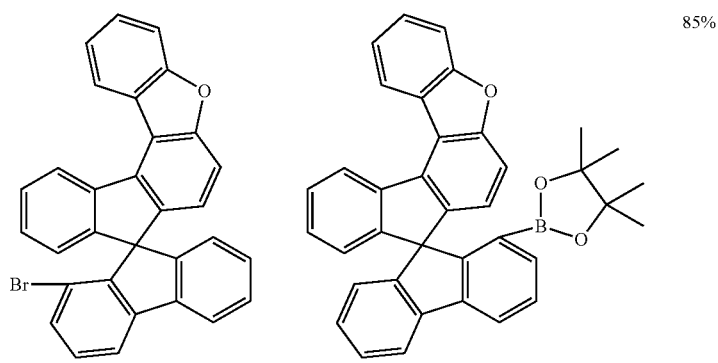 | | 85% |
| Int-48 | 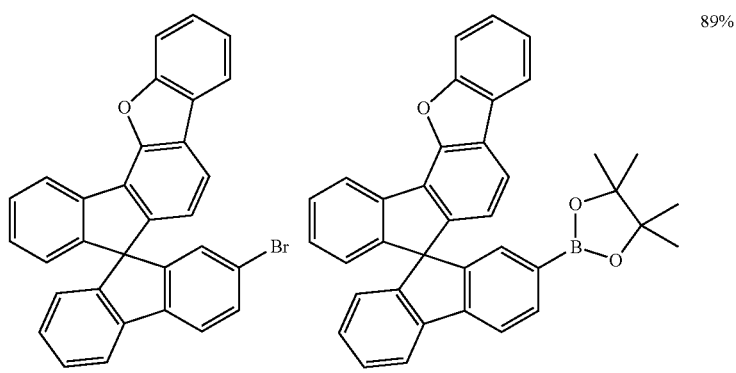 | | 89% |
| [1376933-75-3] | | | |

Synthesis of Compound (4-1)

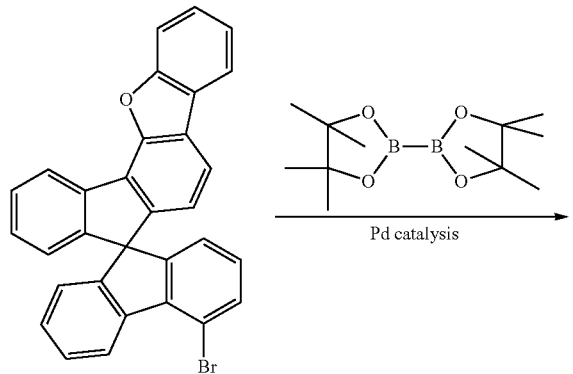

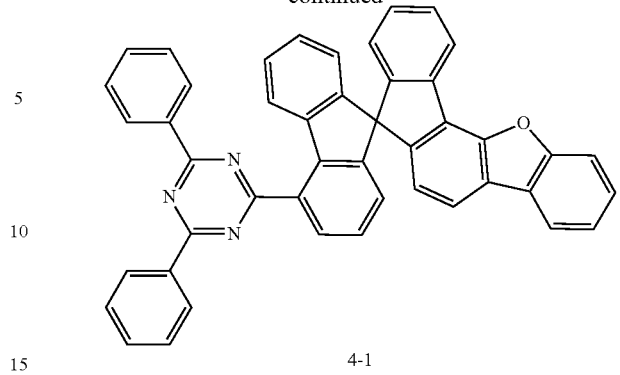

4-1

24.6 g (46.3 mmol) of spirofluorenepinacolboronic ester derivative and 20.0 g (46.3 mmol) of chlorine derivative are suspended in 300 ml of dioxane and 14.1 g of caesium fluoride (92.6 mmol). 4.1 g (5.56 mmol) of bis(tricyclohexylphosphine)palladium dichloride are added to this suspension, and the reaction mixture is heated under reflux for 24 h. After cooling, the organic phase is separated off, filtered through silica gel, washed three times with 100 ml of water and subsequently evaporated to dryness. After the crude product has been filtered through silica gel with toluene, the residue which remains is recrystallised from heptane/toluene and finally sublimed in a high vacuum. The purity is 99.9%. The yield is 29.7 g (80% of theory).

Synthesis of Compounds (4-2) to (4-18)

The following compounds (4-2) to (4-18) are also prepared analogously to the synthesis of compound (4-1) described above:

| | Starting material 1 | Starting material 2 | Product | Yield |
|---|---|---|---|---|
| 4-2 | 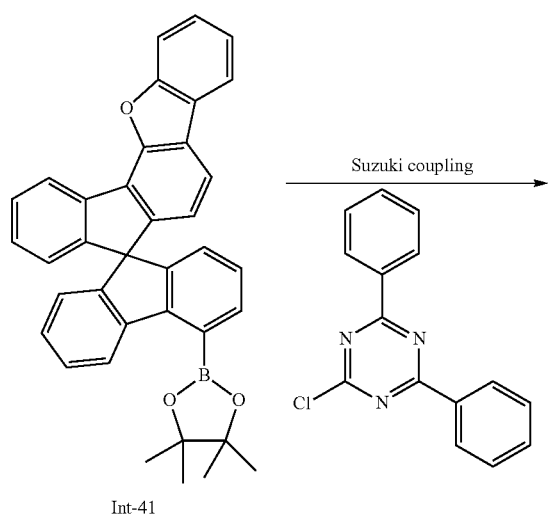 | (structure) [3842-55-5] | (structure) | 78% |

-continued
| | Starting material 1 | Starting material 2 | Product | Yield |
|---|---|---|---|---|
| 4-3 | 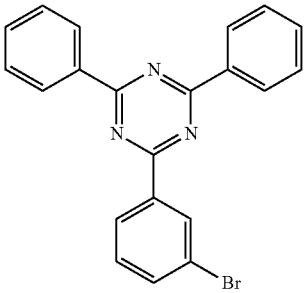 | 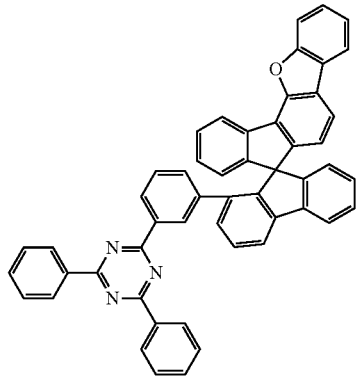 [SMILES: c1ccc(-c2nc(-c3ccccc3)nc(-c3cccc(-c4cccc5c4C4(c6ccccc6-5)c5ccccc5-c5c4ccc4c5oc5ccccc54)c3)n2)cc1] 864377-31-1] | 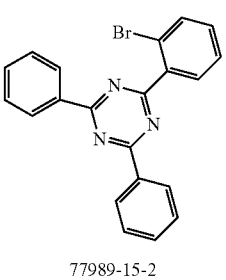 [SMILES: Brc1ccccc1-c1nc(-c2ccccc2)nc(-c2ccccc2)n1] | 71% |
| 4-4 | 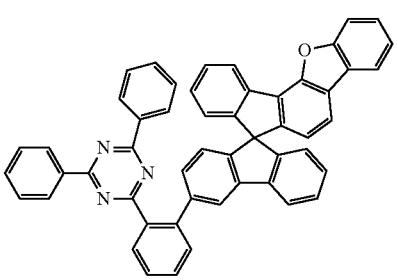 [SMILES: c1ccc(-c2nc(-c3ccccc3)nc(-c3ccccc3-c3ccc4c(c3)-c3ccccc3C43c4ccccc4-c4c3ccc3c4oc4ccccc43)n2)cc1] | 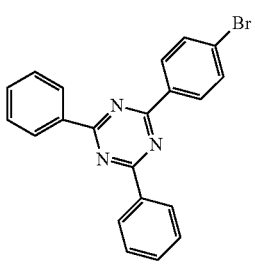 77989-15-2 | 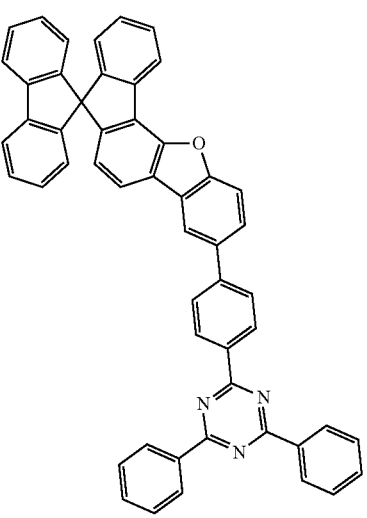 [SMILES: c1ccc(-c2nc(-c3ccccc3)nc(-c3ccc(-c4ccc5oc6c7c(ccc6c5c4)C4(c5ccccc5-c5ccccc54)c4ccccc4-7)cc3)n2)cc1] | 80% |
| 4-5 |  |  23449-08-3 |  | 83% |

-continued

| | Starting material 1 | Starting material 2 | Product | Yield |
|---|---|---|---|---|
| 4-6 | | [864377-22-0] | | 69% |
| 4-7 | | [1418123-78-0] | | 72% |
| 4-8 | | [1379359-00-8] | | 76% |

-continued

| | Starting material 1 | Starting material 2 | Product | Yield |
|---|---|---|---|---|
| 4-9 | | [1379359-00-8] | | 74% |
| 4-10 | | [56181-49-8] | | 73% |
| 4-11 | | [864377-31-1] | | 76% |
| 4-12 | | [3842-55-5] | | 74% |

-continued

| | Starting material 1 | Starting material 2 | Product | Yield |
|---|---|---|---|---|
| 4-13 | | [56181-49-8] | | 71% |
| 4-14 | | [56181-49-8] | | 68% |
| 4-15 | | [864377-31-1] | | 82% |
| 4-16 | | [2620-76-0] | | 83% |

-continued

| | Starting material 1 | Starting material 2 | Product | Yield |
|---|---|---|---|---|
| 4-17 | | [354574-58-6] | | 78% |
| 4-18 | | [354574-58-6] | | 86% |

A-5) Example 5: Synthesis of Compounds 5-1 to 5-5

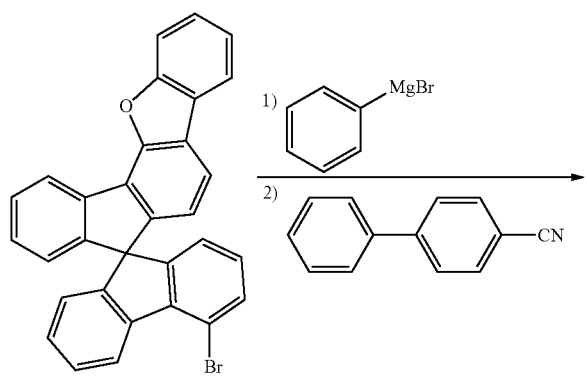

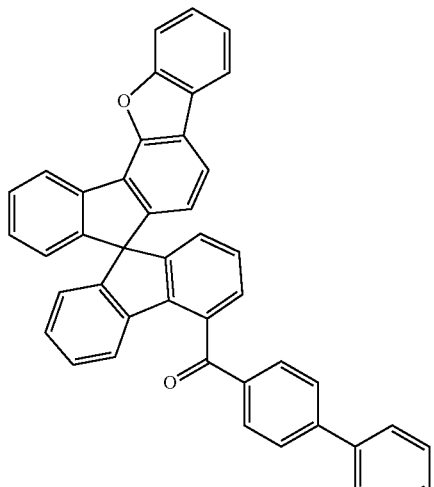

5-1

330 ml of a phenylmagnesium bromide solution (1.0 molar in THF) were added over the course of 15 min. to a suspension of 48.5 g (100 mmol) of bromospirofluorene derivative in 800 ml of THF at room temperature. The mixture was subsequently stirred at room temperature for a further 30 min. and under reflux for 5 h. After cooling, 100 ml of 5 N HCl and 100 ml of ethanol were added, and the mixture was again heated under reflux for 16 h. After cooling, the aqueous phase was separated off, and the organic phase was evaporated to dryness. The residue was taken up in 1000 ml of dichloromethane and washed five times with 500 ml of water each time.

After drying over magnesium sulfate, the organic phase was evaporated to dryness. The residue was recrystallised seven times from DMSO (about 3 ml/g) and dried in vacuo and recrystallised from dichloromethane/toluene and finally sublimed in a high vacuum ($p=5\times10^{-5}$ mbar). The purity is 99.9% (HPLC). The yield of compound (1-1) is 40 g (68 mmol), corresponding to 70% of theory.

Synthesis of Compounds (5-2) to (5-5)

The following compounds (5-2) to (5-5) are also prepared analogously to the synthesis of compound (5-1) described above:

| Starting material 1 | Starting material 2 | Product | Yield |
|---|---|---|---|
| 5-2 | [890134-27-7] | | 69% |
| 5-3 | [67665-48-9] | | 65% |
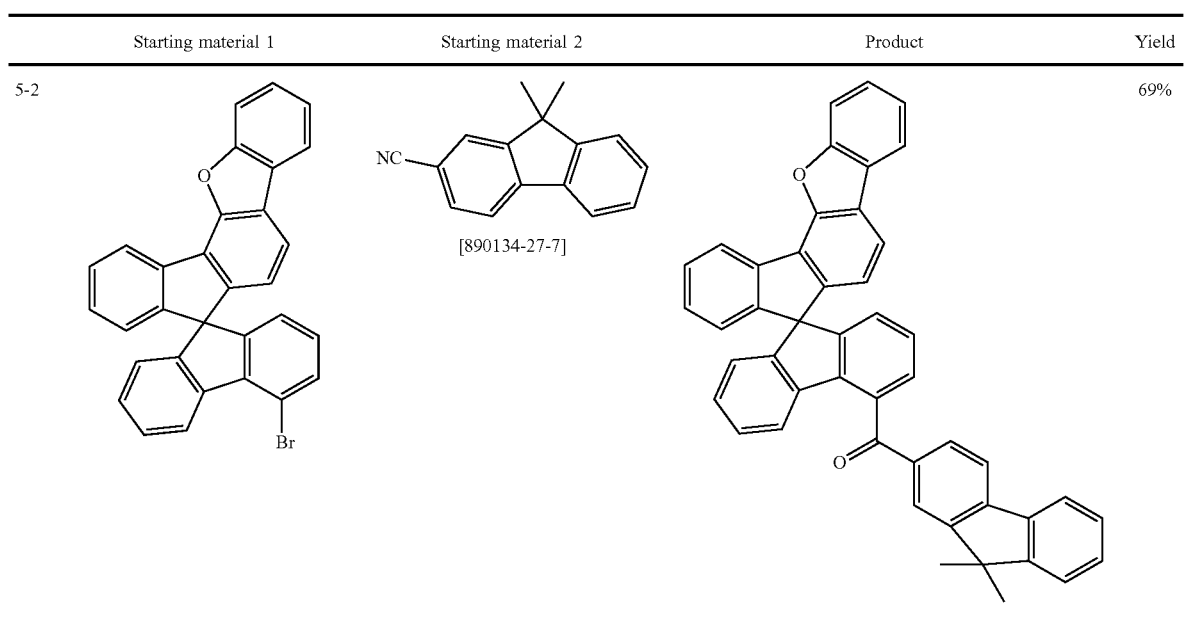
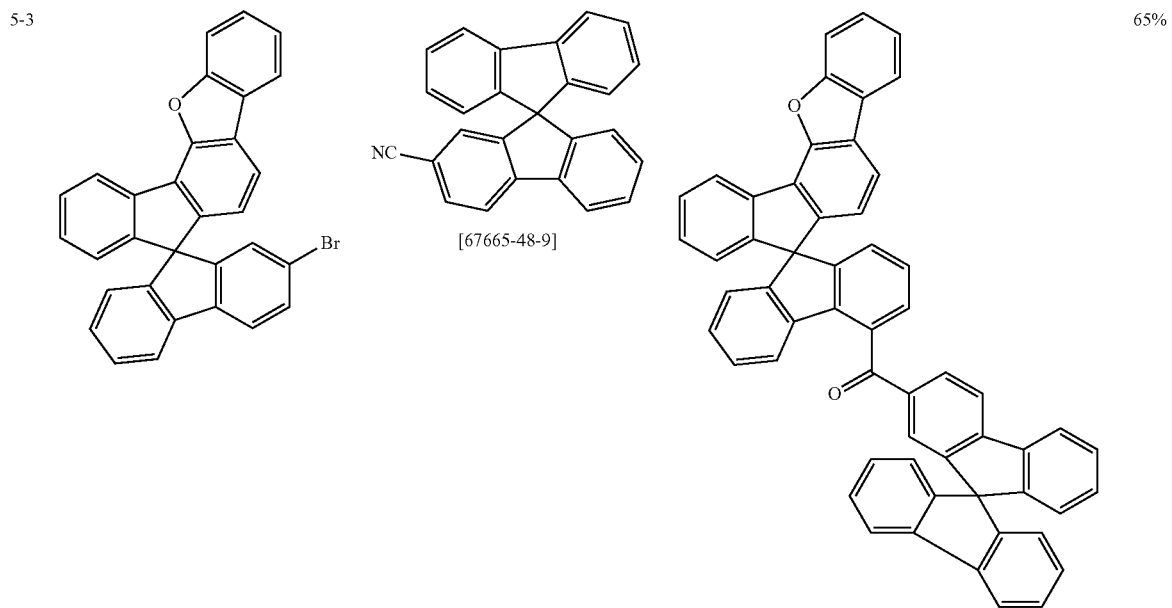

| Starting material 1 | Starting material 2 | Product | Yield |
|---|---|---|---|
| 5-4 | [67665-48-9] | | 72% |
| 5-5 [1376933-75-3] | [67665-48-9] | | 79% |

Production of the OLEDs

The data of various OLEDs are presented in the following Examples V1 to E15 (see Tables 1 and 2).

Pre-treatment for Examples V1 to E15: Glass plates coated with structured ITO (indium tin oxide) in a thickness of 50 nm are coated with 20 nm of PEDOT:PSS (poly(3,4-ethylenedioxythiophene) poly(styrenesulfonate), purchased as CLEVIOS™ P VP AI 4083 from Heraeus Precious Metals GmbH, Germany, applied by spin coating from aqueous solution) for improved processing. These coated glass plates form the substrates to which the OLEDs are applied.

The OLEDs have in principle the following layer structure: substrate/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials required for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by coevaporation. An expression such as IC1:IC3: TEG1 (55%:35%:10%) here means that material IC1 is present in the layer in a proportion by volume of 55%, IC3 is present in the layer in a proportion of 35% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, are determined. The electroluminescence spectra are determined at a luminous density of 1000 cd/m$^2$, and the CIE 1931 x and y colour coordinates are calculated therefrom. The term U1000 in Table 2 denotes the voltage required for a luminous density of 1000 cd/m$^2$.

CE1000 and PE1000 denote the current and power efficiency respectively which are achieved at 1000 cd/m². Finally, EQE1000 denotes the external quantum efficiency at an operating luminous density of 1000 cd/m².

The data of the various OLEDs are summarised in Table 2. Examples V1 and V2 are comparative examples in accordance with the prior art, Examples E1 to E15 show data of OLEDs according to the invention.

Some of the examples are explained in greater detail below in order to illustrate the advantages of the OLEDs according to the invention.

Use of Mixtures According to the Invention in the Emission Layer of Phosphorescent OLEDs The materials according to the invention give rise to significant improvements in the voltage and external quantum efficiency compared with the prior art when used as matrix materials in phosphorescent OLEDs. The use of compounds 1-18 according to the invention in combination with the red-emitting dopant TER1 enables an increase of about 20% to be achieved in the external quantum efficiency compared with the prior art SdT1 (Examples V1 and E2).

Use of Compounds According to the Invention as Electron-Transport Materials

Compared with an OLED in which material SdT2 in accordance with the prior art is used in the ETL, a significant improvement in voltage and power efficiency is observed on use of materials 1-19 according to the invention (Examples V2 and E2).

TABLE 2

Data of the OLEDs

| Ex. | U1000 (V) | CE1000 cd/A | PE1000 lm/W | EQE 1000 | CIE x/y at 1000 cd/m² |
|---|---|---|---|---|---|
| V1 | 5.4 | 12 | 7 | 10.8% | 0.67/0.33 |
| V2 | 3.7 | 69 | 59 | 18.2% | 0.34/0.82 |
| E1 | 4.9 | 14 | 9 | 13.30% | 0.87/0.33 |
| E2 | 3.4 | 67 | 64 | 18.0% | 0.33/0.62 |
| E3 | 3.6 | 61 | 53 | 18.9% | 0.33/0.62 |
| E4 | 3.3 | 63 | 60 | 17.2% | 0.34/0.62 |
| E5 | 3.5 | 64 | 61 | 17.4% | 0.34/0.82 |
| E6 | 3.6 | 66 | 58 | 17.8% | 0.34/0.62 |
| E7 | 3.3 | 64 | 61 | 17.3% | 0.33/0.82 |
| E8 | 3.8 | 55 | 45 | 15.4% | 0.34/0.62 |
| E9 | 3.4 | 58 | 54 | 18.4% | 0.33/0.62 |
| E10 | 3.5 | 60 | 54 | 16.7% | 0.34/0.63 |
| E11 | 3.7 | 61 | 52 | 18.9% | 0.33/0.62 |
| E12 | 3.6 | 56 | 49 | 16.0% | 0.34/0.62 |
| E13 | 5.1 | 15 | 9 | 13.80% | 0.67/0.33 |
| E14 | 3.6 | 66 | 58 | 18.4% | 0.34/0.62 |
| E15 | 3.9 | 60 | 48 | 16.60% | 0.33/0.62 |

TABLE 1

Structure of the OLEDs HTL/IL(HATCN; 5 nm)/EBL/EML/HBL/ETL/EIL

| Ex. | HTL Thickness | EBL Thickness | EML Thickness | HBL Thickness | ETL Thickness | EIL Thickness |
|---|---|---|---|---|---|---|
| V1 | SpA1 90 nm | SpMA1 130 nm | SdT1:TER1 (92% : 8%) 40 nm | — | ST2:LiQ (50% : 50%) 40 nm | — |
| V2 | SpA1 70 nm | SpMA1 90 nm | IC1:TEG1 (90% : 10%) 30 nm | — | SdT2:ST2 (50% : 50%) 40 nm | LiQ 3 nm |
| E1 | SpA1 90 nm | SpMA1 130 nm | 1-18:TER1 (92% : 8%) 30 nm | — | ST2:LiQ (50% : 50%) 30 nm | — |
| E2 | SpA1 70 nm | SpMA1 90 nm | IC1:TEG1 (90% : 10%) 30 nm | — | 1-19:ST2 (50% : 50%) 40 nm | LiQ 3 nm |
| E3 | SpA1 70 nm | SpMA1 90 nm | 4-12:TEG1 (90% : 10%) 30 nm | — | ST2:LiQ (50% : 50%) 40 nm | — |
| E4 | SpA1 70 nm | SpMA1 90 nm | 4-1:TEG1 (90% : 10%) 30 nm | — | ST2:LiQ (50% : 50%) 40 nm | — |
| E5 | SpA1 70 nm | SpMA1 90 nm | 1-1:TEG1 (90% : 10%) 30 nm | — | ST2:LiQ (50% : 50%) 40 nm | — |
| E6 | SpA1 70 nm | SpMA1 90 nm | 1-5:TEG1 (90% : 10%) 30 nm | — | ST2:LiQ (50% : 50%) 40 nm | — |
| E7 | SpA1 70 nm | SpMA1 90 nm | 1-7:TEG1 (90% : 10%) 30 nm | — | ST2:LiQ (50% : 50%) 40 nm | — |
| E8 | SpA1 70 nm | SOW 90 nm | 1-9 TEG1 (90% : 10%) 30 nm | — | ST2:LiQ (50% : 50%) 40 nm | — |
| E9 | SpA1 70 nm | SpMA1 90 nm | IC1 :TEG1 (90% : 10%) 130 nm | — | 1-11:ST2 (50% : 50%) 40 nm | LiF 1 nm |
| E10 | SpA1 70 nm | SpMA1 90 nm | 1-14:IC3:TEG1 (45% : 45% : 10%) 30 nm | IC1 10 nm | ST2:LiQ (50% : 50%) 30 nm | — |
| E11 | SpA1 70 nm | SpMA1 90 nm | 1-15:IC3:TEG1 (45% : 45% : 10%) 30 nm | IC1 10 nm | ST2:LiQ (50% : 50%) 30 nm | — |
| E12 | SpA1 70 nm | SpMA1 90 nm | IC1:3-3:TEG1 (45% : 45% : 10%) 30 nm | IC1 10 nm | ST2:LiQ (50% : 50%) 30 nm | — |
| E13 | SpA1 90 nm | SpMA1 130 nm | 4-3:TER1 (92% : 8%) 30 nm | — | ST2:LiQ (50% : 50%) 30 nm | — |
| E14 | SpA1 70 nm | SpMA1 30 nm | IC1:TEG1 (90% : 10%) 30 nm | — | 4-5:LiQ (50% : 50%) 40 nm | — |
| E15 | SpA1 70 nm | SpMA1 90 nm | 4-11:TEG1 (90% : 10%) 30 nm | — | ST2:LiQ (50% : 50%) 40 nm | — |

TABLE 3
Structural formulae of the materials for the OLEDs
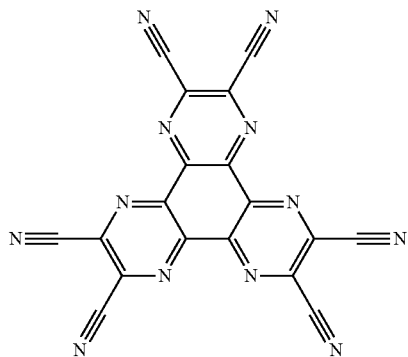 [SMILES: N#Cc1nc2c3nc(C#N)c(C#N)nc3c3nc(C#N)c(C#N)nc3c2nc1C#N] HATCN
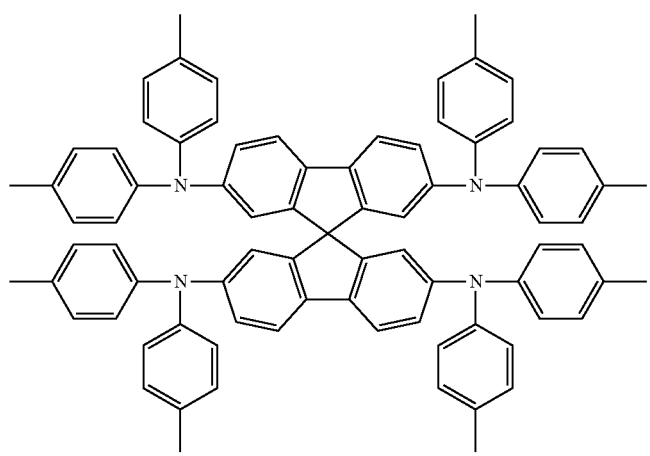 SpA1
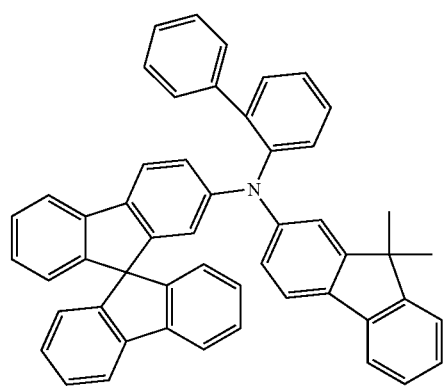 [SMILES: CC1(C)c2ccccc2-c2ccc(N(c3ccc4c(c3)C3(c5ccccc5-c5ccccc53)c3ccccc3-4)c3ccccc3-c3ccccc3)cc21] SpMA1
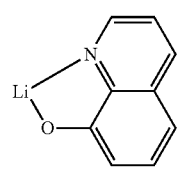 LiQ 187
TABLE 3-continued
Structural formulae of the materials for the OLEDs
SpMA2
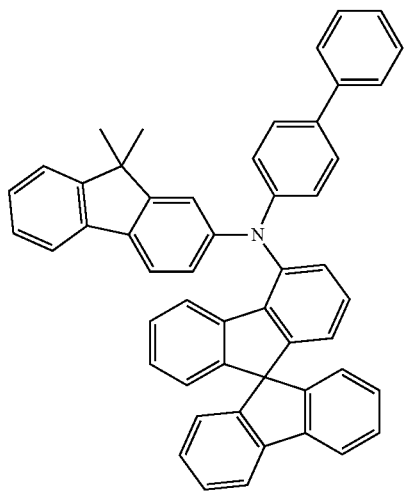 [SMILES: CC1(C)c2ccccc2-c2ccc(N(c3ccc(-c4ccccc4)cc3)c3cccc4c3-c3ccccc3C43c4ccccc4-c4ccccc43)cc21]
TEY1
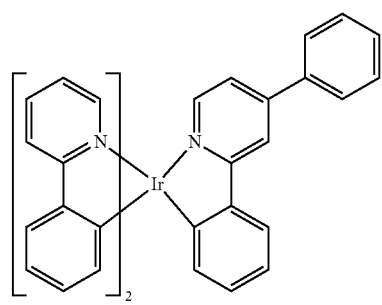
IC2
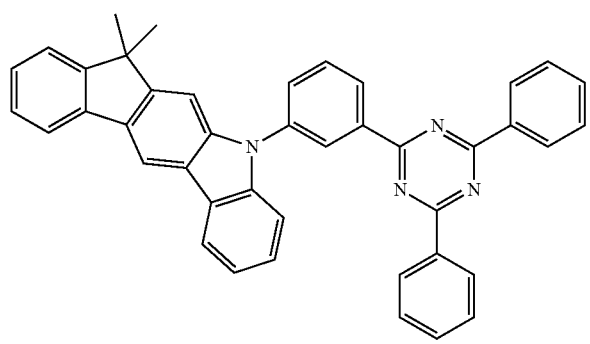 [SMILES: CC1(C)c2ccccc2-c2cc3c4ccccc4n(-c4cccc(-c5nc(-c6ccccc6)nc(-c6ccccc6)n5)c4)c3cc21]

TABLE 3-continued
Structural formulae of the materials for the OLEDs
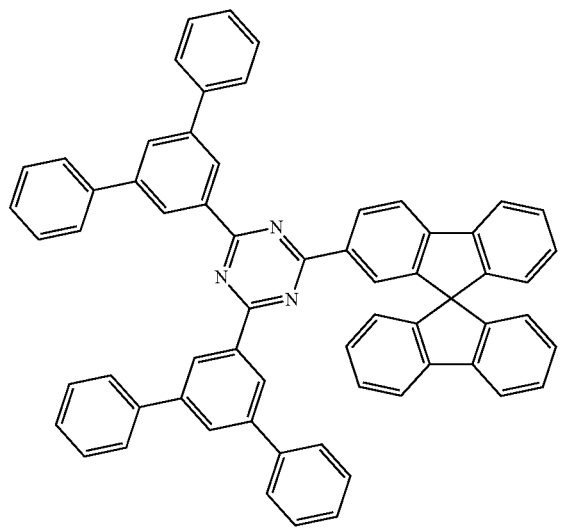 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
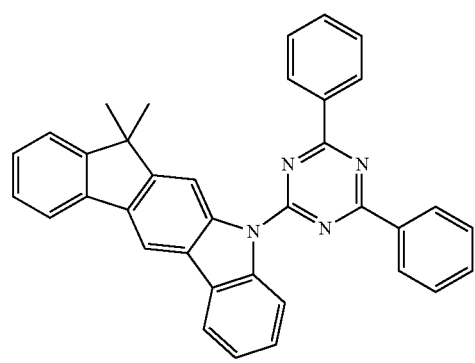 [SMILES: CC1(C)c2ccccc2-c2cc3c4ccccc4n(-c4nc(-c5ccccc5)nc(-c5ccccc5)n4)c3cc21]
IC1
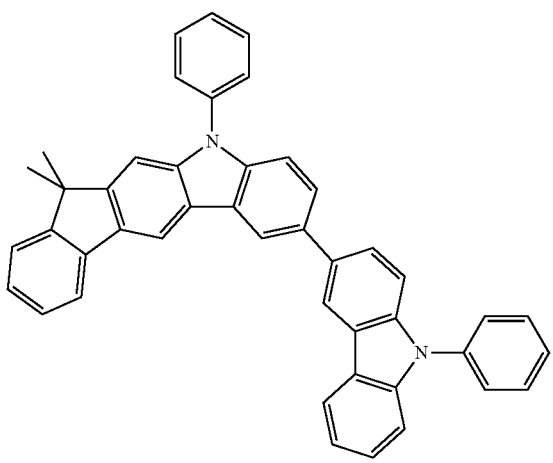 [SMILES: CC1(C)c2ccccc2-c2cc3c4cc(-c5ccc6c(c5)c5ccccc5n6-c5ccccc5)ccc4n(-c4ccccc4)c3cc21]
IC3

TABLE 3-continued
Structural formulae of the materials for the OLEDs
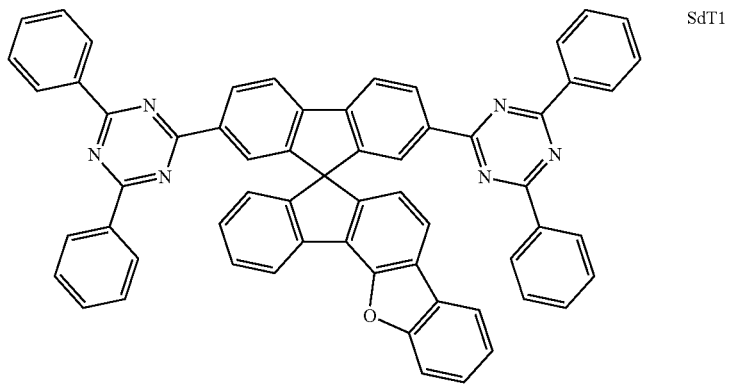 SdT1
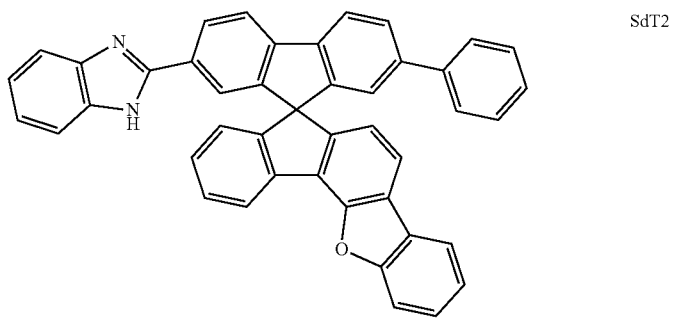 SdT2
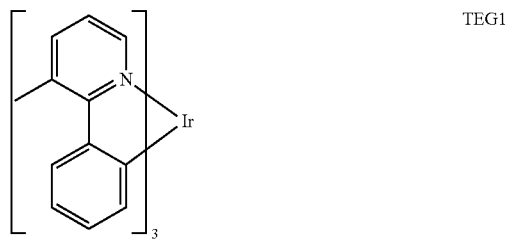 TEG1
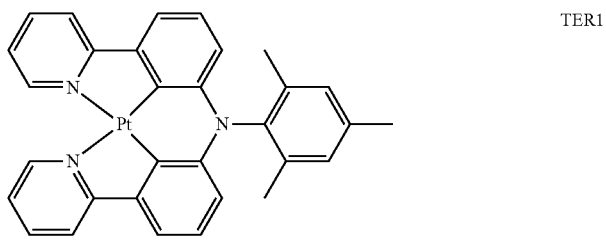 TER1
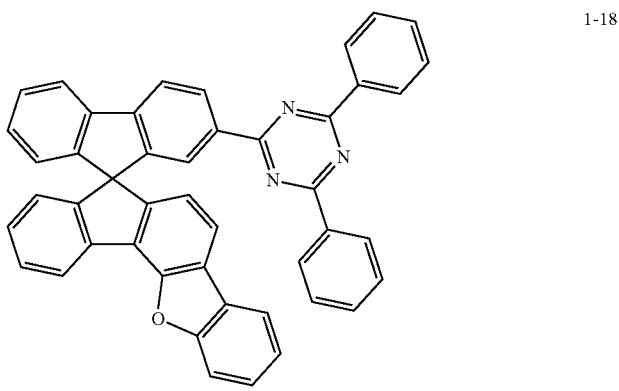 1-18

TABLE 3-continued
Structural formulae of the materials for the OLEDs
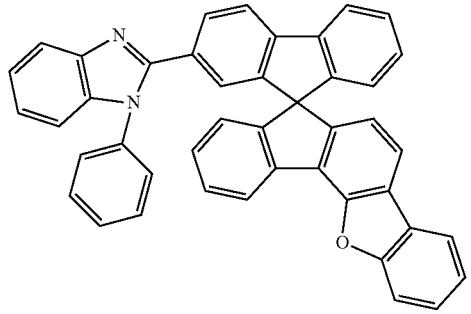 [SMILES: c1ccc(-n2c(-c3ccc4c(c3)C3(c5ccccc5-4)c4ccccc4-c4c3ccc3c4oc4ccccc43)nc3ccccc32)cc1]
1-19
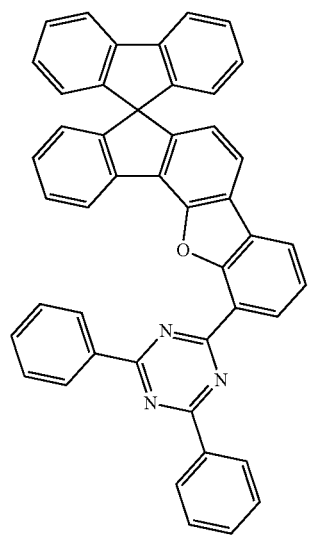 [SMILES: c1ccc(-c2nc(-c3ccccc3)nc(-c3cccc4c3oc3c5c(ccc34)C3(c4ccccc4-c4ccccc43)c3ccccc3-5)n2)cc1]
4-12
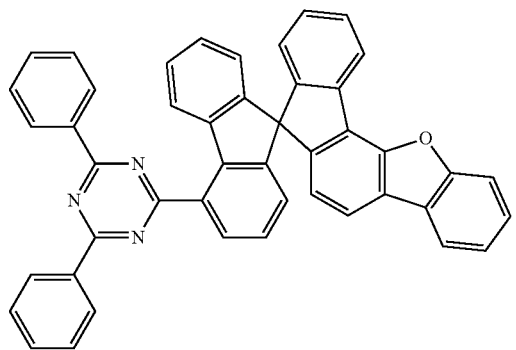 [SMILES: c1ccc(-c2nc(-c3ccccc3)nc(-c3cccc4c3-c3ccccc3C43c4ccccc4-c4c3ccc3c4oc4ccccc43)n2)cc1]
4-1

TABLE 3-continued
Structural formulae of the materials for the OLEDs
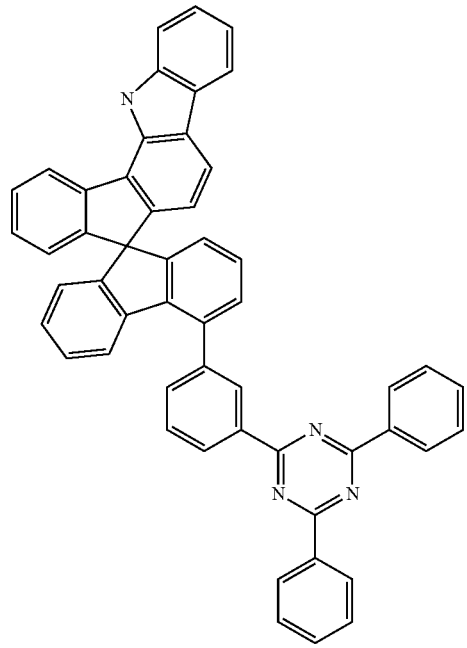 [SMILES: c1ccc(-c2nc(-c3ccccc3)nc(-c3cccc(-c4cccc5c4-c4ccccc4C54c5ccccc5-c5c4ccc4c5[nH]c5ccccc54)c3)n2)cc1]
1-1
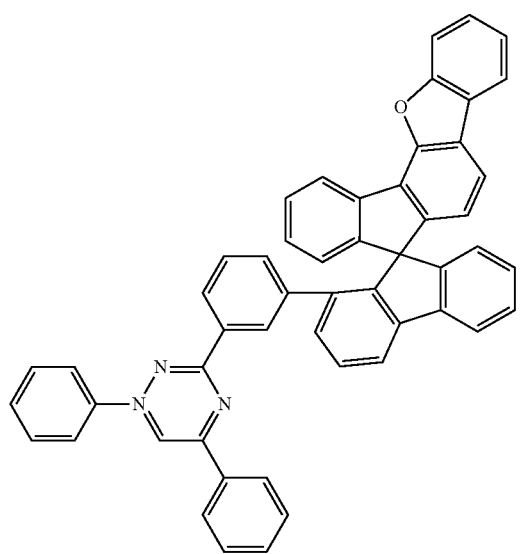
1-5

TABLE 3-continued
Structural formulae of the materials for the OLEDs
1-7
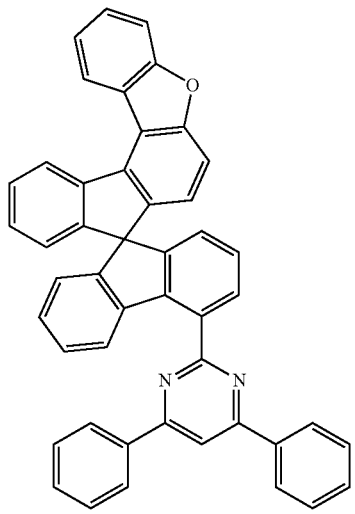 [SMILES: c1ccc(-c2cc(-c3ccccc3)nc(-c3cccc4c3-c3ccccc3C43c4ccccc4-c4c3ccc3oc5ccccc5c43)n2)cc1]
1-9
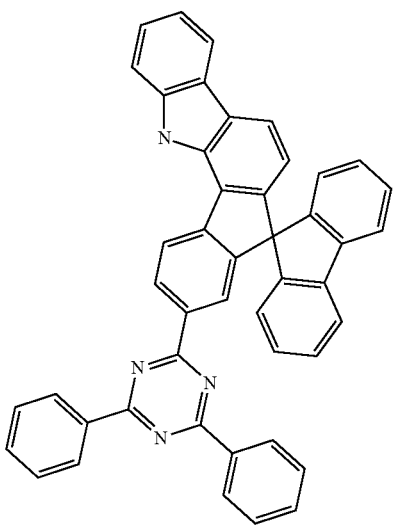 [SMILES: c1ccc(-c2nc(-c3ccccc3)nc(-c3ccc4c(c3)C3(c5ccccc5-c5ccccc53)c3ccc5c([nH]c6ccccc65)c3-4)n2)cc1]
1-11
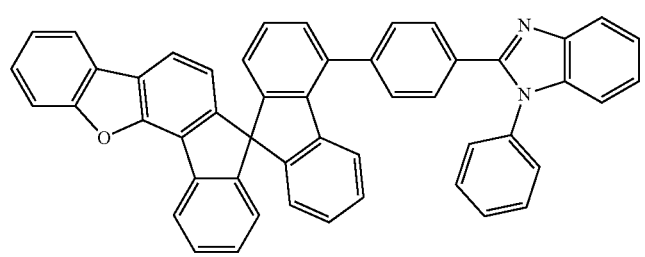 [SMILES: c1ccc(-n2c(-c3ccc(-c4cccc5c4-c4ccccc4C54c5ccccc5-c5c4ccc4c5oc5ccccc54)cc3)nc3ccccc32)cc1]

TABLE 3-continued
Structural formulae of the materials for the OLEDs
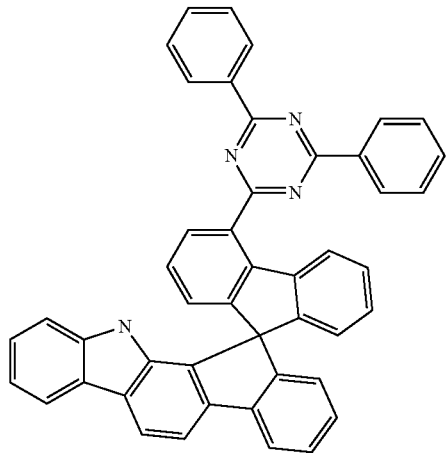 [SMILES: c1ccc(-c2nc(-c3ccccc3)nc(-c3cccc4c3-c3ccccc3C43c4ccccc4-c4ccc5c([nH]c6ccccc65)c43)n2)cc1]
1-14
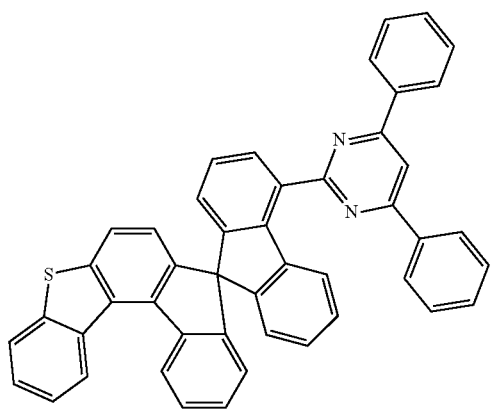 [SMILES: c1ccc(-c2cc(-c3ccccc3)nc(-c3cccc4c3-c3ccccc3C43c4ccccc4-c4c3ccc3sc5ccccc5c43)n2)cc1]
1-15
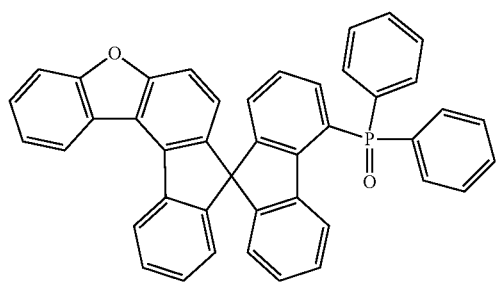 [SMILES: O=P(c1ccccc1)(c1ccccc1)c1cccc2c1-c1ccccc1C21c2ccccc2-c2c1ccc1oc3ccccc3c21]
3-3

TABLE 3-continued
Structural formulae of the materials for the OLEDs
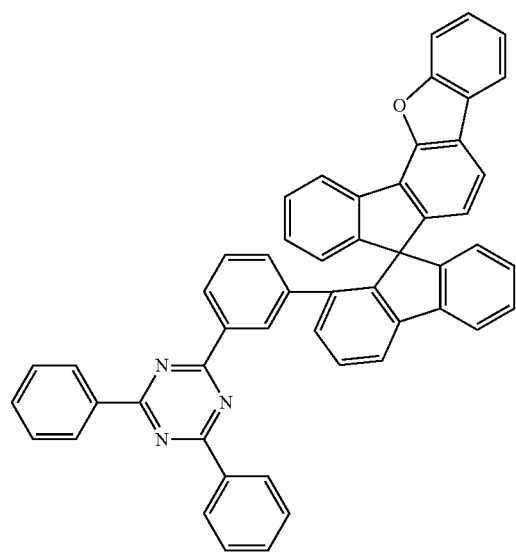 [SMILES: c1ccc(-c2nc(-c3ccccc3)nc(-c3cccc(-c4cccc5c4C4(c6ccccc6-5)c5ccccc5-c5c4ccc4c5oc5ccccc54)c3)n2)cc1]
4-3
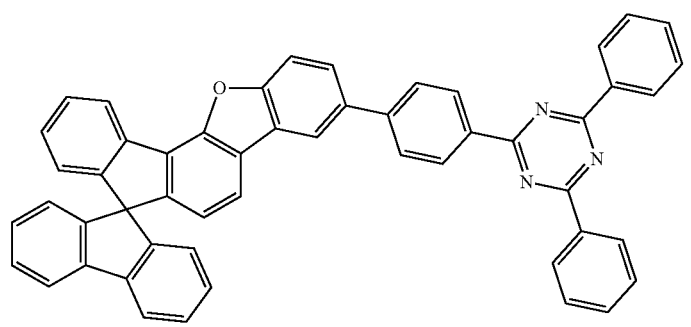 [SMILES: c1ccc(-c2nc(-c3ccccc3)nc(-c3ccc(-c4ccc5oc6c7c(ccc6c5c4)C4(c5ccccc5-c5ccccc54)c4ccccc4-7)cc3)n2)cc1]
4-5
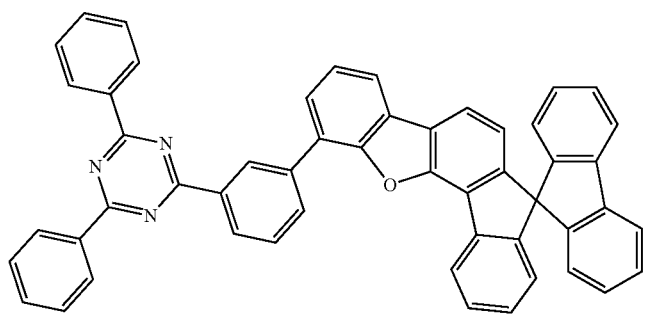 [SMILES: c1ccc(-c2nc(-c3ccccc3)nc(-c3cccc(-c4cccc5c4oc4c6c(ccc45)C4(c5ccccc5-c5ccccc54)c4ccccc4-6)c3)n2)cc1]
4-11

The invention claimed is:

1. A compound of formula (III'), (IV'), (V'), (VI'), or (VII'):

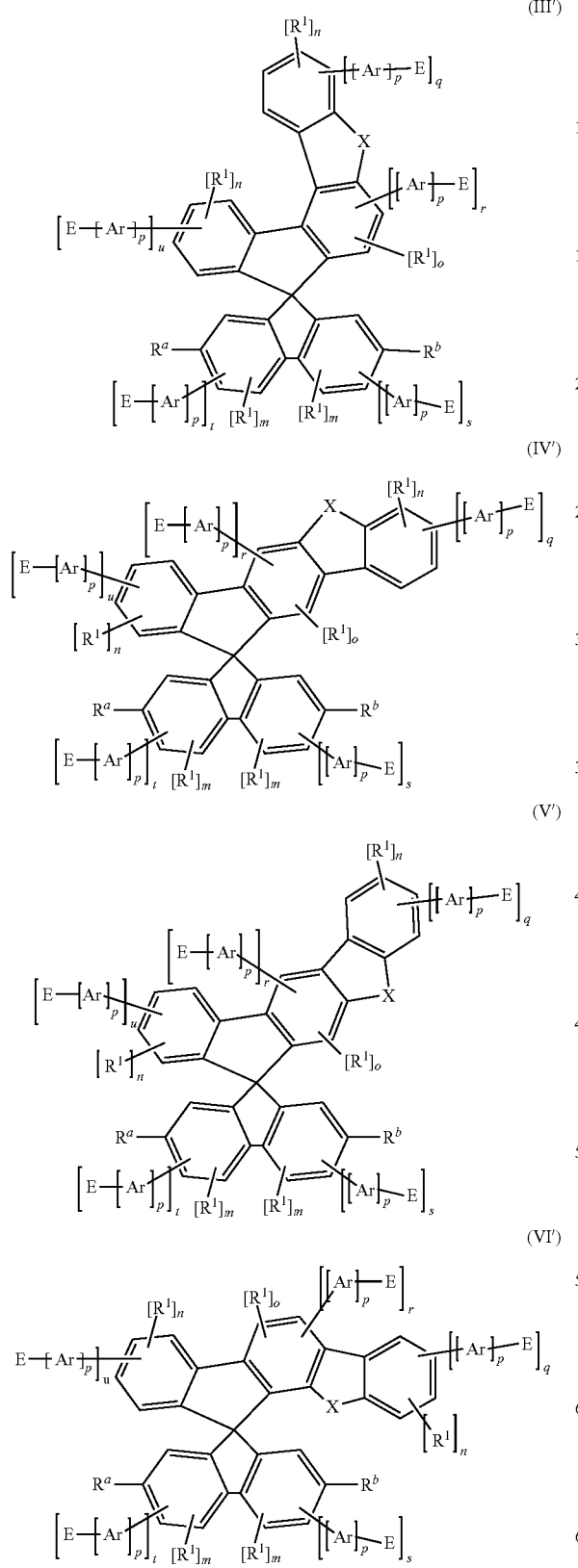

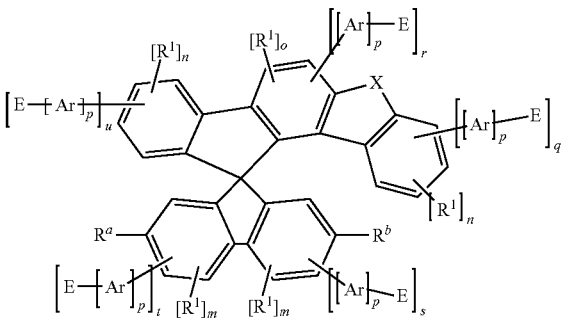

wherein
X is O, S, or C(R$^1$)$_2$;
Ar is on each occurrence, identically or differently, an aryl group having 6 to 40 C atoms or a heteroaryl group having 3 to 40 C atoms, each of which is optionally substituted by one or more radicals R$^1$;
R$^1$ is on each occurrence, identically or differently, H, D, F, Cl, Br, I, CHO, C(=O)Ar$^1$, P(=O)(Ar$^1$)$_2$, S(=O) Ar$^1$, S(=O)$_2$Ar$^1$, CN, NO$_2$, Si(R$^2$)$_3$, B(OR$^2$)$_2$, OSO$_2$R$^2$, a straight-chain alkyl, alkoxy, or thioalkoxy group having 1 to 40 C atoms or a branched or cyclic alkyl, alkoxy, or thioalkoxy group having 3 to 40 C atoms, each of which is optionally substituted by one or more radicals R$^2$, and wherein one or more non-adjacent CH$_2$ groups are optionally replaced by R$^2$C=CR$^2$, C≡C, Si(R$^2$)$_2$, Ge(R$^2$)$_2$, Sn(R$^2$)$_2$, C=O, C=S, C=Se, P(=O)(R$^2$), SO, SO$_2$, O, S, or CONR$^2$, and wherein one or more H atoms are optionally replaced by D, F, Cl, Br, I, CN, or NO$_2$, an aromatic or heteroaromatic ring system having 5 to 40 aromatic ring atoms, which is optionally substituted by one or more radicals R$^2$, or an aryloxy or heteroaryloxy group having 5 to 40 aromatic ring atoms, which is optionally substituted by one or more radicals R$^2$, or a combination of these systems; and wherein two or more adjacent substituents R$^1$ optionally define a mono- or polycyclic, aliphatic or aromatic ring system with one another;
R$^2$ is on each occurrence, identically or differently, H, D, F, Cl, Br, I, CHO, C(=O)Ar$^1$, P(=O)(Ar$^1$)$_2$, S(=O)$_2$ Ar$^1$, S(=O)$_2$Ar$^1$, CN, NO$_2$, Si(R$^3$)$_3$, B(OR$^3$)$_2$, OSO$_2$R$^3$, a straight-chain alkyl, alkoxy or thioalkoxy group having 1 to 40 C atoms or a branched or cyclic alkyl, alkoxy, or thioalkoxy group having 3 to 40 C atoms, each of which is optionally substituted by one or more radicals R$^3$, wherein one or more non-adjacent CH$_2$, groups are optionally replaced by C≡C, Si(R$^3$)$_2$, Ge(R$^3$)$_2$, Sn(R$^3$)$_2$, C=O, C=S, C=Se, P(=O)(R$^3$), SO, SO$_2$, O, S, or CONR$^3$, and wherein one or more H atoms are optionally replaced by D, F, Cl, Br, I, CN, or NO$_2$, or a combination of these systems; and wherein two or more adjacent substituents R$^2$ optionally define a mono- or polycyclic, aliphatic or aromatic ring system with one another;
Ar$^1$ is on each occurrence, identically or differently, an aromatic or heteroaromatic ring system having 5 to 30 aromatic ring atoms, which is optionally substituted by one or more radicals R$^2$; wherein two radicals Ar$^1$ bonded to the same phosphorus atom are also optionally linked to one another by a single bond or a bridge selected from the group consisting of B(R³), C(R³), Si(R³)₂, C=O, C=NR³, C=C(R³)₂, O, S, S=O, SO₂, N(R³), P(R³), and P(=O)R³;

R³ is on each occurrence, identically or differently, H, D, F, or an aliphatic, aromatic and/or heteroaromatic hydrocarbon radical having 1 to 20 C atoms, wherein one or more H atoms of the hydrocarbon radical are optionally replaced by F; and wherein two or more adjacent substituents R³ optionally define a mono- or polycyclic, aliphatic or aromatic ring system with one another;

n is on each occurrence, identically or differently, 0, 1, 2, 3, or 4;

m is on each occurrence, identically or differently, 0, 1, 2, or 3;

o is on each occurrence, identically or differently, 0, 1, or 2;

p is on each occurrence, identically or differently, 0 or 1;

q, r, and u
are, on each occurrence, 0;

s and t
are, on each occurrence, identically or differently, 0 or 1;

E is an electron-transporting group, which is optionally substituted by one or more radicals R¹;

Rᵃ is, independently, H, D, or F;

Rᵇ is, independently, H, D, or F;

with the proviso that
the compound of formula (III'), (IV'), (V'), (VI') or (VII') contains at least one electron-transporting group E;
the sum of all indices m, s and, t is less than 7;
the sum of all indices n, q and, u is less than 9; and
the sum of the indices r and o is less than 3.

2. The compound of claim 1, wherein the sum of s, t, and the electron-transporting groups E present in the groups Rᵃ and Rᵇ is less than or equal to 1.

3. The compound of claim 1, wherein p is 0, so that E is bonded directly to the benzofuran or spiro group.

4. The compound of claim 1, wherein at least one radical containing an electron-transporting group E is bonded in position 1', 3', 4, 5', 6', 8' of the spirobifluorene skeleton.

5. The compound of claim 1, wherein the compound of formula (I) comprises one or two electron-transporting groups E.

6. The compound of claim 1, wherein the electron-transporting group E is a heteroaryl group having 5 to 60 aromatic ring atoms.

7. The compound of claim 6, wherein the electron-transporting group E comprises at least one structure selected from the group consisting of triazines, pyrimidines, pyrazines, imidazoles, benzimidazoles, and pyridines.

8. The compound of claim 6, wherein the electron-transporting group E comprises at least one structure selected from the group consisting of formulae (E-1) through (E-10):

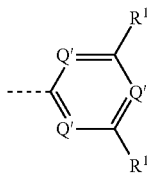
(E-1)

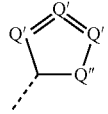
(E-2)

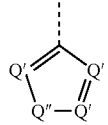
(E-3)

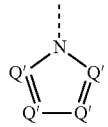
(E-4)

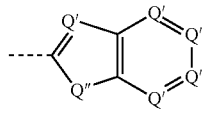
(E-5)

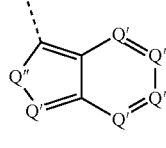
(E-6)

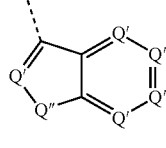
(E-7)

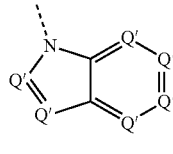
(E-8)

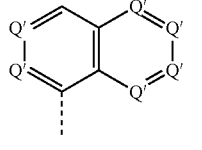
(E-9)

(E-10)

wherein the dashed bond marks the bonding position,

Q' is on each occurrence, identically or differently, CR¹ or N, and

Q" is NR¹, O, or S, and wherein at least one Q' is N and/or at least one Q" is NR¹.

9. The compound of claim 6, wherein the electron-transporting group E comprises at least one structure selected from the group consisting of formulae (E-11) through (E-19):

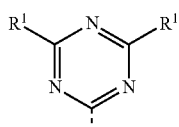 (E-11)

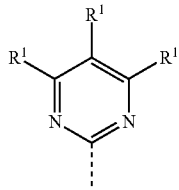 (E-12)

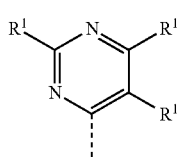 (E-13)

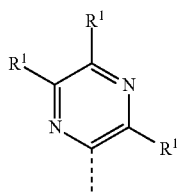 (E-14)

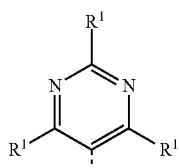 (E-15)

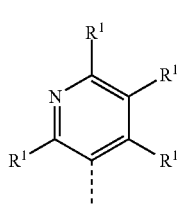 (E-16)

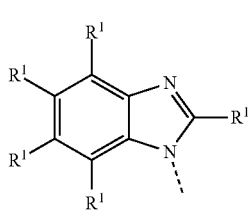 (E-17)

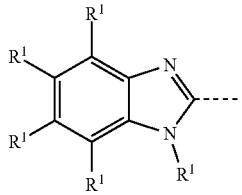 (E-18)

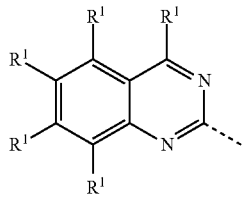 (E-19)

wherein the dashed bond marks the bonding position.

10. The compound of claim 8, wherein at least one of the radicals $R^1$ in the structures of formulae (E-1) through (E-10) is Ar.

11. The compound of claim 9, wherein at least one of the radicals $R^1$ in the structures of formulae (E-11) through (E-19) is Ar.

12. An oligomer, polymer, or dendrimer comprising one or more compounds of claim 1, wherein one or more bonds are present from the compound to the oligomer, polymer, or dendrimer.

13. A composition comprising at least one compound of claim 1 and at least one organofunctional material.

14. A composition comprising at least one oligomer, polymer, or dendrimer of claim 12 and at least one organofunctional material.

15. A formulation comprising at least one compound of claim 1 and at least one solvent.

16. A formulation comprising an oligomer, polymer, or dendrimer of claim 12 and at least one solvent.

17. A formulation comprising at least one composition of claim 13 and at least one solvent.

18. A formulation comprising at least one composition of claim 14 and at least one solvent.

19. A process for preparing a compound of claim 1, comprising preparing the spirobifluorene skeleton, followed by introducing a radical containing an electron-transporting group via a coupling reaction.

20. A process for preparing an oligomer, polymer, or dendrimer of claim 12, comprising preparing the spirobifluorene skeleton, followed by introducing a radical containing an electron-transporting group via a coupling reaction.

21. An electronic device comprising at least one compound of claim 1.

22. The electronic device of claim 21, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field-quench devices, light-emitting electrochemical cells and organic laser diodes.

23. The compound of claim 1, wherein t is 0 and s is 1.

24. The compound of claim 1, wherein t is 1 and s is 0.

25. The compound of claim 1, wherein the compound is represented by the formula (III), (IV), (V), (VI), or (VII):

(III)

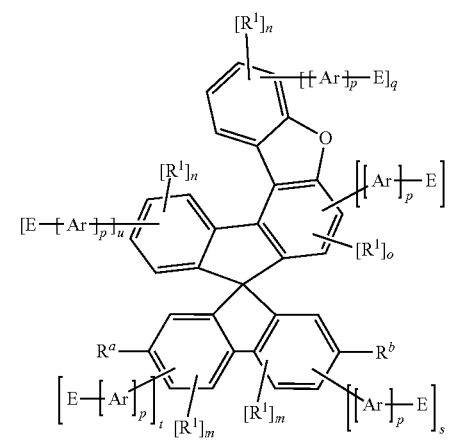

(IV)

(V)

(VI)

(VII)

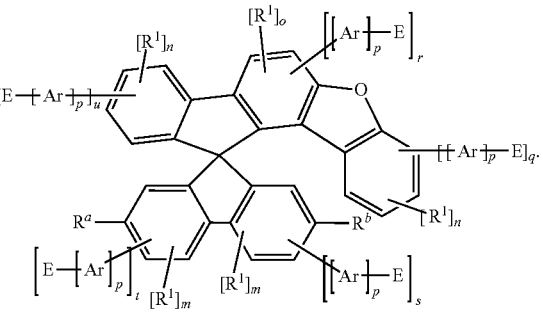

26. The compound of claim 1, wherein X is O or S.
27. A compound of the formula (II)

(II)

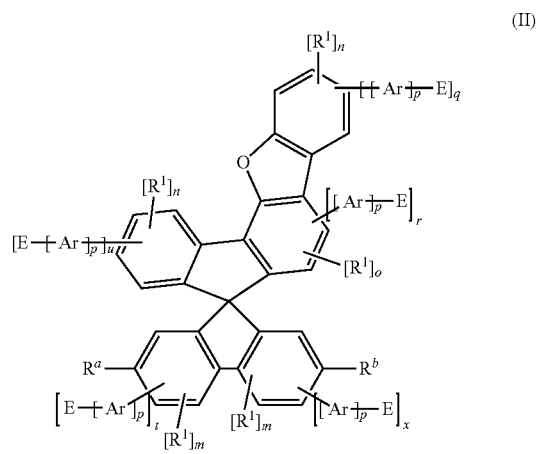

wherein
Ar is on each occurrence, identically or differently, an aryl group having 6 to 40 C atoms or a heteroaryl group having 3 to 40 C atoms, each of which is optionally substituted by one or more radicals $R^1$;

$R^1$ is on each occurrence, identically or differently, H, D, F, Cl, Br, I, CHO, C(=O)Ar$^1$, P(=O)(Ar$^1$)$_2$, S(=O) Ar$^1$, S(=O)$_2$Ar$^1$, CN, NO$_2$, Si(R$^2$)$_3$, B(OR$^2$)$_2$, OSO$_2$R$^2$, a straight-chain alkyl, alkoxy, or thioalkoxy group having 1 to 40 C atoms or a branched or cyclic alkyl, alkoxy, or thioalkoxy group having 3 to 40 C atoms, each of which is optionally substituted by one or more radicals $R^2$, and wherein one or more non-adjacent CH$_2$ groups are optionally replaced by R$^2$C=CR$^2$, C=C, Si(R$^2$)$_2$, Ge(R$^2$)$_2$, Sn(R$^2$)$_2$, C=O, C=S, C=Se, P(=O)(R$^2$), SO, SO$_2$, O, S, or CONR$^2$, and wherein one or more H atoms are optionally replaced by D, F, Cl, Br, I, CN, or NO$_2$, an aromatic or heteroaromatic ring system having 5 to 40 aromatic ring atoms, which is optionally substituted by one or more radicals R$^2$, or an aryloxy or heteroaryloxy group having 5 to 40 aromatic ring atoms, which is optionally substituted by one or more radicals R$^2$, or a combination of these systems; and wherein two or more adjacent substituents R$^1$ optionally define a mono- or polycyclic, aliphatic or aromatic ring system with one another;

$R^2$ is on each occurrence, identically or differently, H, D, F, Cl, Br, I, CHO, C(=O)Ar$^1$, P(=O)(Ar$^1$)$_2$, S(=O)$_2$ Ar$^1$, S(=O)$_2$Ar$^1$, CN, NO$_2$, Si(R$^3$)$_3$, B(OR$^3$)$_2$, OSO$_2$R$^3$, a straight-chain alkyl, alkoxy or thioalkoxy group having 1 to 40 C atoms or a branched or cyclic alkyl, alkoxy, or thioalkoxy group having 3 to 40 C atoms, each of which is optionally substituted by one or more radicals R$^3$, wherein one or more non-adjacent CH$_2$, groups are optionally replaced by C≡C, Si(R$^3$)$_2$, Ge(R$^3$)$_2$, Sn(R$^3$)$_2$, C=O, C=S, C=Se, P(=O)(R$^3$), SO, SO$_2$, O, S, or CONR$^3$, and wherein one or more H atoms are optionally replaced by D, F, Cl, Br, I, CN, or NO$_2$, or a combination of these systems; and wherein two or more adjacent substituents R$^2$ optionally define a mono- or polycyclic, aliphatic or aromatic ring system with one another;

Ar$^1$ is on each occurrence, identically or differently, an aromatic or heteroaromatic ring system having 5 to 30 aromatic ring atoms, which is optionally substituted by one or more radicals R$^2$; wherein two radicals Ar$^1$ bonded to the same phosphorus atom are also optionally linked to one another by a single bond or a bridge selected from the group consisting of B(R$^3$), C(R$^3$), Si(R$^3$)$_2$, C=O, C=NR$^3$, C=C(R$^3$)$_2$, O, S, S=O, SO$_2$, N(R$^3$), P(R$^3$), and P(=O)R$^3$;

R$^3$ is on each occurrence, identically or differently, H, D, F, or an aliphatic, aromatic and/or heteroaromatic hydrocarbon radical having 1 to 20 C atoms, wherein one or more H atoms of the hydrocarbon radical are optionally replaced by F; and wherein two or more adjacent substituents R$^3$ optionally define a mono- or polycyclic, aliphatic or aromatic ring system with one another;

n is on each occurrence, identically or differently, 0, 1, 2, 3, or 4;

m is on each occurrence, identically or differently, 0, 1, 2, or 3;

o is on each occurrence, identically or differently, 0, 1, or 2;

p is on each occurrence, identically or differently, 0 or 1;

q, r, and u are, on each occurrence, 0;

s and t are, on each occurrence, identically or differently, 0 or 1;

E is an electron-transporting group, which is optionally substituted by one or more radicals R$^1$;

R$^a$ is, independently, H, D, or F;

R$^b$ is, independently, H, D, or F;

with the proviso that the compound of formula (II) contains at least one electron-transporting group E;

the sum of all indices m, s and, t is less than 7;

the sum of all indices n, q and, u is less than 9; and the sum of the indices r and o is less than 3.

* * * * *